(12) United States Patent
Lindbo et al.

(10) Patent No.: US 6,300,134 B1
(45) Date of Patent: Oct. 9, 2001

(54) RNA TRANSFORMATION VECTORS DERIVED FROM A SINGLE-COMPONENT RNA VIRUS AND CONTAIN AN INTERVENING SEQUENCE BETWEEN THE CAP AND THE 5' END

(75) Inventors: John A. Lindbo; Gregory P. Pogue; Thomas H. Turpen, all of Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

(21) Appl. No.: 09/502,711

(22) Filed: Feb. 11, 2000

Related U.S. Application Data

(63) Continuation-in-part of application No. 09/359,301, filed on Jul. 21, 1999, and a continuation-in-part of application No. 09/359,305, filed on Jul. 21, 1999, each is a continuation-in-part of application No. 09/232,170, filed on Jan. 15, 1999, which is a continuation-in-part of application No. 09/008,186, filed on Jan. 16, 1998.

(51) Int. Cl.$^7$ .......................... C12N 15/82; C12N 15/00; C12P 19/34; C07H 21/04; C07H 21/02

(52) U.S. Cl. ..................... 435/468; 435/69.1; 435/91.1; 435/91.51; 435/235.1; 435/32.01; 536/23.1; 536/23.72; 536/24.1; 536/24.5

(58) Field of Search ................................ 435/6, 91.1, 69.1, 435/91.3, 70.1, 91.51, 91.5, 235.1, 468, 172.3, 475, 320.1; 536/23.1, 24.1, 24.5, 23.72

(56) References Cited

U.S. PATENT DOCUMENTS

| | | |
|---|---|---|
| 5,173,410 | * 12/1992 | Ahlquist .............................. 435/91.3 |
| 5,316,931 | 5/1994 | Donson et al. . |
| 5,491,076 | 2/1996 | Carrington et al. . |
| 5,500,360 | 3/1996 | Ahlquist et al. . |
| 5,589,367 | 12/1996 | Donson et al. . |
| 5,766,885 | 6/1998 | Carrington et al. . |
| 5,811,653 | 9/1998 | Turpen . |
| 5,846,795 | 12/1998 | Ahlquist et al. . |
| 5,866,785 | 2/1999 | Donson et al. . |
| 5,977,438 | 11/1999 | Turpen et al. . |

FOREIGN PATENT DOCUMENTS

| | | |
|---|---|---|
| 0194809 B1 | 3/1991 | (EP) . |
| WO 98/36083 | 8/1995 | (WO) . |
| WO 95/34668 | 12/1995 | (WO) . |
| WO 99/36516 | 7/1999 | (WO) . |
| WO 99/50429 | 10/1999 | (WO) . |

OTHER PUBLICATIONS

Scheets et al. Virology, vol. 193, pp. 1006–1009, 1993.*
Xiong et al., Virology, vol. 182, pp. 388–392, 1991.*
Ex parte Ahlquist, et al., Decision of the US PTO Board of Patent Appeals and Interferences, dated May 18, 1992 in file of U.S. Serial No. 07/368,939, filed Jun. 19, 1989, available in file of U.S. Patent No. 5,846,795, filed Jun. 5, 1995.
Ahlquist, P. et al., "Multicomponent RNA plant virus infection derived from cloned viral cDNA," *Proc. Natl. Acad. Sci. USA* 81:7066–7070 (1984).
Ahlquist, P. et al., "Sindbis Virus Proteins nsP1 and nsP2 Contain Homology to Nonstructural Proteins from Several RNA Plant Viruses," *J. Virol.*, vol. 53(2):536–542 (1985).
Baulcombe, D., "Fast Forward genetics based on virus–induced gene silencing," Current Opinion in Plant Biology, vol. 2(2): 109–113 (1999) XP002118432.
Chapman, S. et al., "Potato virus X as a vector for gene expression in plants," *The Plant Journal*, vol. 2(4): 549–557 (1992).
Contreras, R., et al., "Simple, efficient in vitro synthesis of capped RNA useful for direct expression of cloned eukaryotic genes," *Nucleic Acids Res.*, vol. 10(20):6353–6362(1982).
Davies, J.W. and R. Hull, "Genome Expression of Plant Positive–strand RNA Viruses,"*J. Gen. Virol*, 61:1–14 (1982).
Davis, R., et al., *Advanced Bacterial Genetics*, (1980).
Dawson et al., "cDNA cloning of the conmplete genome of tobacco mosaic virus and production of infections transcripts," *Proc. Natl. Acad. Sci. USA* 83:1832–1836 (1986).
Franssen, H, et al., "Homologous sequences in non–structural proteins from cowpea mosaic virus and picornaviruses," *EMBO Journal* 3,855, vol. 3(4): 855–861 (1984).
Grossman, L. and K. Moldave, "Methods in Enzymology," *Meth. Enzymol.*, vol.65 (1980).
Haizel, T, et al., "Characterization of proteins that interact woth the GTP–bound form of the regulatory GTPase Ran in Arabidopsis," *Plant Journal*, vol. 11(1):93–103 (1997).

(List continued on next page.)

Primary Examiner—Sean McGarry
Assistant Examiner—Jane Zara
(74) *Attorney, Agent, or Firm*—Albert P. Halluin, Esq.; Thomas Gallegos, Esq.; Viola T. Kung, Esq.

(57) ABSTRACT

This invention is directed to a plus strand RNA viral vector for transformation of a host organism with a foreign RNA, and expression of said foreign RNA. The foreign RNA is inserted into an infective RNA viral segment containing cis-acting viral replication elements, and allowed to infect the host organism. The RNA vector is modified to obtain infectivity by including an intervening sequence between the cap and the 5' end. The modified RNA is able to tolerate the exogeneous RNA segment without disrupting the replication of the modified RNA, in the absence of a trans-acting viral replication element in a single component plant virus host cell.

26 Claims, 24 Drawing Sheets

OTHER PUBLICATIONS

Haseloff, J. et al., "Striking similarities in amino acid sequence among nonstructural proteins encoded by RNA viruses that have dissimilar genomic organization," Proc. Nat. Acad. Sci. USA 81:4358–4362 (1984).

J. H. Miller, Experiment's in Molecular Genetics; Cold Spring Harbor Laboratory, New York (1972).

Keith, J. and Fraenkel–Conrat, "Tobacco Mosaic virus RNA carriers 5'–Terminal triphosphorylated guanosine blocked by 5'–linked 7–methylguanosine," *FEBS Lett.* 57(1):31–33 (1975).

Maniatis, T., et al., Molecular Cloning—1st Edition., Cold Spring Harbor Laboratory (1982).

Sablowski, R., et al., "Expression of a Flower–specific Myb protein in leaf cells using a viral vector causes ectopic activation of a target promoter," Proceedings of the National Academy of Sciences of USA, National Academy of Science, vol. 92:6901–6905 (1995).

Schleif, R.F. and P. C. Wensink, Practical Methods in Molecular Biology (1982).

Wu, R, "Recombinant DNA," Methods in Enzymology, vol. 101(1983).

Wu, R, "Recombinant DNA," Methods in Enzymology, vol. 68 (1979).

Zimmern, D., "The 5' end group of tobacco mosaic virus RNA is m7 G5' ppp5' Gp," *Nucleic Acid Res.*, vol. 2(7):1189–1201 (1975).

* cited by examiner

P1037
30B-GFPc3

GTATTTTTACAACAATTACCAACAACAACAAACAACAGACAACATTACAATT
ACTATTTACAATTACAATGGCATACACACAGACAGCTACCACATCAGCTTTG
CTGGACACTGTCCGAGGAAACAACTCCTTGGTCAATGATCTAGCAAAGCGTC
GTCTTTACGACACAGCGGTTGAAGAGTTTAACGCTCGTGACCGCAGGCCCAA
GGTGAACTTTTCAAAAGTAATAAGCGAGGAGCAGACGCTTATTGCTACCCGG
GCGTATCCAGAATTCCAAATTACATTTTATAACACGCAAAATGCCGTGCATTC
GCTTGCAGGTGGATTGCGATCTTTAgAACTGGAATATCTGATGATGCAAATTC
CCTACGGATCATTGACTTATGACATAGGCGGGAATTTTGCATCGCATCTGTTC
AAGGGACGAGCATATGTACACTGCTGCATGCCCAACCTGGACGTTCGAGACA
TCATGCGGCACGAAGGCCAGAAGACAGTATTGAACTATACCTTTCTAGGCT
AGAGAGAGGGGGGAAAACAGTCCCCAACTTCCAAAAGGAAGCATTTGACAG
ATACGCAGAAATTCCTGAAGACGCTGTCTGTCACAATACTTTCCAGACATGC
GAACATCAGCCGATGCAGCAATCAGGCAGAGTGTATGCCATTGCGCTACACA
GCATATATGACATACCAGCCGATGAGTTCGGGGCGGCACTCTTGAGGAAAAA
TGTCCATACGTGCTATGCCGCTTCCACTTCTCCGAGAACCTGCTTCTTGAAG
ATTCATGCGTCAATTTGGACGAAATCAACGCGTGTTTTTCGCGCGATGGAGAC
AAGTTGACCTTTTCTTTTGCATCAGAGAGTACTCTTAATTACTGTCATAGTTAT
TCTAATATTCTTAAGTATGTGTGCAAAACTTACTTCCCGGCCTCTAATAGAGA
GGTTTACATGAAGGAGTTTTTAGTCACCAGAGTTAATACCTGGTTTTGTAAGT
TTTCTAGAATAGATACTTTTCTTTTGTACAAAGGTGTGGCCCATAAAAGTGTA
GATAGTGAGCAGTTTTATACTGCAATGGAAGACGCATGGCATTACAAAAAGA
CTCTTGCAATGTGCAACAGCGAGAGAATCCTCCTTGAGGATTCATCATCAGTC
AATTACTGGTTTCCCAAAATGAGGGATATGGTCATCGTACCATTATTCGACAT
TTCTTTGGAGACTAGTAAGAGGACGCGCAAGGAAGTCTTAGTGTCCAAGGAT
TTCGTGTTTACAGTGCTTAACCACATTCGAACATACCAGGCGAAAGCTCTTAC
ATACGCAAATGTTTTGTCCTTCGTCGAATCGATTCGATCGAGGGTAATCATTA
ACGGTGTGACAGCGAGGTCCGAATGGGATGTGGACAAATCTTTGTTACAATC
CTTGTCCATGACGTTTTACCTGCATACTAAGCTTGCCGTTCTAAAGGATGACT
TACTGATTAGCAAGTTTAGTCTCGGTTCGAAAACGGTGTGCCAGCATGTGTGG
GATGAGATTTCGCTGGCGTTTGGGAACGCATTTCCCTCCGTGAAAGAGAGGC
TCTTGAACAGGAAACTTATCAGAGTGGCAGGCGACGCATTAGAGATCAGGGT
GCCTGATCTATATGTGACCTTCCACGACAGATTAGTGACTGAGTACAAGGCCT
CTGTGGACATGCCTGCGCTTGACATTAGGAAGAAGATGGAAGAAACGGAAGT
GATGTACAATGCACTTTCAGAATTATCGGTGTTAAGGGAGTCTGACAAATTC
GATGTTGATGTTTTTCCCAGATGTGCCAATCTTTGGAAGTTGACCCAATGAC
GGCAGCGAAGGTTATAGTCGCGGTCATGAGCAATGAGAGCGGTCTGACTCTC
ACATTTGAACGACCTACTGAGGCGAATGTTGCGCTAGCTTTACAGGATCAAG
AGAAGGCTTCAGAAGGTGCATTGGTAGTTACCTCAAGAGAAGTTGAAGAACC
GTCCATGAAGGGTTCGATGGCCAGAGGAGAGTTACAATTAGCTGGTCTTGCT
GGAGATCATCCGGAATCGTCCTATTCTAAGAACGAGGAGATAGAGTCTTTAG
AGCAGTTTCATATGGCGACGGCAGATTCGTTAATTCGTAAGCAGATGAGCTC
GATTGTGTACACGGGTCCGATTAAAGTTCAGCAAATGAAAAACTTTATCGAT

FIG 1-1

```
AGCCTGGTAGCATCACTATCTGCTGCGGTGTCGAATCTCGTCAAGATCCTCAA
AGATACAGCTGCTATTGACCTTGAAACCCGTCAAAAGTTTGGAGTCTTGGAT
GTTGCATCTAGGAAGTGGTTAATCAAACCAACGGCCAAGAGTCATGCATGGG
GTGTTGTTGAAACCCACGCGAGGAAGTATCATGTGGCGCTTTTGGAATATGA
TGAGCAGGGTGTGGTGACATGCGATGATTGGAGAAGAGTAGCTGTTAGCTCT
GAGTCTGTTGTTTATTCCGACATGGCGAAACTCAGAACTCTGCGCAGACTGCT
TCGAAACGGAGAACCGCATGTCAGTAGCGCAAAGGTTGTTCTTGTGGACGGA
GTTCCGGGCTGTGGAAAAACCAAAGAAATTCTTTCCAGGGTTAATTTTGATG
AAGATCTAATTTTAGTACCTGGGAAGCAAGCCGCGGAAATGATCAGAAGACG
TGCGAATTCCTCAGGGATTATTGTGGCCACGAAGGACAACGTTAAAACCGTT
GATTCTTTCATGATGAATTTTGGGAAAAGCACACGCTGTCAGTTCAAGAGGTT
ATTCATTGATGAAGGGTTGATGTTGCATACTGGTTGTGTTAATTTTCTTGTGG
CGATGTCATTGTGCGAAATTGCATATGTTTACGGAGACACACAGCAGATTC
CATACATCAATAGAGTTTCAGGATTCCCGTACCCCGCCCATTTTGCCAAATTG
GAAGTTGACGAGGTGGAGACACGCAGAACTACTCTCCGTTGTCCAGCCGATG
TCACACATTATCTGAACAGGAGATATGAGGGCTTTGTCATGAGCACTTCTTCG
GTTAAAAAGTCTGTTTCGCAGGAGATGGTCGGCGGAGCCgCCGTGATCAATC
CGATCTCAAAACCCTTGCATGGCAAGATCTTGACTTTTACCCAATCGGATAAA
GAAGCTCTGCTTTCAAGAGGGTATTCAGATGTTCACACTGTGCATGAAGTGC
AAGGCGAGACATACTCTGATGTTTCACTAGTTAGGTTAACCCCTACACCGGTC
TCCATCATTGCAGGAGACAGCCCACATGTTTTGGTCGCATTGTCAAGGCACAC
CTGTTCGCTCAAGTACTACACTGTTGTTATGGATCCTTTAGTTAGTATCATTAG
AGATCTAGAGAAACTTAGCTCGTACTTGTTAGATATGTATAAGGTCGATGCA
GGAACACAATAGCAATTACAGATTGACTCGGTGTTCAAAGGTTCCAATCTTTT
TGTTGCAGCGCCAAAGACTGGTGATATTTCTGATATGCAGTTTTACTATGATA
AGTGTCTCCCAGGCAACAGCACCATGATGAATAATTTTGATGCTGTTACCATG
AGGTTGACTGACATTTCATTGAATGTCAAAGATTGCATATTGGATATGTCTAA
GTCTGTTGCTGCGCCTAAGGATCAAATCAAACCACTAATACCTATGGTACGA
ACGGCGGCAGAAATGCCACGCCAGACTGGACTATTGGAAAATTTAGTGGCGA
TGATTAAAAGAAACTTTAACGCACCCGAGTTGTCTGGCATCATTGATATTGAA
AATACTGCATCTTTGGTTGTAGATAAGTTTTTTGATAGTTATTTGCTTAAAGA
AAAAAGAAAACCAAATAAAAATGTTTCTTTGTTCAGTAGAGAGTCTCTCAAT
AGATGGTTAGAAAAGCAGGAACAGGTAACAATAGGCCAGCTCGCAGATTTTG
ATTTTGTGGATTTGCCAGCAGTTGATCAGTACAGACACATGATTAAAGCACA
ACCCAAACAAAAGTTGGACACTTCAATCCAAACGGAGTACCCGGCTTTGCAG
ACGATTGTGTACCATTCAAAAAAGATCAATGCAATATTCGGCCCGTTGTTTAG
TGAGCTTACTAGGCAATTACTGGACAGTGTTGATTCGAGCAGATTTTGTTTT
TCACAAGAAAGACACCAGCGCAGATTGAGGATTTCTTCGGAGATCTCGACAG
TCATGTGCCGATGGATGTCTTGGAGCTGGATATATCAAAATACGACAAATCT
CAGAATGAATTCCACTGTGCAGTAGAATACGAGATCTGGCGAAGATTGGGTT
TCGAAGACTTCTTGGGAGAAGTTTGGAAACAAGGGCATAGAAAGACCACCCT
CAAGGATTATACCGCAGGTATAAAAACTTGCATCTGGTATCAAAGAAAGAGC
GGGGACGTCACGACGTTCATTGGAAACACTGTGATCATTGCTGCATGTTTGGC
CTCGATGCTTCCGATGGAGAAAATAATCAAAGGAGCCTTTTGCGGTGACGAT
AGTCTGCTGTACTTTCCAAAGGGTTGTGAGTTTCCGGATGTGCAACACTCCG
```

FIG 1-2

```
CGAATCTTATGTGGAATTTTGAAGCAAAACTGTTTAAAAAACAGTATGGATA
CTTTTGCGGAAGATATGTAATACATCACGACAGAGGATGCATTGTGTATTAC
GATCCCCTAAAGTTGATCTCGAAACTTGGTGCTAAACACATCAAGGATTGGG
AACACTTGGAGGAGTTCAGAAGGTCTCTTTGTGATGTTGCTGTTTCGTTGAAC
AATTGTGCGTATTACACACAGTTGGACGACGCTGTATGGGAGGTTCATAAGA
CCGCCCCTCCAGGTTCGTTTGTTTATAAAAGTCTGGTGAAGTATTTGTCTGAT
AAAGTTCTTTTTAGAAGTTTGTTTATAGATGGCTCTAGTTGTTAAAGGAAAAG
TGAATATCAATGAGTTTATCGACCTGACAAAAATGGAGAAGATCTTACCGTC
GATGTTTACCCTGTAAAGAGTGTTATGTGTTCCAAAGTTGATAAAATAATGG
TTCATGAGAATGAGTCATTGTCAGGGGTGAACCTTCTTAAAGGAGTTAAGCTT
ATTGATAGTGGATACGTCTGTTTAGCCGGTTTGGTCGTCACGGGCGAGTGGA
ACTTGCCTGACAATTGCAGAGGAGGTGTGAGCGTGTGTCTGGTGGACAAAAG
GATGGAAAGAGCCGACGAGGCCACTCTCGGATCTTACTACACAGCAGCTGCA
AAGAAAAGATTTCAGTTCAAGGTCGTTCCCAATTATGCTATAACCACCCAGG
ACGCGATGAAAAACGTCTGGCAAGTTTTAGTTAATATTAGAAATGTGAAGAT
GTCAGCGGGTTTCTGTCCGCTTTCTCTGGAGTTTGTGTCGGTGTGTATTGTTTA
TAGAAATAATATAAAATTAGGTTTGAGAGAGAAGATTACAAACGTGAGAGA
CGGAGGGCCCATGGAACTTACAGAAGAAGTCGTTGATGAGTTCATGGAAGAT
GTCCCTATGTCGATCAGGCTTGCAAAGTTCGATCTCGAACCGGAAAAAAGA
GTGATGTCCGCAAAGGGAAAAATAGTAGTAGTGATCGGTCAGTGCCGAACAA
GAACTATAGAAATGTTAAGGATTTTGGAGGAATGAGTTTTAAAAAGAATAAT
TTAATCGATGATGATTCGGAGGCTACTGTCGCCAATCGGATTCGTTTTAAAT
AGATCTTACAGTATCACTACTCCATCTCAGTTCGTGTTCTTGTCATTAATTAAA
TGGCTAGCAAAGGAGAAGAACTTTTCACTGGAGTTGTCCCAATTCTTGTTGAA
TTAGATGGTGATGTTAATGGGCACAAATTTTCTGTCAGTGGAGAGGGTGAAG
GTGATGCTACATACGGAAAGCTTACCCTTAAATTTATTTGCACTACTGGAAAA
CTACCTGTTCCATGGCCAACACTTGTCACTACTTTCTCTTATGGTGTTCAATGC
TTTTCCCGTTATCCGGATCATATGAAACGGCATGACTTTTTCAAGAGTGCCAT
GCCCGAAGGTTATGTACAGGAACGCACTATATCTTTCAAAGATGACGGGAAC
TACAAGACGCGTGCTGAAGTCAAGTTTGAAGGTGATACCCTTGTTAATCGTAT
CGAGTTAAAAGGTATTGATTTTAAAGAAGATGGAAACATTCTCGGACACAAA
CTCGAGTACAACTATAACTCACACAATGTATACATCACGGCAGACAAACAAA
AGAATGGAATCAAAGCTAACTTCAAAATTCGCCACAACATTGAAGATGGATC
CGTTCAACTAGCAGACCATTATCAACAAATACTCCAATTGGCGATGGCCCT
GTCCTTTTACCAGACAACCATTACCTGTCGACACAATCTGCCCTTTCGAAAGA
TCCCAACGAAAAGCGTGACCACATGGGCCTTCTTGAGTTTGTAACTGCTGCTG
GGATTACACATGGCATGGATGAGCTCTACAAATAATGACACTCGAGGGGTAG
TCAAGATGCATAATAAATAACGGATTGTGTCCGTAATCACACGTGGTGCGTA
CGATAACGCATAGTGTTTTTCCCTCCACTTAAATCGAAGGGTTGTGTCTTGGA
TCGCGCGGGTCAAATGTATATGGTTCATATACATCCGCAGGCACGTAATAAA
GCGAGGGGTTCGGGTCGAGGTCGGCTGTGAAACTCGAAAAGGTTCCGGAAA
ACAAAAAGAGAGTGGTAGGTAATAGTGTTAATAATAAGAAAATAAATAAT
AGTGGTAAGAAAGGTTTGAAAGTTGAGGAAATTGAGGATAATGTAAGTGATG
ACGAGTCTATCGCGTCATCGAGTACGTTTAATCAATATGCCTTATACAATCA
ACTCTCCGAGCCAATTTGTTTACTTAAGTTCCGCTTATGCAGATCCTGTGCAG
CTGATCAATCTGTGTACAAATGCATTGGGTAACCAGTTTCAAACGCAACAAG
```

FIG 1-3

```
CTAGGACAACAGTCCAACAGCAATTTGCGGATGCCTGGAAACCTGTGCCTAG
TATGACAGTGAGATTTCCTGCATCGGATTTCTATGTGTATAGATATAATTCGA
CGCTTGATCCGTTGATCACGGCGTTATTAAATAGCTTCGATACTAGAAATAGA
ATAATAGAGGTTGATAATCAACCCGCACCGAATACTACTGAAATCGTTAACG
CGACTCAGAGGGTAGACGATGCGACTGTAGCTATAAGGGCTTCAATCAATAA
TTTGGCTAATGAACTGGTTCGTGGAACTGGCATGTTCAATCAAGCAAGCTTTG
AGACTGCTAGTGGACTTGTCTGGACCACAACTCCGGCTACTTAGCTATTGTTG
TGAGATTTCCTAAAATAAAGTCACTGAAGACTTAAAATTCAGGGTGGCTGAT
ACCAAAATCAGCAGTGGTTGTTCGTCCACTTAAATATAACGATTGTCATATCT
GGATCCAACAGTTAAACCATGTGATGGTGTATACTGTGGTATGGCGTAAAAC
AACGGAAAAGTCGCTGAAGACTTAAAATTCAGGGTGGCTGATACCAAAATCA
GCAGTGGTTGTTCGTCCACTTAAAAATAACGATTGTCATATCTGGATCCAACA
GTTAAACCATGTGATGGTGTATACTGTGGTATGGCGTAAACAACGGAGAGGT
TCGAATCCTCCCCTAACCGCGGgtagcggccca
```

FIG 1-4

SBS 60

```
GTATTTTTACAACAATTACCAACAACAACAAACAACAGACAACATTACAATT
ACTATTTACAATTACAATGGCATACACACAGACAGCTACCACATCAGCTTTGC
TGGACACTGTCCGAGGAAACAACTCCTTGGTCAATGATCTAGCAAAGCGTCG
TCTTTACGACACAGCGGTTGAAGAGTTTAACGCTCGTGACCGCAGGCCCAAG
GTGAACTTTTCAAAAGTAATAAGCGAGGAGCAGACGCTTATTGCTACCCGGG
CGTATCCAGAATTCCAAATTACATTTTATAACACGCAAAATGCCGTGCATTCG
CTTGCAGGTGGATTGCGATCTTTAGAACTGGAATATCTGATGATGCAAATTCC
CTACGGATCATTGACTTATGACATAGGCGGGAATTTTGCATCGCATCTGTTCA
AGGGACGAGCATATGTACACTGCTGCATGCCCAACCTGGACGTTCGAGACAT
CATGCGGCACGAAGGCCAGAAGACAGTATTGAACTATACCTTTCTAGGCTA
GAGAGAGGGGGGAAAACAGTCCCCAACTTCCAAAAGGAAGCATTTGACAGA
TACGCAGAAATTCCTGAAGACGCTGTCTGTCACAATACTTTCCAGACATGCG
AACATCAGCCGATGCAGCAATCAGGCAGAGTGTATGCCATTGCGCTACACAG
CATATATGACATACCAGCCGATGAGTTCGGGGCGGCACTCTTGAGGAAAAAT
GTCCATACGTGCTATGCCGCTTCCACTTCTCCGAGAACCTGCTTCTTGAAGA
TTCATGCGTCAATTTGGACGAAATCAACGCGTGTTTTCGCGCGATGGAGACA
AGTTGACCTTTTCTTTTGCATCAGAGAGTACTCTTAATTACTGTCATAGTTATT
CTAATATTCTTAAGTATGTGTGCAAAACTTACTTCCCGGCCTCTAATAGAGAG
GTTTACATGAAGGAGTTTTTAGTCACCAGAGTTAATACCTGGTTTTGTAAGTT
TTCTAGAATAGATACTTTTCTTTTGTACAAAGGTGTGGCCCATAAAAGTGTAG
ATAGTGAGCAGTTTTATACTGCAATGGAAGACGCATGGCATTACAAAAAGAC
TCTTGCAATGTGCAACAGCGAGAGAATCCTCCTTGAGGATTCATCATCAGTCA
ATTACTGGTTTCCCAAAATGAGGGATATGGTCATCGTACCATTATTCGACATT
TCTTTGGAGACTAGTAAGAGGACGCGCAAGGAAGTCTTAGTGTCCAAGGATT
TCGTGTTCACAGTGCTTAACCACATTCGAACATACCAGGCGAAAGCTCTTACA
TACGCAAATGTTTTGTCCTTCGTCGAATCGATTCGATCGAGGGTAATCATTAA
CGGTGTGACAGCGAGGTCCGAATGGGATGTGGACAAATCTTTGTTACAATCC
TTGTCCATGACGTTTTACCTGCATACTAAGCTTGCCGTTCTAAAGGATGACTT
ACTGATTAGCAAGTTTAGTCTCGGTTCGAAAACGGTGTGCCAGCATGTGTGG
GATGAGATTTCGCTGGCGTTTGGGAACGCATTTCCCTCCGTGAAAGAGAGGC
TCTTGAACAGGAAACTTATCAGAGTGGCAGGCGACGCATTAGAGATCAGGGT
GCCTGATCTATATGTGACCTTCCACGACAGATTAGTGACTGAGTACAAGGCCT
CTGTGGACATGCCTGCGCTTGACATTAGGAAGAAGATGGAAGAAACGGAAGT
GATGTACAATGCACTTTCAGAATTATCGGTGTTAAGGGAGTCTGACAAATTC
GATGTTGATGTTTTTTCCCAGATGTGCCAATCTTTGGAAGTTGACCCAATGAC
GGCAGCGAAGGTTATAGTCGCGGTCATGAGCAATGAGAGCGGTCTGACTCTC
ACATTTGAACGACCTACTGAGGCGAATGTTGCGCTAGCTTTACAGGATCAAG
AGAAGGCTTCAGAAGGTGCATTGGTAGTTACCTCAAGAGAAGTTGAAGAACC
GTCCATGAAGGGTTCGATGGCCAGAGGAGAGTTACAATTAGCTGGTCTTGCT
GGAGATCATCCGGAATCGTCCTATTCTAAGAACGAGGAGATAGAGTCTTTAG
AGCAGTTTCATATGGCGACGGCAGATTCGTTAATTCGTAAGCAGATGAGCTC
GATTGTGTACACGGGTCCGATTAAAGTTCAGCAAATGAAAAACTTTATCGAT
AGCCTGGTAGCATCACTATCTGCTGCGGTGTCGAATCTCGTCAAGATCCTCAA
AGATACAGCTGCTATTGACCTTGAAACCCGTCAAAAGTTTGGAGTCTTGGAT
```

FIG 2-1

```
GTTGCATCTAGGAAGTGGTTAATCAAACCAACGGCCAAGAGTCATGCATGGG
GTGTTGTTGAAACCCACGCGAGGAAGTATCATGTGGCGCTTTTGGAATATGA
TGAGCAGGGTGTGGTGACATGCGATGATTGGAGAAGAGTAGCTGTTAGCTCT
GAGTCTGTTGTTTATTCCGACATGGCGAAACTCAGAACTCTGCGCAGACTGCT
TCGAAACGGAGAACCGCATGTCAGTAGCGCAAAGGTTGTTCTTGTGGACGGA
GTTCCGGGCTGTGGAAAAACCAAAGAAATTCTTTCCAGGGTTAATTTTGATG
AAGATCTAATTTTAGTACCTGGGAAGCAAGCCGCGGAAATGATCAGAAGACG
TGCGAATTCCTCAGGGATTATTGTGGCCACGAAGGACAACGTTAAACCGTT
GATTCTTTCATGATGAATTTTGGGAAAAGCACACGCTGTCAGTTCAAGAGGTT
ATTCATTGATGAAGGGTTGATGTTGCATACTGGTTGTGTTAATTTTCTTGTGG
CGATGTCATTGTGCGAAATTGCATATGTTTACGGAGACACACAGCAGATTCC
ATACATCAATAGAGTTTCAGGATTCCCGTACCCCGCCCATTTTGCCAAATTGG
AAGTTGACGAGGTGGAGACACGCAGAACTACTCTCCGTTGTCCAGCCGATGT
CACACATTATCTGAACAGGAGATATGAGGGCTTTGTCATGAGCACTTCTTCGG
TTAAAAAGTCTGTTTCGCAGGAGATGGTCGGCGGAGCCGCCGTGATCAATCC
GATCTCAAAACCCTTGCATGGCAAGATCCTGACTTTTACCCAATCGGATAAA
GAAGCTCTGCTTTCAAGAGGGTATTCAGATGTTCACACTGTGCATGAAGTGC
AAGGCGAGACATACTCTGATGTTTCACTAGTTAGGTTAACCCCTACACCGGTC
TCCATCATTGCAGGAGACAGCCCACATGTTTTGGTCGCATTGTCAAGGCACAC
CTGTTCGCTCAAGTACTACACTGTTGTTATGGATCCTTTAGTTAGTATCATTAG
AGATCTAGAGAAACTTAGCTCGTACTTGTTAGATATGTATAAGGTCGATGCA
GGAACACAATAGCAATTACAGATTGACTCGGTGTTCAAAGGTTCCAATCTTTT
TGTTGCAGCGCCAAAGACTGGTGATATTTCTGATATGCAGTTTTACTATGATA
AGTGTCTCCCAGGCAACAGCACCATGATGAATAATTTTGATGCTGTTACCATG
AGGTTGACTGACATTTCATTGAATGTCAAAGATTGCATATTGGATATGTCTAA
GTCTGTTGCTGCGCCTAAGGATCAAATCAAACCACTAATACCTATGGTACGA
ACGGCGGCAGAAATGCCACGCCAGACTGGACTATTGGAAAATTTAGTGGCGA
TGATTAAAAGAAACTTTAACGCACCCGAGTTGTCTGGCATCATTGATATTGAA
AATACTGCATCTTTGGTTGTAGATAAGTTTTTTGATAGTTATTTGCTTAAAGA
AAAAAGAAAACCAAATAAAAATGTTTCTTTGTTCAGTAGAGAGTCTCTCAAT
AGATGGTTAGAAAAGCAGGAACAGGTAACAATAGGCCAGCTCGCAGATTTTG
ATTTTGTGGATTTGCCAGCAGTTGATCAGTACAGACACATGATTAAAGCACA
ACCCAAACAAAGTTGGACACTTCAATCCAAACGGAGTACCCGGCTTTGCAG
ACGATTGTGTACCATTCAAAAAAGATCAATGCAATATTCGGCCCGTTGTTTAG
TGAGCTTACCAGGCAATTACTGGACAGTGTTGATTCGAGCAGATTTTTGTTTT
TCACAAGAAAGACACCAGCGCAGATTGAGGATTTCTTCGGAGATCTCGACAG
TCATGTGCCGATGGATGTCTTGGAGCTGGATATATCAAAATACGACAAATCT
CAGAATGAATTCCACTGTGCAGTAGAATACGAGATCTGGCGAAGATTGGGTT
TCGAAGACTTCTTGGGAGAAGTTTGGAAACAAGGGCATAGAAAGACCACCCT
CAAGGATTATACCGCAGGTATAAAAACTTGCATCTGGTATCAAAGAAAGAGC
GGGGACGTCACGACGTTCATTGGAAACACTGTGATCATTGCTGCATGTTTGGC
CTCGATGCTTCCGATGGAGAAAATAATCAAAGGAGCCTTTTGCGGTGACGAT
AGTCTGCTGTACTTTCCAAAGGGTTGTGAGTTTCCGGATGTGCAACACTCCG
CGAATCTTATGTGGAATTTTGAAGCAAAACTGTTTAAAAACAGTATGGATA
CTTTTGCGGAAGATATGTAATACATCACGACAGAGGATGCATTGTGTATTAC
GATCCCCTAAAGTTGATCTCGAAACTTGGTGCTAAACACATCAAGGATTGGG
```

FIG 2-2

```
AACACTTGGAGGAGTTCAGAAGGTCTCTTTGTGATGTTGCTGTTTCGTTGAAC
AATTGTGCGTATTACACACAGTTGGACGACGCTGTATGGGAGGTTCATAAGA
CCGCCCCTCCAGGTTCGTTTGTTTATAAAGTCTGGTGAAGTATTTGTCTGAT
AAAGTTCTTTTTAGAAGTTTGTTTATAGATGGCTCTAGTTGTTAAAGGAAAAG
TGAATATCAATGAGTTTATCGACCTGACAAAAATGGAGAAGATCTTACCGTC
GATGTTTACCCCTGTAAAGAGTGTTATGTGTTCCAAAGTTGATAAAATAATGG
TTCATGAGAATGAGTCATTGTCAGGGGTGAACCTTCTTAAAGGAGTTAAGCTT
ATTGATAGTGGATACGTCTGTTTAGCCGGTTTGGTCGTCACGGGCGAGTGGA
ACTTGCCTGACAATTGCAGAGGAGGTGTGAGCGTGTGTCTGGTGGACAAAAG
GATGGAAAGAGCCGACGAGGCCATTCTCGGATCTTACTACACAGCAGCTGCA
AAGAAAAGATTTCAGTTCAAGGTCGTTCCCAATTATGCTATAACCACCCAGG
ACGCGATGAAAAACGTCTGGCAAGTTTTAGTTAATATTAGAAATGTGAAGAT
GTCAGCGGGTTTCTGTCCGCTTTCTCTGGAGTTTGTGTCGGTGTGTATTGTTTA
TAGAAATAATATAAAATTAGGTTTGAGAGAGAAGATTACAAACGTGAGAGA
CGGAGGGCCCATGGAACTTACAGAAGAAGTCGTTGATGAGTTCATGGAAGAT
GTCCCTATGTCGATCAGGCTTGCAAAGTTTCGATCTCGAACCGGAAAAAAGA
GTGATGTCCGCAAAGGGAAAAATAGTAGTAGTGATCGGTCAGTGCCGAACAA
GAACTATAGAAATGTTAAGGATTTTGGGGGAATGAGTTTTAAAAAGAATAAT
TTAATCGATGATGATTCGGAGGCTACTGTCGCCGAATCGGATTCGTTTTAAAT
AGATCTTACAGTATCACTACTCCATCTCAGTTCGTGTTCTTGTCATTAATTAAA
TGGCTAGCAAAGGAGAAGAACTTTTCACTGGAGTTGTCCCAATTCTTGTTGAA
TTAGATGGTGATGTTAATGGGCACAAATTTCTGTCAGTGGAGAGGGTGAAG
GTGATGCTACATACGGAAAGCTTACACTTAAATTTATTTGCACTACTGGAAAA
CTACCTGTTCCATGGCCAACACTTGTCACTACTTTCTCTTATGGTGTTCAATGC
TTTTCCCGTTATCCGGATCATATGAAACGGCATGACTTTTTCAAGAGTGCCAT
GCCCGAAGGTTATGTACAGGAACGCACTATATCTTTCAAAGATGACGGGAAC
TACAAGACGCGTGCTGAAGTCAAGTTTGAAGGTGATACCCTTGTTAATCGTAT
CGAGTTAAAAGGTATTGATTTTAAAGAAGATGGAAACATTCTCGGACACAAA
CTCGAGTACAACTATAACTCACACAATGTATACATCACGGCAGACAAACAAA
AGAATGGAATCAAAGCTAACTTCAAAATTCGCCACAACATTGAAGATGGATC
CGTTCAACTAGCAGACCATTATCAACAAATACTCCAATTGGCGATGGCCCT
GTCCTTTTACCAGACAACCATTACCTGTCGACACAATCTGCCCTTTCGAAAGA
TCCCAACGAAAAGCGTGACCACATGGTCCTTCTTGAGTTTGTAACTGCTGCTG
GGATTACACATGGCATGGATGAGCTCTACAAATAATGACACTCGAGGGGTAG
TCAAGATGCATAATAAATAACGGATTGTGTCCGTAATCACACGTGGTGCGTA
CGATAACGCATAGTGTTTTTCCCTCCACTTAAATCGAAGGGTTGTGTCTTGGA
TCGCGCGGGTCAAATGTATATGGTTCATATACATCCGCAGGCACGTAATAAA
GCGAGGGGTTCGGGTCGAGGTCGGCTGTGAAACTCGAAAAGGTTCCGGAAA
ACAAAAAAGAGAGTGGTAGGTAATAGTGTTAATAATAAGAAAATAAATAAT
AGTGGTAAGAAAGGTTTGAAAGTTGAGGAAATTGAGGATAATGTAAGTGATG
ACGAGTCTATCGCGTCATCGAGTACGTTTTAATCAATATGCCTTATACAATCA
ACTCTCCGAGCCAATTTGTTTACTTAAGTTCCGCTTATGCAGATCCTGTGCAG
CTGATCAATCTGTGTACAAATGCATTGGGTAACCAGTTTCAAACGCAACAAG
CTAGGACAACAGTCCAACAGCAATTTGCGGATGCCTGGAAACCTGTGCCTAG
TATGACAGTGAGATTTCCTGCATCGGATTTCTATGTGTATAGATATAATTCGA
CGCTTGATCCGTTGATCACGGCGTTATTAAATAGCTTCGATACTAGAAATAGA
```

FIG 2-3

```
ATAATAGAGGTTGATAATCAACCCGCACCGAATACTACTGAAATCGTTAACG
CGACTCAGAGGGTAGACGATGCGACTGTAGCTATAAGGGCTTCAATCAATAA
TTTGGCTAATGAACTGGTTCGTGGAACTGGCATGTTCAATCAAGCAAGCTTTG
AGACTGCTAGTGGACTTGTCTGGACCACAACTCCGGCTACTTAGCTATTGTTG
TGAGATTTCCTAAAATAAAGTCACTGAAGACTTAAAATTCAGGGTGGCTGAT
ACCAAAATCAGCAGTGGTTGTTCGTCCACTTAAATATAACGATTGTCATATCT
GGATCCAACAGTTAAACCATGTGATGGTGTATACTGTGGTATGGCGTAAAAC
AACGGAAAAGTCGCTGAAGACTTAAAATTCAGGGTGGCTGATACCAAAATCA
GCAGTGGTTGTTCGTCCACTTAAAAATAACGATTGTCATATCTGGATCCAACA
GTTAAACCATGTGATGGTGTATACTGTGGTATGGCGTAAAACAACGGAGAGG
TTCGAATCCTCCCCTAACCGCGGGTAGCGGCCCA
```

FIG 2-4

SBS60-29

```
GGTATTTTTACAACAATTACCAACAACAACAAACAACAGACAACATTACAAT
TACTATTTACAATTACAATGGCATACACACAGACAGCTACCACATCAGCTTTG
CTGGACACTGTCCGAGGAAACAACTCCTTGGTCAATGATCTAGCAAAGCGTC
GTCTTTACGACACAGCGGTTGAAGAGTTTAACGCTCGTGACCGCAGGCCCAA
GGTGAACTTTTCAAAAGTAATAAGCGAGGAGCAGACGCTTATTGCTACCCGG
GCGTATCCAGAATTCCAAATTACATTTTATAACACGCAAAATGCCGTGCATTC
GCTTGCAGGTGGATTGCGATCTTTAGAACTGGAATATCTGATGATGCAAATTC
CCTACGGATCATTGACTTATGACATAGGCGGGAATTTTGCATCGCATCTGTTC
AAGGGACGAGCATATGTACACTGCTGCATGCCCAACCTGGACGTTCGAGACA
TCATGCGGCACGAAGGCCAGAAAGACAGTATTGAACTATACCTTTCTAGGCT
AGAGAGAGGGGGGAAAACAGTCCCCAACTTCCAAAAGGAAGCATTTGACAG
ATACGCAGAAATTCCTGAAGACGCTGTCTGTCACAATACTTTCCAGACATGC
GAACATCAGCCGATGCAGCAATCAGGCAGAGTGTATGCCATTGCGCTACACA
GCATATATGACATACCAGCCGATGAGTTCGGGGCGGCACTCTTGAGGAAAAA
TGTCCATACGTGCTATGCCGCTTTCCACTTCTCCGAGAACCTGCTTCTTGAAG
ATTCATGCGTCAATTTGGACGAAATCAACGCGTGTTTTCGCGCGATGGAGAC
AAGTTGACCTTTTCTTTTGCATCAGAGAGTACTCTTAATTACTGTCATAGTTAT
TCTAATATTCTTAAGTATGTGTGCAAAACTTACTTCCCGGCCTCTAATAGAGA
GGTTTACATGAAGGAGTTTTAGTCACCAGAGTTAATACCTGGTTTTGTAAGT
TTTCTAGAATAGATACTTTTCTTTTGTACAAAGGTGTGGCCCATAAAAGTGTA
GATAGTGAGCAGTTTTATACTGCAATGGAAGACGCATGGCATTACAAAAAGA
CTCTTGCAATGTGCAACAGCGAGAGAATCCTCCTTGAGGATTCATCATCAGTC
AATTACTGGTTTCCCAAAATGAGGGATATGGTCATCGTACCATTATTCGACAT
TTCTTTGGAGACTAGTAAGAGGACGCGCAAGGAAGTCTTAGTGTCCAAGGAT
TTCGTGTTCACAGTGCTTAACCACATTCGAACATACCAGGCGAAAGCTCTTAC
ATACGCAAATGTTTTGTCCTTCGTCGAATCGATTCGATCGAGGGTAATCATTA
ACGGTGTGACAGCGAGGTCCGAATGGGATGTGGACAAATCTTTGTTACAATC
CTTGTCCATGACGTTTTACCTGCATACTAAGCTTGCCGTTCTAAAGGATGACT
TACTGATTAGCAAGTTTAGTCTCGGTTCGAAAACGGTGTGCCAGCATGTGTGG
GATGAGATTTCGCTGGCGTTTGGGAACGCATTTCCCTCCGTGAAAGAGAGGC
TCTTGAACAGGAAACTTATCAGAGTGGCAGGCGACGCATTAGAGATCAGGGT
GCCTGATCTATATGTGACCTTCCACGACAGATTAGTGACTGAGTACAAGGCCT
CTGTGGACATGCCTGCGCTTGACATTAGGAAGAAGATGGAAGAAACGGAAGT
GATGTACAATGCACTTTCAGAATTATCGGTGTTAAGGGAGTCTGACAAATTC
GATGTTGATGTTTTTCCCAGATGTGCCAATCTTTGGAAGTTGACCCAATGAC
GGCAGCGAAGGTTATAGTCGCGGTCATGAGCAATGAGAGCGGTCTGACTCTC
ACATTTGAACGACCTACTGAGGCGAATGTTGCGCTAGCTTTACAGGATCAAG
AGAAGGCTTCAGAAGGTGCATTGGTAGTTACCTCAAGAGAAGTTGAAGAACC
GTCCATGAAGGGTTCGATGGCCAGAGGAGAGTTACAATTAGCTGGTCTTGCT
GGAGATCATCCGGAATCGTCCTATTCTAAGAACGAGGAGATAGAGTCTTTAG
AGCAGTTTCATATGGCGACGGCAGATTCGTTAATTCGTAAGCAGATGAGCTC
GATTGTGTACACGGGTCCGATTAAAGTTCAGCAAATGAAAAACTTTATCGAT
AGCCTGGTAGCATCACTATCTGCTGCGGTGTCGAATCTCGTCAAGATCCTCAA
AGATACAGCTGCTATTGACCTTGAAACCCGTCAAAAGTTTGGAGTCTTGGAT
```

FIG 3-1

```
GTTGCATCTAGGAAGTGGTTAATCAAACCAACGGCCAAGAGTCATGCATGGG
GTGTTGTTGAAACCCACGCGAGGAAGTATCATGTGGCGCTTTTGGAATATGA
TGAGCAGGGTGTGGTGACATGCGATGATTGGAGAAGAGTAGCTGTTAGCTCT
GAGTCTGTTGTTTATTCCGACATGGCGAAACTCAGAACTCTGCGCAGACTGCT
TCGAAACGGAGAACCGCATGTCAGTAGCGCAAAGGTTGTTCTTGTGGACGGA
GTTCCGGGCTGTGGAAAAACCAAAGAAATTCTTTCCAGGGTTAATTTTGATG
AAGATCTAATTTTAGTACCTGGGAAGCAAGCCGCGGAAATGATCAGAAGACG
TGCGAATTCCTCAGGGATTATTGTGGCCACGAAGGACAACGTTAAACCGTT
GATTCTTTCATGATGAATTTTGGGAAAAGCACACGCTGTCAGTTCAAGAGGTT
ATTCATTGATGAAGGGTTGATGTTGCATACTGGTTGTGTTAATTTTCTTGTGG
CGATGTCATTGTGCGAAATTGCATATGTTACGGAGACACACAGCAGATTC
CATACATCAATAGAGTTTCAGGATTCCCGTACCCCGCCCATTTTGCCAAATTG
GAAGTTGACGAGGTGGAGACACGCAGAACTACTCTCCGTTGTCCAGCCGATG
TCACACATTATCTGAACAGGAGATATGAGGGCTTTGTCATGAGCACTTCTTCG
GTTAAAAAGTCTGTTTCGCAGGAGATGGTCGGCGGAGCCGCCGTGATCAATC
CGATCTCAAAACCCTTGCATGGCAAGATCCTGACTTTTACCCAATCGGATAAA
GAAGCTCTGCTTTCAAGAGGGTATTCAGATGTTCACACTGTGCATGAAGTGC
AAGGCGAGACATACTCTGATGTTTCACTAGTTAGGTTAACCCCTACACCGGTC
TCCATCATTGCAGGAGACAGCCCACATGTTTTGGTCGCATTGTCAAGGCACAC
CTGTTCGCTCAAGTACTACACTGTTGTTATGGATCCTTTAGTTAGTATCATTAG
AGATCTAGAGAAACTTAGCTCGTACTTGTTAGATATGTATAAGGTCGATGCA
GGAACACAATAGCAATTACAGATTGACTCGGTGTTCAAAGGTTCCAATCTTTT
TGTTGCAGCGCCAAAGACTGGTGATATTTCTGATATGCAGTTTTACTATGATA
AGTGTCTCCCAGGCAACAGCACCATGATGAATAATTTTGATGCTGTTACCATG
AGGTTGACTGACATTTCATTGAATGTCAAAGATTGCATATTGGATATGTCTAA
GTCTGTTGCTGCGCCTAAGGATCAAATCAAACCACTAATACCTATGGTACGA
ACGGCGGCAGAAATGCCACGCCAGACTGGACTATTGGAAAATTTAGTGGCGA
TGATTAAAAGAAACTTTAACGCACCCGAGTTGTCTGGCATCATTGATATTGAA
AATACTGCATCTTTGGTTGTAGATAAGTTTTTTGATAGTTATTTGCTTAAAGA
AAAAAGAAAACCAAATAAAAATGTTTCTTTGTTCAGTAGAGAGTCTCTCAAT
AGATGGTTAGAAAAGCAGGAACAGGTAACAATAGGCCAGCTCGCAGATTTTG
ATTTTGTGGATTTGCCAGCAGTTGATCAGTACAGACACATGATTAAAGCACA
ACCCAAACAAAAGTTGGACACTTCAATCCAAACGGAGTACCCGGCTTTGCAG
ACGATTGTGTACCATTCAAAAAAGATCAATGCAATATTCGGCCCGTTGTTTAG
TGAGCTTACCAGGCAATTACTGGACAGTGTTGATTCGAGCAGATTTTGTTTT
TCACAAGAAAGACACCAGCGCAGATTGAGGATTTCTTCGGAGATCTCGACAG
TCATGTGCCGATGGATGTCTTGGAGCTGGATATATCAAAATACGACAAATCT
CAGAATGAATTCCACTGTGCAGTAGAATACGAGATCTGGCGAAGATTGGGTT
TCGAAGACTTCTTGGGAGAAGTTTGGAAACAAGGGCATAGAAAGACCACCCT
CAAGGATTATACCGCAGGTATAAAAACTTGCATCTGGTATCAAAGAAAGAGC
GGGGACGTCACGACGTTCATTGGAAACACTGTGATCATTGCTGCATGTTTGGC
CTCGATGCTTCCGATGGAGAAAATAATCAAAGGAGCCTTTTGCGGTGACGAT
AGTCTGCTGTACTTTCCAAAGGGTTGTGAGTTTCCGGATGTGCAACACTCCG
CGAATCTTATGTGGAATTTTGAAGCAAAACTGTTTAAAAAACAGTATGGATA
CTTTTGCGGAAGATATGTAATACATCACGACAGAGGATGCATTGTGTATTAC
GATCCCCTAAAGTTGATCTCGAAACTTGGTGCTAAACACATCAAGGATTGGG
```

FIG 3-2

```
AACACTTGGAGGAGTTCAGAAGGTCTCTTTGTGATGTTGCTGTTTCGTTGAAC
AATTGTGCGTATTACACACAGTTGGACGACGCTGTATGGGAGGTTCATAAGA
CCGCCCCTCCAGGTTCGTTTGTTTATAAAAGTCTGGTGAAGTATTTGTCTGAT
AAAGTTCTTTTTAGAAGTTTGTTTATAGATGGCTCTAGTTGTTAAAGGAAAAG
TGAATATCAATGAGTTTATCGACCTGACAAAATGGAGAAGATCTTACCGTC
GATGTTTACCCCTGTAAAGAGTGTTATGTGTTCCAAAGTTGATAAAATAATGG
TTCATGAGAATGAGTCATTGTCAGGGGTGAACCTTCTTAAAGGAGTTAAGCTT
ATTGATAGTGGATACGTCTGTTTAGCCGGTTTGGTCGTCACGGGCGAGTGGA
ACTTGCCTGACAATTGCAGAGGAGGTGTGAGCGTGTGTCTGGTGGACAAAAG
GATGGAAAGAGCCGACGAGGCCATTCTCGGATCTTACTACACAGCAGCTGCA
AAGAAAAGATTTCAGTTCAAGGTCGTTCCCAATTATGCTATAACCACCCAGG
ACGCGATGAAAAACGTCTGGCAAGTTTTAGTTAATATTAGAAATGTGAAGAT
GTCAGCGGGTTTCTGTCCGCTTTCTCTGGAGTTTGTGTCGGTGTGTATTGTTTA
TAGAAATAATATAAAATTAGGTTTGAGAGAGAAGATTACAAACGTGAGAGA
CGGAGGGCCCATGGAACTTACAGAAGAAGTCGTTGATGAGTTCATGGAAGAT
GTCCCTATGTCGATCAGGCTTGCAAAGTTCGATCTCGAACCGGAAAAAGA
GTGATGTCCGCAAAGGGAAAAATAGTAGTAGTGATCGGTCAGTGCCAACAA
GAACTATAGAAATGTTAAGGATTTTGGGGGAATGAGTTTTAAAAAGAATAAT
TTAATCGATGATGATTCGGAGGCTACTGTCGCCGAATCGGATTCGTTTTAAAT
AGATCTTACAGTATCACTACTCCATCTCAGTTCGTGTTCTTGTCATTAATTAAA
TGGCTAGCAAAGGAGAAGAACTTTTCACTGGAGTTGTCCCAATTCTTGTTGAA
TTAGATGGTGATGTTAATGGGCACAAATTTTCTGTCAGTGGAGAGGGTGAAG
GTGATGCTACATACGGAAAGCTTACACTTAAATTTATTTGCACTACTGGAAAA
CTACCTGTTCCATGGCCAACACTTGTCACTACTTTCTCTTATGGTGTTCAATGC
TTTTCCCGTTATCCGGATCATATGAAACGGCATGACTTTTTCAAGAGTGCCAT
GCCCGAAGGTTATGTACAGGAACGCACTATATCTTTCAAAGATGACGGGAAC
TACAAGACGCGTGCTGAAGTCAAGTTTGAAGGTGATACCCTTGTTAATCGTAT
CGAGTTAAAAGGTATTGATTTTAAAGAAGATGGAAACATTCTCGGACACAAA
CTCGAGTACAACTATAACTCACACAATGTATACATCACGGCAGACAAACAAA
AGAATGGAATCAAAGCTAACTTCAAAATTCGCCACAACATTGAAGATGGATC
CGTTCAACTAGCAGACCATTATCAACAAAATACTCCAATTGGCGATGGCCCT
GTCCTTTTACCAGACAACCATTACCTGTCGACACAATCTGCCCTTTCGAAAGA
TCCCAACGAAAAGCGTGACCACATGGTCCTTCTTGAGTTTGTAACTGCTGCTG
GGATTACACATGGCATGGATGAGCTCTACAAATAATGACACTCGAGGGGTAG
TCAAGATGCATAATAAATAACGGATTGTGTCCGTAATCACACGTGGTGCGTA
CGATAACGCATAGTGTTTTTCCCTCCACTTAAATCGAAGGGTTGTGTCTTGGA
TCGCGCGGGTCAAATGTATATGGTTCATATACATCCGCAGGCACGTAATAAA
GCGAGGGGTTCGGGTCGAGGTCGGCTGTGAAACTCGAAAAGGTTCCGGAAA
ACAAAAAGAGAGTGGTAGGTAATAGTGTTAATAATAAGAAAATAAATAAT
AGTGGTAAGAAAGGTTTGAAAGTTGAGGAAATTGAGGATAATGTAAGTGATG
ACGAGTCTATCGCGTCATCGAGTACGTTTAATCAATATGCCTTATACAATCA
ACTCTCCGAGCCAATTTGTTTACTTAAGTTCCGCTTATGCAGATCCTGTGCAG
CTGATCAATCTGTGTACAAATGCATTGGGTAACCAGTTTCAAACGCAACAAG
CTAGGACAACAGTCCAACAGCAATTTGCGGATGCCTGGAAACCTGTGCCTAG
TATGACAGTGAGATTTCCTGCATCGGATTTCTATGTGTATAGATATAATTCGA
CGCTTGATCCGTTGATCACGGCGTTATTAAATAGCTTCGATACTAGAAATAGA
```

FIG 3-3

```
ATAATAGAGGTTGATAATCAACCCGCACCGAATACTACTGAAATCGTTAACG
CGACTCAGAGGGTAGACGATGCGACTGTAGCTATAAGGGCTTCAATCAATAA
TTTGGCTAATGAACTGGTTCGTGGAACTGGCATGTTCAATCAAGCAAGCTTTG
AGACTGCTAGTGGACTTGTCTGGACCACAACTCCGGCTACTTAGCTATTGTTG
TGAGATTTCCTAAAATAAAGTCACTGAAGACTTAAAATTCAGGGTGGCTGAT
ACCAAAATCAGCAGTGGTTGTTCGTCCACTTAAATATAACGATTGTCATATCT
GGATCCAACAGTTAAACCATGTGATGGTGTATACTGTGGTATGGCGTAAAAC
AACGGAAAGTCGCTGAAGACTTAAAATTCAGGGTGGCTGATACCAAAATCA
GCAGTGGTTGTTCGTCCACTTAAAAATAACGATTGTCATATCTGGATCCAACA
GTTAAACCATGTGATGGTGTATACTGTGGTATGGCGTAAAACAACGGAGAGG
TTCGAATCCTCCCCTAACCGCGGGTAGC
GGCCCA
```

```
GTATTTTTACAACAATTACCAACAACAACAAACAACAGACAACATTACAATT
ACTATTTACAATTACAATGGCATACACACAGACAGCTACCACATCAGCTTTGC
TGGACACTGTCCGAGGAAACAACTCCTTGGTCAATGATCTAGCAAAGCGTCG
TCTTTACGACACAGCGGTTGAAGAGTTTAACGCTCGTGACCGCAGGCCCAAG
GTGAACTTTTCAAAAGTAATAAGCGAGGAGCAGACGCTTATTGCTACCCGGG
CGTATCCAGAATTCCAAATTACATTTTATAACACGCAAAATGCCGTGCATTCG
CTTGCAGGTGGATTGCGATCTTTAgAACTGGAATATCTGATGATGCAAATTCC
CTACGGATCATTGACTTATGACATAGGCGGGAATTTTGCATCGCATCTGTTCA
AGGGACGAGCATATGTACACTGCTGCATGCCCAACCTGGACGTTCGAGACAT
CATGCGGCACGAAGGCCAGAAAGACAGTATTGAACTATACCTTTCTAGGCTA
GAGAGAGGGGGGAAAACAGTCCCCAACTTCCAAAAGGAAGCATTTGACAGA
TACGCAGAAATTCCTGAAGACGCTGTCTGTCACAATACTTTCCAGACATGCG
AACATCAGCCGATGCAGCAATCAGGCAGAGTGTATGCCATTGCGCTACACAG
CATATATGACATACCAGCCGATGAGTTCGGGGCGGCACTCTTGAGGAAAAAT
GTCCATACGTGCTATGCCGCTTTCCACTTCTCCGAGAACCTGCTTCTTGAAGA
TTCATGCGTCAATTTGGACGAAATCAACGCGTGTTTTCGCGCGATGGAGACA
AGTTGACCTTTTCTTTTGCATCAGAGAGTACTCTTAATTACTGTCATAGTTATT
CTAATATTCTTAAGTATGTGTGCAAAACTTACTTCCCGGCCTCTAATAGAGAG
GTTTACATGAAGGAGTTTTTAGTCACCAGAGTTAATACCTGGTTTTGTAAGTT
TTCTAGAATAGATACTTTTCTTTTGTACAAAGGTGTGGCCCATAAAAGTGTAG
ATAGTGAGCAGTTTTATACTGCAATGGAAGACGCATGGCATTACAAAAAGAC
TCTTGCAATGTGCAACAGCGAGAGAATCCTCCTTGAGGATTCATCATCAGTCA
ATTACTGGTTTCCCAAAATGAGGGATATGGTCATCGTACCATTATTCGACATT
TCTTTGGAGACTAGTAAGAGGACGCGCAAGGAAGTCTTAGTGTCCAAGGATT
TCGTGTTTACAGTGCTTAACCACATTCGAACATACCAGGCGAAAGCTCTTACA
TACGCAAATGTTTTGTCCTTCGTCGAATCGATTCGATCGAGGGTAATCATTAA
CGGTGTGACAGCGAGGTCCGAATGGGATGTGGACAAATCTTTGTTACAATCC
TTGTCCATGACGTTTTACCTGCATACTAAGCTTGCCGTTCTAAAGGATGACTT
ACTGATTAGCAAGTTTAGTCTCGGTTCGAAAACGGTGTGCCAGCATGTGTGG
GATGAGATTTCGCTGGCGTTTGGGAACGCATTTCCCTCCGTGAAAGAGAGGC
TCTTGAACAGGAAACTTATCAGAGTGGCAGGCGACGCATTAGAGATCAGGGT
GCCTGATCTATATGTGACCTTCCACGACAGATTAGTGACTGAGTACAAGGCCT
CTGTGGACATGCCTGCGCTTGACATTAGGAAGAAGATGGAAGAAACGGAAGT
GATGTACAATGCACTTTCAGAATTATCGGTGTTAAGGGAGTCTGACAAATTC
GATGTTGATGTTTTTCCCAGATGTGCCAATCTTTGGAAGTTGACCCAATGAC
GGCAGCGAAGGTTATAGTCGCGGTCATGAGCAATGAGAGCGGTCTGACTCTC
ACATTTGAACGACCTACTGAGGCGAATGTTGCGCTAGCTTTACAGGATCAAG
AGAAGGCTTCAGAAGGTGCATTGGTAGTTACCTCAAGAGAAGTTGAAGAACC
GTCCATGAAGGGTTCGATGGCCAGAGGAGAGTTACAATTAGCTGGTCTTGCT
GGAGATCATCCGGAATCGTCCTATTCTAAGAACGAGGAGATAGAGTCTTTAG
AGCAGTTTCATATGGCGACGGCAGATTCGTTAATTCGTAAGCAGATGAGCTC
GATTGTGTACACGGGTCCGATTAAAGTTCAGCAAATGAAAAACTTTATCGAT
AGCCTGGTAGCATCACTATCTGCTGCGGTGTCGAATCTCGTCAAGATCCTCAA
AGATACAGCTGCTATTGACCTTGAAACCCGTCAAAAGTTTGGAGTCTTGGAT
```

FIG 4-1

GTTGCATCTAGGAAGTGGTTAATCAAACCAACGGCCAAGAGTCATGCATGGG
GTGTTGTTGAAACCCACGCGAGGAAGTATCATGTGGCGCTTTTGGAATATGA
TGAGCAGGGTGTGGTGACATGCGATGATTGGAGAAGAGTAGCTGTTAGCTCT
GAGTCTGTTGTTTATTCCGACATGGCGAAACTCAGAACTCTGCGCAGACTGCT
TCGAAACGGAGAACCGCATGTCAGTAGCGCAAAGGTTGTTCTTGTGGACGGA
GTTCCGGGCTGTGGAAAAACCAAAGAAATTCTTTCCAGGGTTAATTTTGATG
AAGATCTAATTTTAGTACCTGGGAAGCAAGCCGCGGAAATGATCAGAAGACG
TGCGAATTCCTCAGGGATTATTGTGGCCACGAAGGACAACGTTAAAACCGTT
GATTCTTTCATGATGAATTTTGGGAAAAGCACACGCTGTCAGTTCAAGAGGTT
ATTCATTGATGAAGGGTTGATGTTGCATACTGGTTGTGTTAATTTTCTTGTGG
CGATGTCATTGTGCGAAATTGCATATGTTTACGGAGACACACAGCAGATTCC
ATACATCAATAGAGTTTCAGGATTCCCGTACCCCGCCCATTTTGCCAAATTGG
AAGTTGACGAGGTGGAGACACGCAGAACTACTCTCCGTTGTCCAGCCGATGT
CACACATTATCTGAACAGGAGATATGAGGGCTTTGTCATGAGCACTTCTTCGG
TTAAAAAGTCTGTTTCGCAGGAGATGGTCGGCGGAGCCgCCGTGATCAATCC
ATCTCAAAACCCTTGCATGGCAAGATCTTGACTTTTACCCAATCGGATAAAGA
AGCTCTGCTTTCAAGAGGGTATTCAGATGTTCACACTGTGCATGAAGTGCAA
GGCGAGACATACTCTGATGTTTCACTAGTTAGGTTAACCCCTACACCGGTCTC
CATCATTGCAGGAGACAGCCCACATGTTTGGTCGCATTGTCAAGGCACACCT
GTTCGCTCAAGTACTACACTGTTGTTATGGATCCTTTAGTTAGTATCATTAGA
GATCTAGAGAAACTTAGCTCGTACTTGTTAGATATGTATAAGGTCGATGCAG
GAACACAATAGCAATTACAGATTGACTCGGTGTTCAAAGGTTCCAATCTTTTT
GTTGCAGCGCCAAAGACTGGTGATATTTCTGATATGCAGTTTTACTATGATAA
GTGTCTCCCAGGCAACAGCACCATGATGAATAATTTTGATGCTGTTACCATGA
GGTTGACTGACATTTCATTGAATGTCAAAGATTGCATATTGGATATGTCTAAG
TCTGTTGCTGCGCCTAAGGATCAAATCAAACCACTAATACCTATGGTACGAA
CGGCGGCAGAAATGCCACGCCAGACTGGACTATTGGAAAATTTAGTGGCGAT
GATTAAAAGAAACTTTAACGCACCCGAGTTGTCTGGCATCATTGATATTGAA
AATACTGCATCTTTGGTTGTAGATAAGTTTTTTGATAGTTATTTGCTTAAAGA
AAAAAGAAAACCAAATAAAAATGTTTCTTTGTTCAGTAGAGAGTCTCTCAAT
AGATGGTTAGAAAAGCAGGAACAGGTAACAATAGGCCAGCTCGCAGATTTTG
ATTTTGTGGATTTGCCAGCAGTTGATCAGTACAGACACATGATTAAAGCACA
ACCCAAACAAAAGTTGGACACTTCAATCCAAACGGAGTACCCGGCTTTGCAG
ACGATTGTGTACCATTCAAAAAAGATCAATGCAATATTCGGCCCGTTGTTTAG
TGAGCTTACTAGGCAATTACTGGACAGTGTTGATTCGAGCAGATTTTTGTTTT
TCACAAGAAAGACACCAGCGCAGATTGAGGATTTCTTCGGAGATCTCGACAG
TCATGTGCCGATGGATGTCTTGGAGCTGGATATATCAAAATACGACAAATCT
CAGAATGAATTCCACTGTGCAGTAGAATACGAGATCTGGCGAAGATTGGGTT
TCGAAGACTTCTTGGGAGAAGTTTGGAAACAAGGGCATAGAAAGACCACCCT
CAAGGATTATACCGCAGGTATAAAAACTTGCATCTGGTATCAAAGAAAGAGC
GGGGACGTCACGACGTTCATTGGAAACACTGTGATCATTGCTGCATGTTTGGC
CTCGATGCTTCCGATGGAGAAAATAATCAAAGGAGCCTTTTGCGGTGACGAT
AGTCTGCTGTACTTTCCAAAGGGTTGTGAGTTTCCGGATGTGCAACACTCCG
CGAATCTTATGTGGAATTTTGAAGCAAAACTGTTTAAAAAACAGTATGGATA
CTTTTGCGGAAGATATGTAATACATCACGACAGAGGATGCATTGTGTATTAC
GATCCCCTAAAGTTGATCTCGAAACTTGGTGCTAAACACATCAAGGATTGGG

FIG 4-2

```
AACACTTGGAGGAGTTCAGAAGGTCTCTTTGTGATGTTGCTGTTTCGTTGAAC
AATTGTGCGTATTACACACAGTTGGACGACGCTGTATGGGAGGTTCATAAGA
CCGCCCCTCCAGGTTCGTTTGTTTATAAAAGTCTGGTGAAGTATTTGTCTGAT
AAAGTTCTTTTTAGAAGTTTGTTTATAGATGGCTCTAGTTGTTAAAGGAAAAG
TGAATATCAATGAGTTTATCGACCTGACAAAAATGGAGAAGATCTTACCGTC
GATGTTTACCCCTGTAAAGAGTGTTATGTGTTCCAAAGTTGATAAATAATGG
TTCATGAGAATGAGTCATTGTCAGGGGTGAACCTTCTTAAAGGAGTTAAGCTT
ATTGATAGTGGATACGTCTGTTTAGCCGGTTTGGTCGTCACGGGCGAGTGGA
ACTTGCCTGACAATTGCAGAGGAGGTGTGAGCGTGTGTCTGGTGGACAAAAG
GATGGAAAGAGCCGACGAGGCCATTCTCGGATCTTACTACACAGCAGCTGCA
AAGAAAAGATTTCAGTTCAAGGTCGTTCCCAATTATGCTATAACCACCCAGG
ACGCGATGAAAAACGTCTGGCAAGTTTTAGTTAATATTAGAAATGTGAAGAT
GTCAGCGGGTTTCTGTCCGCTTTCTCTGGAGTTTGTGTCGGTGTGTATTGTTTA
TAAAAATAATATAAAATTAGGTTTGAGAGAGAAGATTACAAACGTGAGAGA
CGGAGGGCCCATGGAACTTACAGAAGAAGTCGTTGATGAGTTCATGGAAGAT
GTCCCTATGTCGATCAGGCTTGCAAAGTTTCGATCTCGAACCGGAAAAAGA
GTGATGTCCGCAAAGGGAAAAATAGTAGTAGTGATCGGTCAGTGCCGAACAA
GAACTATAGAAATGTTAAGGATTTTGGAGGAATGAGTTTTAAAAAGAATAAT
TTAATCGATGATGATTCGGAGGCTACTGTCGCCGAATCGGATTCGTTTTAAAT
AGATCTTACAGTATCACTACTCCATCTCAGTTCGTGTTCTTGTCATTAATTAAA
TGGCTAGCAAAGGAGAAGAACTTTTCACTGGAGTTGTCCCAATTCTTGTTGAA
TTAGATGGTGATGTTAATGGGCACAAATTTCTGTCAGTGGAGAGGGTGAAG
GTGATGCTACATACGGAAAGCTTACCCTTAAATTTATTTGCACTACTGGAAAA
CTACCTGTTCCATGGCCAACACTTGTCACTACTTTCTCTTATGGTGTTCAATGC
TTTTCCCGTTATCCGGATCATATGAAACGGCATGACTTTTCAAGAGTGCCAT
GCCCGAAGGTTATGTACAGGAACGCACTATATCTTTCAAAGATGACGGGAAC
TACAAGACGCGTGCTGAAGTCAAGTTTGAAGGTGATACCCTTGTTAATCGTAT
CGAGTTAAAAGGTATTGATTTTAAAGAAGATGGAAACATTCTCGGACACAAA
CTCGAGTACAACTATAACTCACACAATGTATACATCACGGCAGACAAACAAA
AGAATGGAATCAAAGCTAACTTCAAAATTCGCCACAACATTGAAGATGGATC
CGTTCAACTAGCAGACCATTATCAACAAAATACTCCAATTGGCGATGGCCCT
GTCCTTTTACCAGACAACCATTACCTGTCGACACAATCTGCCCTTTCGAAAGA
TCCCAACGAAAAGCGTGACCACATGGGCCTTCTTGAGTTTGTAACTGCTGCTG
GGATTACACATGGCATGGATGAGCTCTACAAATAATGACACTCGAGGGGTAG
TCAAGATGCATAATAAATAACGGATTGTGTCCGTAATCACACGTGGTGCGTA
CGATAACGCATAGTGTTTTTCCCTCCACTTAAATCGAAGGGTTGTGTCTTGGA
TCGCGCGGGTCAAATGTATATGGTTCATATACATCCGCAGGCACGTAATAAA
GCGAGGGGTTCGGGTCGAGGTCGGCTGTGAAACTCGAAAAGGTTCCGGAAA
ACAAAAAGAGAGTGGTAGGTAATAGTGTTAATAATAAGAAAATAAATAAT
AGTGGTAAGAAAGGTTTGAAAGTTGAGGAAATTGAGGATAATGTAAGTGATG
ACGAGTCTATCGCGTCATCGAGTACGTTTTAATCAATATGCCTTATACAATCA
ACTCTCCGAGCCAATTTGTTTACTTAAGTTCCGCTTATGCAGATCCTGTGCAG
CTGATCAATCTGTGTACAAATGCATTGGGTAACCAGTTTCAAACGCAACAAG
CTAGGACAACAGTCCAACAGCAATTTGCGGATGCCTGGAAACCTGTGCCTAG
TATGACAGTGAGATTTCCTGCATCGGATTTCTATGTGTATAGATATAATTCGA
CGCTTGATCCGTTGATCACGGCGTTATTAAATAGCTTCGATACTAGAAATAGA
```

FIG 4-3

ATAATAGAGGTTGATAATCAACCCGCACCGAATACTACTGAAATCGTTAACG
CGACTCAGAGGGTAGACGATGCGACTGTAGCTATAAGGGCTTCAATCAATAA
TTTGGCTAATGAACTGGTTCGTGGAACTGGCATGTTCAATCAAGCAAGCTTTG
AGACTGCTAGTGGACTTGTCTGGACCACAACTCCGGCTACTTAGCTATTGTTG
TGAGATTTCCTAAAATAAAGTCACTGAAGACTTAAAATTCAGGGTGGCTGAT
ACCAAAATCAGCAGTGGTTGTTCGTCCACTTAAATATAACGATTGTCATATCT
GGATCCAACAGTTAAACCATGTGATGGTGTATACTGTGGTATGGCGTAAAAC
AACGGAAAAGTCGCTGAAGACTTAAAATTCAGGGTGGCTGATACCAAAATCA
GCAGTGGTTGTTCGTCCACTTAAAAATAACGATTGTCATATCTGGATCCAACA
GTTAAACCATGTGATGGTGTATACTGTGGTATGGCGTAAACAACGGAGAGGT
TCGAATCCTCCCCTAACCGCGGgtagcggccca

FIG 4-4

P1057
SBS-5

```
GTATTTTTACAACAATTACCAACAACAACAAACAACAGACAACATTACAATT
ACTATTTACAATTACAATGGCATACACACAGACAGCTACCACATCAGCTTTGC
TGGACACTGTCCGAGGAAACAACTCCTTGGTCAATGATCTAGCAAAGCGTCG
TCTTTACGACACAGCGGTTGAAGAGTTTAACGCTCGTGACCGCAGGCCCAAG
GTGAACTTTTCAAAAGTAATAAGCGAGGAGCAGACGCTTATTGCTACCCGGG
CGTATCCAGAATTCCAAATTACATTTTATAACACGCAAAATGCCGTGCATTCG
CTTGCAGGTGGATTGCGATCTTAGAACTGGAATATCTGATGATGCAAATTCC
CTACGGATCATTGACTTATGACATAGGCGGGAATTTTGCATCGCATCTGTTCA
AGGGACGAGCATATGTACACTGCTGCATGCCCAACCTGGACGTTCGAGACAT
CATGCGGCACGAAGGCCAGAAAGACAGTATTGAACTATACCTTTCTAGGCTA
GAGAGAGGGGGGAAAACAGTCCCCAACTTCCAAAAGGAAGCATTTGACAGA
TACGCAGAAATTCCTGAAGACGCTGTCTGTCACAATACTTTCCAGACATGCG
AACATCAGCCGATGCAGCAATCAGGCAGAGTGTATGCCATTGCGCTACACAG
CATATATGACATACCAGCCGATGAGTTCGGGGCGGCACTCTTGAGGAAAAAT
GTCCATACGTGCTATGCCGCTTTCCACTTCTCCGAGAACCTGCTTCTTGAAGA
TTCATGCGTCAATTTGGACGAAATCAACGCGTGTTTTCGCGCGATGGAGACA
AGTTGACCTTTTCTTTTGCATCAGAGAGTACTCTTAATTACTGTCATAGTTATT
CTAATATTCTTAAGTATGTGTGCAAAACTTACTTCCCGGCCTCTAATAGAGAG
GTTTACATGAAGGAGTTTTTAGTCACCAGAGTTAATACCTGGTTTGTAAGTT
TTCTAGAATAGATACTTTTCTTTTGTACAAAGGTGTGGCCCATAAAAGTGTAG
ATAGTGAGCAGTTTTATACTGCAATGGAAGACGCATGGCATTACAAAAAGAC
TCTTGCAATGTGCAACAGCGAGAGAATCCTCCTTGGGGATTCATCATCAGTCA
ATTACTGGTTTCCCAAAATGAGGGATATGGTCATCGTACCATTATTCGACATT
TCTTTGGAGACTAGTAAGAGGACGCGCAAGGAAGTCTTAGTGTCCAAGGATT
TCGTGTTCACAGTGCTTAACCACATTCGAACATACCAGGCGAAAGCTCTTACA
TACGCAAATGTTTTGTCCTTCGTCGAATCGATTCGATCGAGGGTAATCATTAA
CGGTGTGACAGCGAGGTCCGAATGGGATGTGGACAAATCTTTGTTACAATCC
TTGTCCATGACGTTTTACCTGCATACTAAGCTTGCCGTTCTAAAGGATGACTT
ACTGATTAGCAAGTTTAGTCTCGGTTCGAAAACGGTGTGCCAGCATGTGTGG
GATGAGATTTCGCTGGCGTTTGGGAACGCATTTCCTCCGTGAAAGAGAGGC
TCTTGAACAGGAAACTTATCAGAGTGGCAGGCGACGCATTAGAGATCAGGGT
GCCTGATCTATATGTGACCTTCCACGACAGATTAGTGACTGAGTACAAGGCCT
CTGTGGACATGCCTGCGCTTGACATTAGGAAGAAGATGGAAGAAACGGAAGT
GATGTACAATGCACTTTCAGAATTATCGGTGTTAAGGGAGTCTGACAAATTC
GATGTTGATGTTTTTCCCAGATGTGCCAATCTTTGGAAGTTGACCCAATGAC
GGCAGCGAAGGTTATAGTCGCGGTCATGAGCAATGAGAGCGGTCTGACTCTC
ACATTTGAACGACCTACTGAGGCGAATGTTGCGCTAGCTTTACAGGATCAAG
AGAAGGCTTCAGAAGGTGCATTGGTAGTTACCTCAAGAGAAGTTGAAGAACC
GTCCATGAAGGGTTCGATGGCCAGAGGAGAGTTACAATTAGCTGGTCTTGCT
GGAGATCATCCGGAATCGTCCTATTCTAAGAACGAGGAGATAGAGTCTTTAG
AGCAGTTTCATATGGCGACGGCAGATTCGTTAATTCGTAAGCAGATGAGCTC
GATTGTGTACACGGGTCCGATTAAAGTTCAGCAAATGAAAAACTTTATCGAT
```

FIG 5-1

```
AGCCTGGTAGCATCACTATCTGCTGCGGTGTCGAATCTCGTCAAGATCCTCAA
AGATACAGCTGCTATTGACCTTGAAACCCGTCAAAAGTTTGGAGTCTTGGAT
GTTGCATCTAGGAAGTGGTTAATCAAACCAACGGCCAAGAGTCATGCATGGG
GTGTTGTTGAAACCCACGCGAGGGAGTATCATGTGGCGCTTTTGGAATATGA
TGAGCAGGGTGTGGTGACATGCGATGATTGGAGAAGAGTAGCTGTTAGCTCT
GAGTCTGTTGTTTATTCCGACATGGCGAAACTCAGAACTCTGCGCAGACTGCT
TCGAAACGGAGAACCGCATGTCAGTAGCGCAAAGGTTGTTCTTGTGGACGGA
GTTCCGGGCTGTGGAAAAACCAAAGAAATTCTTTCCAGGGTTAATTTTGATG
AAGATCTAATTTTAGTACCTGGGAAGCAAGCCGCGGAAATGATCAGAAGACG
TGCGAATTCCTCAGGGATTATTGTGGCCACGAAGGACAACGTTAAAACCGTT
GATTCTTTCATGATGAATTTTGGGAAAAGCACACGCTGTCAGTTCAAGAGGTT
ATTCATTGATGAAGGGTTGATGTTGCATACTGGTTGTGTTAATTTTCTTGTGG
CGATGTCATTGTGCGAAATTGCATATGTTTACGGAGACACACAGCAGATTCC
ATACATCAATAGAGTTTCAGGATTCCCGTACCCCGCCCATTTTGCCAAATTGG
AAGTTGACGAGGTGGAGACACGCAGAACTACTCTCCGTTGTCCAGCCGATGT
CACACATTATCTGAACAGGAGATATGAGGGCTTTGTCATGAGCACTTCTTCGG
TTAAAAAGTCTGTTTCGCAGGAGATGGTCGGCGGAGCCGCCGTGATCAATCC
GATCTCAAAACCCTTGCATGGCAAGATCCTGACTTTTACCCAATCGGATAAA
GAAGCTCTGCTTTCAAGAGGGTATTCAGATGTTCACACTGTGCATGAAGTGC
AAGGCGAGACATACTCTGATGTTTCACTAGTTAGGTTAACCCCTACACCGGTC
TCCATCATTGCAGGAGACAGCCCACATGTTTTGGTCGCATTGTCAAGGCACAC
CTGTTCGCTCAAGTACTACACTGTTGTTATGGATCCTTTAGTTAGTATCATTAG
AGATCTAGAGAAACTTAGCTCGTACTTGTTAGATATGTATAAGGTCGATGCA
GGAACACAATAGCAATTACAGATTGACTCGGTGTTCAAAGGTTCCAATCTTTT
TGTTGCAGCGCCAAAGACTGGTGATATTTCTGATATGCAGTTTTACTATGATA
AGTGTCTCCCAGGCAACAGCACCATGATGAATAATTTTGATGCTGTTACCATG
AGGTTGACTGACATTTCATTGAATGTCAAAGATTGCATATTGGATATGTCTAA
GTCTGTTGCTGCACCTAAGGATCAAATCAAACCACTAATACCTATGGTACGA
ACGGCGGCAGAAATGCCACGCCAGACTGGACTATTGGAAAATTTAGTGGCGA
TGATTAAAAGAAACTTTAACGCACCCGAGTTGTCTGGCATCATTGATATTGAA
AATACTGCATCTTTGGTTGTAGATAAGTTTTTTGATAGTTATTTGCTTAAAGA
AAAAAGAAAACCAAATAAAAATGTTTCTTTGTTCAGTAGAGAGTCTCTCAAT
AGATGGTTAGAAAAGCAGGAACAGGTAACAATAGGCCAGCTCGCAGATTTTG
ATTTTGTGGATTTGCCAGCAGTTGATCAGTACAGACACATGATTAAAGCACA
ACCCAAACAAAAGTTGGACACTTCAATCCAAACGGAGTACCCGGCTTTGCAG
ACGATTGTGTACCATTCAAAAAGATCAATGCAATATTCGGCCCGTTGTTTAG
TGAGCTTACTAGGCAATTACTGGACAGTGTTGATTCGAGCAGATTTTGTTTT
TCACAAGAAAGACACCAGCGCAGATTGAGGATTTCTTCGGAGATCTCGACAG
TCATGTGCCGATGGATGTCTTGGAGCTGGATATATCAAAATACGACAAATCT
CAGAATGAATTCCACTGTGCAGTAGAATACGAGATCTGGCGAAGATTGGGTT
TCGAAGACTTCTTGGGAGAAGTTTGGAAACAAGGGCATAGAAAGACCACCCT
CAAGGATTATACCGCAGGTATAAAAACTTGCATCTGGTATCAAAGAAAGAGC
GGGGACGTCACGACGTTCATTGGAAACACTGTGATCATTGCTGCATGTTTGGC
CTCGATGCTTCCGATGGAGAAAATAATCAAAGGAGCCTTTTGCGGTGACGAT
AGTCTGCTGTACTTTCCAAAGGGTTGTGAGTTTCCGGATGTGCAACACTCCG
```

FIG 5-2

```
CGAATCTTATGTGGAATTTTGAAGCAAAACTGTTTAAAAAACAGTATGGATA
CTTTTGCGGAAGATATGTAATACATCACGACAGAGGATGCATTGTGTATTAC
GATCCCCTAAAGTTGATCTCGAAACTTGGTGCTAAACACATCAAGGATTGGG
AACACTTGGAGGAGTTCAGAAGGTCTCTTTGTGATGTTGCTGTTTCGTTGAAC
AATTGTGCGTATTACACACAGTTGGACGACGCTGTATGGGAGGTTCATAAGA
CCGCCCCTCCAGGTTCGTTTGTTTATAAAAGTCTGGTGAAGTATTTGTCTGAT
AAAGTTCTTTTAGAAGTTTGTTTATAGATGGCTCTAGTTGTTAAAGGAAAAG
TGAATATCAATGAGTTTATCGACCTGACAAAAATGGAGAAGATCTTACCGTC
GATGTTTACCCCTGTAAAGAGTGTTATGTGTTCCAAAGTTGATAAAATAATGG
TTCATGAGAATGAGTCATTGTCAGGGGTGAACCTTCTTAAAGGAGTTAAGCTT
ATTGATAGTGGATACGTCTGTTTAGCCGGTTTGGTCGTCACGGGCGAGTGGA
ACTTGCCTGACAATTGCAGAGGAGGTGTGAGCGTGTGTCTGGTGGACAAAAG
GATGGAAAGAGCCGACGAGGCCATTCTCGGATCTTACTACACAGCAGCTGCA
AAGAAAAGATTTCAGTTCAAGGTCGTTCCCAATTATGCTATAACCACCCAGG
ACGCGATGAGAAACGTCTGGCAAGTTTTAGTTAATATTAGAAATGTGAAGAT
GTCAGCGGGTTTCTGTCCGCTTTCTCTGGAGTTTGTGTCGGTGTGTATTGTTTA
TAGAAATAATATAAAATTAGGTTTGAGAGAGAAGATTACAAACGTGAGAGA
CGGAGGGCCCATGGAACTTACAGAAGAAGTCGTTGATGAGTTCATGGAAGAT
GTCCCTATGTCGATCAGGCTTGCAAAGTTTCGATCTCGAACCGGAAAAAAGA
GTGATGTCCGCAAAGGGAAAAATAGTAGTAGTGATCGGTCAGTGCCGAACAA
GAACTATAGAAATGTTAAGGATTTTGGAGGAATGAGTTTTAAAAAGAATAAT
TTAATCGATGATGATTCGGAGGCTACTGTCGCCGAATCGGATTCGTTTTAAAT
AGATCTTACAGTATCACTACTCCATCTCAGTTCGTGTTCTTGTCAttaattaaATGG
CTAGCAAAGGAGAAGAACTTTTCACTGGAGTTGTCCCAATTCTTGTTGAATTA
GATGGTGATGTTAATGGGCACAAATTTTCTGTCAGTGGAGAGGGTGAAGGTG
ATGCTACATACGGAAAGCTTACACTTAAATTTATTTGCACTACTGGAAAACTA
CCTGTTCCATGGCCAACACTTGTCACTACTTTCTCTTATGGTGTTCAATGCTTT
TCCCGTTATCCGGATCATATGAAACGGCATGACTTTTTCAAGAGTGCCATGCC
CGAAGGTTATGTACAGGAACGCACTATATCTTTCAAAGATGACGGGAACTAC
AAGACGCGTGCTGAAGTCAAGTTTGAAGGTGATACCCTTGTTAATCGTATCG
AGTTAAAAGGTATTGATTTTAAAGAAGATGGAAACATTCTCGGACACAAACT
CGAGTACAACTATAACTCACACAATGTATACATCACGGCAGACAAACAAAAG
AATGGAATCAAAGCTAACTTCAAAATTCGCCACAACATTGAAGATGGATCCG
TTCAACTAGCAGACCATTATCAACAAATACTCCAATTGGCGATGGCCCTGTC
CTTTTACCAGACAACCATTACCTGTCGACACAATCTGCCCTTTCGAAAGATCC
CAACGAAAAGCGTGACCACATGGTCCTTCTTGAGTTTGTAACTGCTGCTGGG
ATTACACATGGCATGGATGAGCTCTACAAATAATGACACTCGAGGGGTAGTC
AAGATGCATAATAAATAACGGATTGTGTCCGTAATCACACGTGGTGCGTACG
ATAACGCATAGTGTTTTTCCCTCCACTTAAATCGAAGGGTTGTGTCTTGGATC
GCGCGGGTCAAATGTATATGGTTCATATACATCCGCAGGCACGTAATAAAGC
GAGGGGTTCGGGTCGAGGTCGGCTGTGAAACTCGAAAGGTTCCGGAAAAC
AAAAAAGAGAGTGGTAGGTAATAGTGTTAATAATAAGAAAATAAATAATAG
TGGTAAGAAAGGTTTGAAAGTTGAGGAAATTGAGGATAATGTAAGTGATGAC
GAGTCTATCGCGTCATCGAGTACGTTTTAATCAATATGCCTTATACAATCAAC
TCTCCGAGCCAATTTGTTTACTTAAGTTCCGCTTATGCAGATCCTGTGCAGCT
GATCAATCTGTGTACAAATGCATTGGGTAACCAGTTTCAAACGCAACAAGCT
```

FIG 5-3

AGGACAACAGTCCAACAGCAATTTGCGGATGCCTGGAAACCTGTGCCTAGTA
TGACAGTGAGATTTCCTGCATCGGATTTCTATGTGTATAGATATAATTCGACG
CTTGATCCGTTGATCACGGCGTTATTAAATAGCTTCGATACTAGAAATAGAAT
AATAGAGGTTGATAATCAACCCGCACCGAATACTACTGAAATCGTTAACGCG
ACTCAGAGGGTAGACGATGCGACTGTAGCTATAAGGGCTTCAATCAATAATT
TGGCTAATGAACtGGTTCGTGGAACTGGCaTGTTCAATCAAGCAAGCTTTGAG
ACTGCTAGTGGACTTGTCTGGACCACAACTCCGGCTACTTAGctattgttgtgagatttcct
aaaataaagtcactgaagacttaaaattcagggtggctgataccaaaatcagcagtggttgttcgtccacttaaatataacgattgt
catatctggatccaacagttaaaccatgtgatggtgtatactgtggtatggcgtaaaacaacggaaaagtcgctgaagacttaaaa
ttcagggtggctgataccaaaatcagcagtggttgttcgtccacttaaaaataacgattgtcatatctggatccaacagttaaaccat
gtgatggtgtatactgtggtatggcgtaaaacaacggagaggttcgaatcctcccctaaccgcgggtagcggccca

FIG 5-4

P1056-GTN 28

```
GTCGTATTTTTACAACAATTACCAACAACAACAAACAACAGACAACATTACA
ATTACTATTTACAATTACAATGGCATACACACAGACAGCTACCACATCAGCTT
TGCTGGACACTGTCCGAGGAAACAACTCCTTGGTCAATGATCTAGCAAAGCG
TCGTCTTTACGACACAGCGGTTGAAGAGTTTAACGCTCGTGACCGCAGGCCC
AAGGTGAACTTTTCAAAAGTAATAAGCGAGGAGCAGACGCTTATTGCTACCC
GGGCGTATCCAGAATTCCAAATTACATTTTATAACACGCAAAATGCCGTGCA
TTCGCTTGCAGGTGGATTGCGATCTTTAgAACTGGAATATCTGATGATGCAAA
TTCCCTACGGATCATTGACTTATGACATAGGCGGGAATTTTGCATCGCATCTG
TTCAAGGGACGAGCATATGTACACTGCTGCATGCCCAACCTGGACGTTCGAG
ACATCATGCGGCACGAAGGCCAGAAAGACAGTATTGAACTATACCTTTCTAG
GCTAGAGAGAGGGGGGAAAACAGTCCCCAACTTCCAAAAGGAAGCATTTGA
CAGATACGCAGAAATTCCTGAAGACGCTGTCTGTCACAATACTTTCCAGACA
TGCGAACATCAGCCGATGCAGCAATCAGGCAGAGTGTATGCCATTGCGCTAC
ACAGCATATATGACATACCAGCCGATGAGTTCGGGGCGGCACTCTTGAGGAA
AAATGTCCATACGTGCTATGCCGCTTTCCACTTCTCCGAGAACCTGCTTCTTG
AAGATTCATGCGTCAATTTGGACGAAATCAACGCGTGTTTTCGCGCGATGG
AGACAAGTTGACCTTTTCTTTTGCATCAGAGAGTACTCTTAATTACTGTCATA
GTTATTCTAATATTCTTAAGTATGTGTGCAAAACTTACTTCCCGGCCTCTAAT
AGAGAGGTTTACATGAAGGAGTTTTTAGTCACCAGAGTTAATACCTGGTTTTG
TAAGTTTTCTAGAATAGATACTTTTCTTTTGTACAAAGGTGTGGCCCATAAAA
GTGTAGATAGTGAGCAGTTTTATACTGCAATGGAAGACGCATGGCATTACAA
AAAGACTCTTGCAATGTGCAACAGCGAGAGAATCCTCCTTGAGGATTCATCA
TCAGTCAATTACTGGTTTCCCAAAATGAGGGATATGGTCATCGTACCATTATT
CGACATTTCTTTGGAGACTAGTAAGAGGACGCGCAAGGAAGTCTTAGTGTCC
AAGGATTTCGTGTTTACAGTGCTTAACCACATTCGAACATACCAGGCGAAAG
CTCTTACATACGCAAATGTTTGTCCTTCGTCGAATCGATTCGATCGAGGGT
AATCATTAACGGTGTGACAGCGAGGTCCGAATGGGATGTGGACAAATCTTTG
TTACAATCCTTGTCCATGACGTTTACCTGCATACTAAGCTTGCCGTTCTAAA
GGATGACTTACTGATTAGCAAGTTTAGTCTCGGTTCGAAAACGGTGTGCCAG
CATGTGTGGGATGAGATTTCGCTGGCGTTTGGGAACGCATTTCCCTCCGTGAA
AGAGAGGCTCTTGAACAGGAAACTTATCAGAGTGGCAGGCGACGCATTAGA
GATCAGGGTGCCTGATCTATATGTGACCTTCCACGACAGATTAGTGACTGAGT
ACAAGGCCTCTGTGGACATGCCTGCGCTTGACATTAGGAAGAAGATGGAAGA
AACGGAAGTGATGTACAATGCACTTTCAGAATTATCGGTGTTAAGGGAGTCT
GACAAATTCGATGTTGATGTTTTTCCCAGATGTGCCAATCTTTGGAAGTTGA
CCCAATGACGGCAGCGAAGGTTATAGTCGCGGTCATGAGCAATGAGAGCGGT
CTGACTCTCACATTTGAACGACCTACTGAGGCGAATGTTGCGCTAGCTTTACA
GGATCAAGAGAAGGCTTCAGAAGGTGCATTGGTAGTTACCTCAAGAGAAGTT
GAAGAACCGTCCATGAAGGGTTCGATGGCCAGAGGAGAGTTACAATTAGCTG
GTCTTGCTGGAGATCATCCGGAATCGTCCTATTCTAAGAACGAGGAGATAGA
GTCTTTAGAGCAGTTTCATATGGCGACGGCAGATTCGTTAATTCGTAAGCAGA
TGAGCTCGATTGTGTACACGGGTCCGATTAAAGTTCAGCAAATGAAAAACTT
TATCGATAGCCTGGTAGCATCACTATCTGCTGCGGTGTCGAATCTCGTCAAGA
TCCTCAAAGATACAGCTGCTATTGACCTTGAAACCCGTCAAAAGTTTGGAGTC
```

FIG 6-1

```
TTGGATGTTGCATCTAGGAAGTGGTTAATCAAACCAACGGCCAAGAGTCATG
CATGGGGTGTTGTTGAAACCCACGCGAGGAAGTATCATGTGGCGCTTTTGGA
ATATGATGAGCAGGGTGTGGTGACATGCGATGATTGGAGAAGAGTAGCTGTT
AGCTCTGAGTCTGTTGTTTATTCCGACATGGCGAAACTCAGAACTCTGCGCAG
ACTGCTTCGAAACGGAGAACCGCATGTCAGTAGCGCAAAGGTTGTTCTTGTG
GACGGAGTTCCGGGCTGTGGAAAAACCAAAGAAATTCTTTCCAGGGTTAATT
TTGATGAAGATCTAATTTTAGTACCTGGGAAGCAAGCCGCGGAAATGATCAG
AAGACGTGCGAATTCCTCAGGGATTATTGTGGCCACGAAGGACAACGTTAAA
ACCGTTGATTCTTTCATGATGAATTTTGGGAAAAGCACACGCTGTCAGTTCAA
GAGGTTATTCATTGATGAAGGGTTGATGTTGCATACTGGTTGTGTTAATTTTC
TTGTGGCGATGTCATTGTGCGAAATTGCATATGTTACGGAGACACACAGCA
GATTCCATACATCAATAGAGTTTCAGGATTCCCGTACCCCGCCCATTTTGCCA
AATTGGAAGTTGACGAGGTGGAGACACGCAGAACTACTCTCCGTTGTCCAGC
CGATGTCACACATTATCTGAACAGGAGATATGAGGGCTTTGTCATGAGCACT
TCTTCGGTTAAAAAGTCTGTTTCGCAGGAGATGGTCGGCGGAGCCgCCGTGAT
CAATCCGATCTCAAAACCCTTGCATGGCAAGATCTTGACTTTTACCCAATCGG
ATAAAGAAGCTCTGCTTTCAAGAGGGTATTCAGATGTTCACACTGTGCATGA
AGTGCAAGGCGAGACATACTCTGATGTTTCACTAGTTAGGTTAACCCCTACAC
CGGTCTCCATCATTGCAGGAGACAGCCCACATGTTTTGGTCGCATTGTCAAGG
CACACCTGTTCGCTCAAGTACTACACTGTTGTTATGGATCCTTTAGTTAGTAT
CATTAGAGATCTAGAGAAACTTAGCTCGTACTTGTTAGATATGTATAAGGTCG
ATGCAGGAACACAATAGCAATTACAGATTGACTCGGTGTTCAAAGGTTCCAA
TCTTTTTGTTGCAGCGCCAAAGACTGGTGATATTCTGATATGCAGTTTTACT
ATGATAAGTGTCTCCCAGGCAACAGCACCATGATGAATAATTTTGATGCTGTT
ACCATGAGGTTGACTGACATTTCATTGAATGTCAAAGATTGCATATTGGATAT
GTCTAAGTCTGTTGCTGCGCCTAAGGATCAAATCAAACCACTAATACCTATGG
TACGAACGGCGGCAGAAATGCCACGCCAGACTGGACTATTGGAAAATTTAGT
GGCGATGATTAAAAGAAACTTTAACGCACCCGAGTTGTCTGGCATCATTGAT
ATTGAAAATACTGCATCTTTGGTTGTAGATAAGTTTTTTGATAGTTATTTGCTT
AAAGAAAAAAGAAAACCAAATAAAAATGTTTCTTTGTTCAGTAGAGAGTCTC
TCAATAGATGGTTAGAAAAGCAGGAACAGGTAACAATAGGCCAGCTCGCAG
ATTTTGATTTTGTGGATTTGCCAGCAGTTGATCAGTACAGACACATGATTAAA
GCACAACCCAAACAAAAGTTGGACACTTCAATCCAAACGGAGTACCCGGCTT
TGCAGACGATTGTGTACCATTCAAAAAGATCAATGCAATATTCGGCCCGTT
GTTTAGTGAGCTTACTAGGCAATTACTGGACAGTGTTGATTCGAGCAGATTTT
TGTTTTTCACAAGAAAGACACCAGCGCAGATTGAGGATTTCTTCGGAGATCTC
GACAGTCATGTGCCGATGGATGTCTTGGAGCTGGATATATCAAAATACGACA
AATCTCAGAATGAATTCCACTGTGCAGTAGAATACGAGATCTGGCGAAGATT
GGGTTTCGAAGACTTCTTGGGAGAAGTTTGGAAACAAGGGCATAGAAAGACC
ACCCTCAAGGATTATACCGCAGGTATAAAAACTTGCATCTGGTATCAAAGA
AAGAGCGGGGACGTCACGACGTTCATTGGAAACACTGTGATCATTGCTGCAT
GTTTGGCCTCGATGCTTCCGATGGAGAAAATAATCAAAGGAGCCTTTTGCGG
TGACGATAGTCTGCTGTACTTTCCAAAGGGTTGTGAGTTTCCGGATGTGCAAC
ACTCCGCGAATCTTATGTGGAATTTTGAAGCAAAACTGTTTAAAAAACAGTA
TGGATACTTTTGCGGAAGATATGTAATACATCACGACAGAGGATGCATTGTG
TATTACGATCCCCTAAAGTTGATCTCGAAACTTGGTGCTAAACACATCAAGG
```

FIG 6-2

```
ATTGGGAACACTTGGAGGAGTTCAGAAGGTCTCTTTGTGATGTTGCTGTTTCG
TTGAACAATTGTGCGTATTACACACAGTTGGACGACGCTGTATGGGAGGTTC
ATAAGACCGCCCCTCCAGGTTCGTTTGTTTATAAAAGTCTGGTGAAGTATTTG
TCTGATAAAGTTCTTTTTAGAAGTTTGTTTATAGATGGCTCTAGTTGTTAAAG
GAAAAGTGAATATCAATGAGTTTATCGACCTGACAAAAATGGAGAAGATCTT
ACCGTCGATGTTTACCCCTGTAAAGAGTGTTATGTGTTCCAAAGTTGATAAAA
TAATGGTTCATGAGAATGAGTCATTGTCAGGGGTGAACCTTCTTAAAGGAGT
TAAGCTTATTGATAGTGGATACGTCTGTTTAGCCGGTTTGGTCGTCACGGGCG
AGTGGAACTTGCCTGACAATTGCAGAGGAGGTGTGAGCGTGTGTCTGGTGGA
CAAAAGGATGGAAAGAGCCGACGAGGCCATTCTCGGATCTTACTACACAGCA
GCTGCAAAGAAAAGATTTCAGTTCAAGGTCGTTCCCAATTATGCTATAACCA
CCCAGGACGCGATGAAAACGTCTGGCAAGTTTTAGTTAATATTAGAAATGT
GAAGATGTCAGCGGGTTTCTGTCCGCTTTCTCTGGAGTTTGTGTCGGTGTGTA
TTGTTTATAAAAATAATATAAAATTAGGTTTGAGAGAGAAGATTACAAACGT
GAGAGACGGAGGGCCCATGGAACTTACAGAAGAAGTCGTTGATGAGTTCATG
GAAGATGTCCCTATGTCGATCAGGCTTGCAAAGTTTCGATCTCGAACCGGAA
AAAAGAGTGATGTCCGCAAAGGGAAAAATAGTAGTAGTGATCGGTCAGTGC
CGAACAAGAACTATAGAAATGTTAAGGATTTGGAGGAATGAGTTTTAAAAA
GAATAATTTAATCGATGATGATTCGGAGGCTACTGTCGCCGAATCGGATTCGT
TTTAAATAGATCTTACAGTATCACTACTCCATCTCAGTTCGTGTTCTTGTCATT
AATTAAATGGCTAGCAAAGGAGAAGAACTTTTCACTGGAGTTGTCCCAATTC
TTGTTGAATTAGATGGTGATGTTAATGGGCACAAATTTTCTGTCAGTGGAGAG
GGTGAAGGTGATGCTACATACGGAAAGCTTACCCTTAAATTTATTTGCACTAC
TGGAAAACTACCTGTTCCATGGCCAACACTTGTCACTACTTTCTCTTATGGTG
TTCAATGCTTTTCCCGTTATCCGGATCATATGAAACGGCATGACTTTTTCAAG
AGTGCCATGCCCGAAGGTTATGTACAGGAACGCACTATATCTTTCAAAGATG
ACGGGAACTACAAGACGCGTGCTGAAGTCAAGTTTGAAGGTGATACCCTTGT
TAATCGTATCGAGTTAAAAGGTATTGATTTTAAAGAAGATGGAAACATTCTC
GGACACAAACTCGAGTACAACTATAACTCACACAATGTATACATCACGGCAG
ACAAACAAAAGAATGGAATCAAAGCTAACTTCAAAATTCGCCACAACATTGA
AGATGGATCCGTTCAACTAGCAGACCATTATCAACAAAATACTCCAATTGGC
GATGGCCCTGTCCTTTTACCAGACAACCATTACCTGTCGACACAATCTGCCCT
TTCGAAAGATCCCAACGAAAAGCGTGACCACATGGGCCTTCTTGAGTTTGTA
ACTGCTGCTGGGATTACACATGGCATGGATGAGCTCTACAAATAATGACACT
CGAGGGGTAGTCAAGATGCATAATAAATAACGGATTGTGTCCGTAATCACAC
GTGGTGCGTACGATAACGCATAGTGTTTTTCCCTCCACTTAAATCGAAGGGTT
GTGTCTTGGATCGCGCGGGTCAAATGTATATGGTTCATATACATCCGCAGGCA
CGTAATAAAGCGAGGGGTTCGGGTCGAGGTCGGCTGTGAAACTCGAAAAGGT
TCCGGAAAACAAAAAGAGAGTGGTAGGTAATAGTGTTAATAATAAGAAAA
TAAATAATAGTGGTAAGAAAGGTTTGAAAGTTGAGGAAATTGAGGATAATGT
AAGTGATGACGAGTCTATCGCGTCATCGAGTACGTTTAATCAATATGCCTTA
TACAATCAACTCTCCGAGCCAATTTGTTTACTTAAGTTCCGCTTATGCAGATC
CTGTGCAGCTGATCAATCTGTGTACAAATGCATTGGGTAACCAGTTTCAAACG
CAACAAGCTAGGACAACAGTCCAACAGCAATTTGCGGATGCCTGGAAACCTG
TGCCTAGTATGACAGTGAGATTTCCTGCATCGGATTTCTATGTGTATAGATAT
AATTCGACGCTTGATCCGTTGATCACGGCGTTATTAAATAGCTTCGATACTAG
```

FIG 6-3

```
AAATAGAATAATAGAGGTTGATAATCAACCCGCACCGAATACTACTGAAATC
GTTAACGCGACTCAGAGGGTAGACGATGCGACTGTAGCTATAAGGGCTTCAA
TCAATAATTTGGCTAATGAACTGGTTCGTGGAACTGGCATGTTCAATCAAGC
AAGCTTTGAGACTGCTAGTGGACTTGTCTGGACCACAACTCCGGCTACTTAGC
TATTGTTGTGAGATTTCCTAAAATAAAGTCACTGAAGACTTAAAATTCAGGGT
GGCTGATACCAAAATCAGCAGTGGTTGTTCGTCCACTTAAATATAACGATTGT
CATATCTGGATCCAACAGTTAAACCATGTGATGGTGTATACTGTGGTATGGCG
TAAAACAACGGAAAGTCGCTGAAGACTTAAAATTCAGGGTGGCTGATACCA
AAATCAGCAGTGGTTGTTCGTCCACTTAAAAATAACGATTGTCATATCTGGAT
CCAACAGTTAAACCATGTGATGGTGTATACTGTGGTATGGCGTAAACAACGG
AGAGGTTCGAATCCTCCCCTAACCGCGGgtagcggccca
```

FIG 6-4

RNA TRANSFORMATION VECTORS DERIVED FROM A SINGLE-COMPONENT RNA VIRUS AND CONTAIN AN INTERVENING SEQUENCE BETWEEN THE CAP AND THE 5' END

This application is a continuation-in-part of U.S. patent application Ser. Nos. 09/359,301 and 09/359,305, filed Jul. 21, 1999, which are continuations-in-part of U.S. patent application Ser. No. 09/232,170, filed Jan. 15, 1999, which is a continuation-in-part of U.S. patent application Ser. No. 09/008,186, filed Jan. 16, 1998. The above parent applications are incorporated herein by reference.

FIELD OF THE INVENTION

This invention relates to the field of plant viruses, more particularly to plus-sense RNA plant virus, and to modifications, made according to the teachings herein, which permit insertion of an exogenous RNA segment into the viral genome. The recombinant plant viral nucleic acid construct derived from insertion of an exogenous RNA segment into the viral genome can then be introduced into a host cell in order to modify the cell.

BACKGROUND OF THE INVENTION

RNA viruses whose genome is composed of a single RNA strand capable of replication in the cytoplasm of a host by direct RNA replication are widespread, many varieties of which are known to infect plants. Such viruses are sometimes termed "(+) strand RNA viruses" since the infective RNA strand, that normally found encapsidated in the virus particle, is a messenger-sense strand, capable of being directly translated, and also capable of being replicated under the proper conditions by a direct process of RNA replication. Viruses belonging to this group include "single component (+) strand RNA viruses", which replicate in the absence of trans-acting viral replication elements. These viruses may include, but are not limited to any of the representatives of the following virus groups, Carlavirus, Closteroviridae, Luteoviridae, Potexvirus, Potyviridae, Tombusviridae, Tobamovirus and Tymovinis. (Similar viruses, which in the host cell produce a trans-acting replication element, are not included in this group.) In these cases, the entire virus genome is contained within a single RNA molecule, while in the multicomponent RNA plant viruses, the total genome of the virus consists of two or more distinct RNA segments, each separately encapsidated. For general review, see General Virology, S. Luria and J. Darnell; Plant Virology 2nd ed., R. E. F. Matthews, Academic Press (1981). For a general review of (+) strand RNA replication, see Davies and Hull (1982) *J. Gen. Virol.* 61:1.

Despite the well-documented diversity between virus groups, recent studies have shown striking similarities between the proteins, which function in RNA replication. Sequence homologies have been reported between the cowpea mosaic virus, poliovirus and foot-and-mouth disease virus, (Franssen, H. (1984) *EMBO Journal* 3,855). Sequence homologies have been reported between non-structural proteins encoded by alfalfa mosaic virus, brome mosaic virus and tobacco mosaic virus, Haseloff, J. et al. (1984), Proc. Nat. Acad. Sci. USA 81, 4358, and between non-structural proteins encoded by sindbis virus, Ahlquist, P. et al. (1985) *J. Virol.* 53, 536. Evidence of such substantial homology in proteins related to the replication functions indicate that the viruses share mechanistic similarities in their replication strategies and may actually be evolutionarily related. Ahlquist et al., in U.S. Pat. No. 5,500,360 made modifications to the genomic RNA of a (+) strand RNA virus of a multipartite Brome mosaic virus. The modified RNA was used to transfer a desired RNA segment into a targeted host plant protoplast, and to replicate that segment and express its function within the host protoplast.

In contrast to the Brome mosaic virus (BMV), the tobacco mosaic virus (TMV) is one member of a class of plant viruses characterized by a single RNA genome. The genetic material of the virus is RNA, and the total genetic information required for replication and productive infection is contained in one discrete RNA molecule. Infection of a host plant cell occurs when the single RNA component of the viral genome has infected the cell, for example by exposing a plant to a virus preparation. Infection may also be achieved by exposing a plant cell or protoplast to a virus preparation. TMV does not require coat protein for infection. The RNA component is both necessary and sufficient for replication and productive infection. The TMV genome is a single messenger-sense RNA. The term "messenger-sense" denotes that the viral RNAs can be directly translated to yield viral proteins, without the need for an intervening transcription step.

Complete cDNA copies of the genetic component of TMV have been cloned. Construction of a library of subgenomic cDNA clones of TMV has been described in Dawson et al., *Proc. Natl. Acad. Sci. USA* 83:1832–1836 (1986) and Ahlquist et al., *Proc. Natl. Acad. Sci. USA* 81:7066–7070 (1984). Several examples of TMV transcription vectors are described below. DNA from each of the TMV cDNA-containing plasmids can be cleaved. The linear DNA thus produced can be transcribed in vitro in a reaction catalyzed by RNA polymerase. A T7 promoter in the transcription vector allows RNA synthesis to initiate at the 5' terminus of each TMV sequence, and transcription continues to the end of the DNA template. The 5' terminus of tobacco mosaic virus (TMV) RNA, was identified as $m^7G^{5'}ppp^{5'}Gp$. Zimmern, D., *Nucleic Acid Res.* 2:1189–1201 (1975). Keith, J. and fraenkel-Conrat, H. *FEBS Lett.* 57:31–33 (1975). Ahlquist, U.S. Pat. No. 5,500,360, working with Brome mosaic virus, reported that when transcription is carried out in the presence of a synthetic cap structure, $m^7$ GpppG, as described by Contreras, R., et al. *Nucleic Acids Res.* 10:6353, (1982), RNA transcripts are produced with the same capped 5' ends as authentic BMV RNAs. Ahlquist concluded that these RNAs are active messengers in in vitro translation systems and direct production of proteins with the same electrophoretic mobilities as those translated from authentic BMV RNAs. However, Ahlquist found that, "if the cap analog was omitted during in vitro transcription, no infection was detected, even if inoculum concentration was increased 20-fold." Further, Ahlquist taught only a viral vector having "no extraneous nonviral sequences between the cap and the 5' terminus of the viral sequence." In Ahlquist's work on BMV, U.S. Pat. No. 5,500,360, a transcription vector was employed which preserved the exact 5' terminal nucleotide sequence of viral RNA. It is now generally accepted that capping is necessary for infectivity and that no intervening sequence can be present between the cap and the 5' terminus of the viral sequence.

The work of Ahlquist leaves us with difficult problems to overcome if we are to obtain a workable viral vector or a commercially viable viral vector. One such problem is the cost of using capping structures and cap analogs. Another such problem is that multipartite viral vectors are difficult to use relative to a single component viral vector. Multipartite viruses require more than one unit to infect and achieve replication in a host plant, and multipartite viruses require a trans acting replication element to achieve replication. No one has yet found a way to unite the multiple strands of a multipartite virus into an RNA molecule comprising the entire genome of a (+) strand RNA virus as suggested and claimed by Ahlquist.

Therefore, there is a need for a viral vector that can accept an intervening base or intervening sequence of bases between the cap and the 5' terminus of the viral sequence and undergo transcription and replication. There is also a need for a viral vector that can undergo transcription and replication in the absence of a capping structure.

Here we teach solutions to the problem by demonstrating:
1. Infection of a host and replication of a viral vector in vivo in the presence of a base or a sequence of bases placed 5' to the origin of replication in the absence of a capping structure or cap analog.
2. Infection of a host and replication of a viral vector in vivo in the absence of a capping structure or a cap analog, and in the absence of a base or a sequence of bases placed 5' to the origin of replication.
3. Infection of a host and replication of a viral vector in vivo in the presence of an intervening base or an intervening sequence of bases placed 5' to the origin of replication and in the presence of a capping structure or cap analog.

The viral vectors demonstrated here have utility in discovery the function of genes, and in production of therapeutic proteins.

SUMMARY OF THE INVENTION

The For the sake of brevity, the term "RNA virus" is used herein to mean (+) strand replicating RNA viruses. Most single component RNA viruses have the advantage over multicomponent RNA viruses of having a single RNA structure. Because they have a single RNA structure, the function of an exogenous RNA segment can be expressed in a host cell in the absence of a trans-acting replication element. Further, the single component RNA virus does not express the 3a movement gene that is indigenous to the Brome mosaic virus.

The invention is based on the discovery that the 5' end of a single component RNA viral vector can be modified by leaving out the capping structure so that the virus transcript is uncapped. The invention is also based on the discovery that the 5' end of a single component RNA viral vector can be modified by inserting a base or a sequence of bases ahead of the 5' terminus of the viral sequence. The invention is also based on the discovery that the 5' end of a single component RNA viral vector can be modified by inserting an intervening base or an intervening sequence of bases between the cap and the 5' terminus of the viral sequence. The genome of a virus, modified in each of these three ways, can be further modified to include an exogenous RNA segment. The further modified RNA can be introduced into a host cell where it will replicate and express the exogenous RNA segment. The recipient cell is thereby phenotypically transformed and may contribute to a genotypically transformed organism, as well.

Phenotypically transformed plants and plant cells can be modified in vivo, in planta, in tissue culture, in cell culture or in the form of protoplasts. The exemplified embodiment of the invention is useful for producing phenotypically transformed plants under field or greenhouse growth conditions. Traits desirable for introduction in this manner include, but are not limited to, pest resistance, pathogen resistance, herbicide tolerance or resistance, modified growth habit and modified metabolic characteristics, such as the production of commercially useful peptides or pharmaceuticals in plants. The modifications can be applied at any time during the growth cycle, depending on the need for the trait. For example, resistance to a pest could be conferred only if the crop were at risk for that pest, and at the time when the crop was most likely to be affected by the pest. Other traits can be used to enhance secondary properties, for example to increase the protein content of post-harvest forage. Any plant variety susceptible to infection by a single component RNA virus can be phenotypically transformed. The choice of virus and the details of modification will be matters of choice depending on parameters known and understood by those of ordinary skill in the art. Other uses for cells and organisms phenotypically or genotypically modified by means of a modified RNA derived from an RNA virus will be readily apparent to those skilled in the art, given a wide range of RNA viruses to modify and a wide range of susceptible host cell types. Other uses for transformed animal cells, bacterial cells and the like can be readily envisioned but are not demonstrated here.

Generally, the steps of a process for phenotypically transforming a cell or organism are:

- forming a full-length cDNA transcript of the RNA virus;
- cloning the cDNA in a transcription vector;
- modifying the cDNA by inserting a non-viral DNA segment in a region able to tolerate such insertion without disrupting RNA replication thereof;
- transcribing the modified cDNA corresponding to the RNA component of the single component virus;
- infecting virus-susceptible protoplasts, cells, tissues or whole plants with transcribed RNA, either in solution or encapsidated, of the modified RNA comprising messenger-sense RNA containing an exogenous RNA segment.

From this point, the steps to be followed will vary, depending on the type of material infected and the route of infection. Protoplasts, cells and tissues of plants can be propagated vegetatively, regenerated to yield whole plants by means of any technique suitable to the particular plant variety infected, and transplanted to the field. Whole plants can be infected in situ. Infected plants and plant cells can produce many copies per cell of the modified viral RNA containing the exogenous RNA segment. If desired and if suitably inserted, by means of principles and processes known in the art, the exogenous RNA segment can be caused to carry out a function within the cell. Such a function could be a coding function, translated within the cell to yield a desired peptide or protein, or it could be a regulatory function, increasing, decreasing, and turning on or off the expression of certain genes within the cell. In principle, any function, which a segment of RNA is capable of providing, can be expressed within the cell. The exogenous RNA segment thus expressed confers a new phenotypic trait to the transformed organism, plant, cells, protoplasts or tissues.

The invention is exemplified herein by the modification of TMV RNA to contain a structural gene encoding green fluorescent protein (GFP) and the phenotypic modification of Nicotiana plants and protoplasts therewith, yielding plants and protoplasts synthesizing GFP. The data presented herein are believed to represent the first instance of phenotypic modification of a cell by means of an RNA virus which is uncapped and which has no base at the 5' end of the uncapped viral sequence.

The data presented herein are believed to represent the first instance of phenotypic modification of a cell by means of an RNA virus which is uncapped and which has a single base or a sequence of bases at the 5' end of an uncapped viral sequence. The data presented herein are believed to represent the first instance of phenotypic modification of a cell by means of an RNA virus which contains an intervening base or intervening sequence of bases between the cap and the 5' end of the viral sequence.

BRIEF DESCRIPTION OF THE DRAWINGS

FIG. 1 shows the sequence of pBTI 30BGFPc3 (p1037) (SEQ ID NO: 22).

FIG. 2 shows the sequence of pBTI SBS60 (SEQ ID NO: 23).

FIG. 3 shows the sequence of pBTI SBS60-29 (SEQ ID NO: 24).

FIG. 4 shows the sequence of pBTI1056 (SEQ ID NO: 25).

FIG. 5 shows the sequence of pBTI SBS5 (p1057) (SEQ ID NO: 26).

FIG. 6 shows the sequence of pBTI1056-GTN28 (SEQ ID NO: 27).

DETAILED DESCRIPTION OF THE INVENTION

In order to facilitate understanding of the invention, certain terms used throughout are herein defined.

Base—The term base means adenine, thymidine, guanine, and cytosine, which in the form of a nucleotide can bond with other bases to form a nucleotide sequence. As used herein, a "base sequence" or a "sequence of bases" refers to a nucleotide sequence. The bases used herein are DNA bases, because all base or base sequence manipulations are performed on plasmid DNA prior to transcription. Base might be used interchangeably with "nucleotide".

RNA virus—The term as used herein means a virus whose genome is RNA in single-stranded form, the single strand being a (+) strand, or messenger-sense strand. Replication of the viral (+) strand in a virus-infected cell occurs by a process of direct RNA replication and is therefore distinguishable from the replication mechanism of retroviruses which undergo an intermediate step of reverse transcription in the host cell.

Cis-acting replication element—This term denotes that portion of the RNA genome of an RNA virus which must be present in cis, that is, present as part of each viral strand as a necessary condition for replication. Virus replication of a single component virus such as TMV has only cis-acting replication elements in its RNA. The cis-acting replication element is composed of one or more segments of viral RNA, which must be present on any RNA molecule that is to be replicated within a host cell by RNA replication. The segment will most likely be the 5' terminal portion of the viral RNA molecule, and may include other portions as well. As is demonstrated herein, using the example of TMV, substantial portions of an RNA virus molecule may be modified, by deletion, insertion, or by a combination of deletion and insertion, without disrupting replication.

Trans-acting replication element—In contrast to the single component (unipartite) virus, virus replication of a multipartite virus such as BMV presumably depends upon the existence of one or more trans (diffusible) elements which interact with the cis-acting element to carry out RNA replication. While trans-acting elements are necessary for replication of a multipartite virus such as BMV, they need not be present or coded for on the modified RNA provided they are made available within the infected cell by some other means. For example, in the case of a multipartite RNA virus, the trans-acting functions may be provided by other, unmodified components of the viral genome used to transform the cells simultaneously with the modified RNA. The target cell may also be modified in a previous step to provide constitutive expression of the trans-acting functions. In the case of a multipartite virus, the cis-acting element is therefore defined in functional terms: any modification which destroys the ability of the RNA to replicate in a cell known to contain the requisite trans-acting elements, is deemed to be a modification in the cis-acting replication element. Conversely, any modification, such as an insertion in a sequence region, which is able to tolerate such insertion without disrupting replication, is a modification outside the cis-acting replication element.

The term "derived from" is used to identify the viral source of an RNA segment, which comprises part of the modified RNA. For example, for the modified RNAs described herein, substantial portions thereof are derived from TMV. The manner of deriving, whether by direct recombination at the RNA level, by transcription or by reverse transcription does not matter for the purpose of the invention. Indeed, it is contemplated that modifications may be made within the cis-acting replication element and elsewhere for example to modify the rate or amount of replication that is obtained. In the case of modified RNAs exemplified herein, a transcription vector was employed which, preserved the exact 5' terminal nucleotide sequence of viral RNA, but a) left the capping structure off, or b) left the capping structure off and added a single base to the 5' terminal nucleotide sequence of the viral cDNA, or c) left the capping structure off and added a sequence of bases to the 5' terminal nucleotide sequence of the viral cDNA, or d) inserted a single intervening base between the cap and the 5' terminal nucleotide sequence of the viral eDNA, or e) inserted an intervening sequence of bases between the cap and the 5' terminal nucleotide sequence. The use of such a vector in transcribing viral RNA from will be preferred if preservation of the exact nucleotide sequence at the 5' end is desired. The use of such a vector in transcribing viral RNA from will be preferred if the objective is to only remove the cap without further objectives with respect to the 5' end of the virus. An RNA segment which has been derived from a given source virus may, but need not be, identical in sequence to that segment as it exists in the virus. It will be understood that a cis-acting replicating element derived from a given RNA virus may have minor modifications in the nucleotide sequence thereof without substantially interfering with RNA replication.

Exogenous RNA segment is a term used to describe a segment of RNA to be inserted into the virus RNA to be modified, the source of the exogenous RNA segment being different from the RNA virus itself. The source may be another virus, a living organism such as a plant, animal, bacteria, virus or fungus, the exogenous RNA may be a chemically synthesized RNA or it may be a combination of the foregoing. The exogenous RNA segment may provide any function that is appropriate and known to be provided by an RNA segment. Such functions include, but are not limited to, a coding function in which the RNA acts as a messenger RNA encoding a sequence which, translated by the host cell, results in synthesis of a peptide or protein having useful or desired properties. The RNA segment may also be structural, as for example in ribosomal RNA, it may be regulatory, as for example with small nuclear RNAs or anti-sense RNA, or it may be catalytic. A particularly interesting function is provided by anti-sense RNA, sometimes termed (−) strand RNA, which is in fact a sequence complementary to another RNA sequence present in the target cell which can, through complementary base pairing, bind to and inhibit the function of the RNA in the target cell. An exogenous RNA segment can be a complete or partial coding sequence.

Various aspects of the stages outlined in the Summary section can be modified as needed, depending upon specific aspects of the virus selected as the transforming agent and of the RNA segment to be inserted. For example, if the inserted gene is in the form of messenger-sense RNA to be directly translated by the transformed cell, the gene must be free of intervening, nontranslated sequences, such as introns. On the other hand, the inserted gene need not be a naturally occurring gene, but it may be modified, it may be a composite of more than one coding segment, or it may encode more than one protein. Combining insertions and deletions in order to control the total length or other properties of the modified RNA molecule may also modify the RNA. The inserted non-viral gene may be either prokaryotic or eukaryotic in origin as long as it is in a form which can be directly translated by the translation machinery of the recipient cell. Eukaryotic genes containing introns within the coding sequence must therefore be inserted in the form of a cDNA copy of the eukaryotic messenger RNA encoding the gene. The inserted gene may contain its own translation start signals, for example, a ribosomal binding site and start (AUG) codon, or it may be inserted in a manner which takes advantage of one or more of these components preexisting in the viral RNA to be modified. Certain structural constraints must be observed to preserve correct translation of the inserted sequence, according to principles well understood in the art. For example, if it is intended that the exogenous coding segment be combined with an endogenous coding segment, the coding segment to be inserted must be inserted in reading frame phase therewith and in the same translational direction.

Host

A cell, tissue or organism capable of being infected by and capable of replicating a nucleic acid such as a plant viral nucleic acid and which is capable of being infected by a virus containing the viral vector or viral nucleic acid. As used herein, host is intended to include generally whole plant, plant protoplast, plant cell, and plant tissues, plant organ or plant part such as root, stem leaf, flower or seed.

Infection

The ability of a virus to transfer its nucleic acid to a host or introduce a viral nucleic acid into a host, wherein the viral nucleic acid is replicated, viral proteins are synthesized, and new viral particles assembled. In this context, the terms "transmissible" and "infective" are used interchangeably herein. The term is also meant to include the ability of a selected nucleic acid sequence to integrate into a genome, chromosome or gene of a target organism.

The term "non-viral" is used here in a special sense to include any RNA segment which is not normally contained within the virus whose modification is exploited for effecting gene transfer and is therefore used synonymously with "exogenous". Therefore, a gene derived from a different virus species than that modified is included within the meaning of the terms "non-viral" and "exogenous" for the purposes of describing the invention. For example, a non-viral gene as the term is used herein could include a gene derived from a bacterial virus, an animal virus, or a plant virus of a type distinguishable from the virus modified to effect transformation. In addition, a non-viral gene may be a structural gene derived from any prokaryotic or eukaryotic organism. It will be understood by those ordinarily skilled in the art that there may exist certain genes whose transfer does not result in obvious phenotypic modification of the host cell. A phenotypic modification may occur, for example, if the translation product of the non-viral gene is toxic to the host cell, is degraded or processed in a manner which renders it non-functional or possesses structural features which render it impossible for the host cell to translate in sufficient quantities to confer a detectable phenotype on the transformed cells. However, the invention does not depend upon any specific property of an RNA segment or gene being transferred. Therefore, the possible existence of RNA segments or genes which fail to confer a readily observable phenotypic trait on recipient cells or plants is irrelevant to the invention and in any case will be readily recognizable by those of ordinary skill in the art without undue experimentation.

Plant host

A cell, tissue or organism capable of replicating a nucleic acid such as a plant viral nucleic acid and which is capable of being infected by a virus containing the viral vector or viral nucleic acid. As used herein, plant host is intended to include whole plant, plant cell, and plant tissues, plant organ or plant part such as root, stem leaf, flower or seed.

Phenotypic Trait

An observable, measurable or detectable property resulting from the expression or suppression of a gene or genes. Phenotype includes both easily observable traits and biochemical processes.

Plant Cell

The structural and physiological unit of plants, consisting of a protoplast and the cell wall.

Plant Organ

A distinct and visibly differentiated part of a plant, such as root, stem, leaf or embryo.

Plant Tissue

Any tissue of a plant in planta or in culture. This term is intended to include a whole plant, plant cell, plant organ, protoplast, cell culture, or any group of plant cells organized into a structural and functional unit.

Positive-sense Inhibition

A type of gene regulation based on inhibition of gene expression believed to be due to the presence in a cell of an RNA molecule substantially homologous to at least a portion of the mRNA being translated. The RNA molecule can be an exogenous coding sequence carried by an RNA viral vector of the type discussed herein.

Promoter

The 5'-flanking, non-coding sequence substantially adjacent a coding sequence which is involved in the initiation of transcription of the coding sequence.

Protoplast

As used herein means an isolated plant cell without some or all of its cell wall.

Single component virus

Is a virus having a single nucleic acid sequence; unipartite. The single component virus is contrasted with the multicomponent virus, which has more than one nucleic acid component. Each component of a multicomponent virus is individually encapsidated, separate from the other(s).

Subgenomic Promoter

A promoter of a subgenomic mRNA of a viral nucleic acid. Plant viral nucleic acid can be modified to contain an exogenous nucleic acid sequence under the control of a subgenomic promoter.

Systemic Infection

Denotes infection throughout a substantial part of an organism including mechanisms of spread other than mere direct cell inoculation but rather including transport from one infected cell to additional cells either nearby or distant.

Viral Vector

A self-replicating RNA or DNA molecule derived from a virus which transfers an RNA or DNA segment between cells, such as bacteria, yeast, plant, or animal cells and contains an exogenous DNA or RNA segment to be expressed in the host.

A first embodiment demonstrates a capped viral vector having a single base inserted at the 5' terminus of the viral sequence.

Another embodiment demonstrates a capped viral vector having a sequence of bases inserted at the 5' terminus of the viral sequence.

In another embodiment, a host cell is infected by a capped viral vector which has a single base inserted at the 5' terminus of the viral sequence. The capped viral vector is able to infect, to reproduce, to systemically infect the host plant, and to express an exogenous RNA segment.

In another embodiment, a host cell is infected by a capped viral vector having a sequence of bases inserted at the 5' terminus of the viral sequence. The capped viral vector is able to infect the host cell, to reproduce, to systemically infect the host plant, and to express an exogenous RNA segment.

Another embodiment demonstrates an uncapped viral vector.

In another embodiment, a host cell is infected by an uncapped viral vector. The uncapped viral vector is able to reproduce, to systemically infect the host and to express an exogenous RNA segment.

Another embodiment demonstrates an uncapped viral vector having a single base inserted at the 5' terminus of the viral sequence.

In another embodiment, a host cell is infected by an uncapped viral vector having a single base inserted at the 5' terminus of the viral sequence. The uncapped viral vector is able to reproduce, to systemically infect the host and to express an exogenous RNA segment.

Another embodiment demonstrates an uncapped viral vector having a sequence of bases inserted at the 5' terminus of the viral sequence.

In another embodiment, a host cell is infected by an uncapped viral vector having a sequence of bases inserted at the 5' terminus of the viral sequence. The uncapped viral vector is able to reproduce, to systemically infect the host and to express an exogenous RNA segment.

An exogenous RNA segment may be inserted at any convenient insertion site provided the insertion does not disrupt a sequence essential for replication of the RNA within the host cell. For example, Dual Heterologous Subgenomic Promoter Expression System (DHSPES) in a plus stranded RNA vector has two subgenomic promoters. An exogenous RNA segment can be expressed in this system by inserting the exogenous gene at the 3' end of one of the subgenomic promoters. This system is described in U.S. Pat. Nos. 5,316,931, 5,811,653, 5,589,367 and 5,866,785, the disclosure of which is incorporated by reference. An exogenous RNA segment under the control of a subgenomic promoter will be expressed in the host plant. Each heterologous subgenomic promoter is capable of transcribing or expressing adjacent genes or nucleic acid sequences in the plant host and incapable of recombination with each other and with native subgenomic promoters. One or more non-native nucleic acids may be inserted adjacent to the native plant viral subgenomic promoter or the native and non-native plant viral subgenomic promoters if more than one nucleic acid sequence is included. Moreover, it is specifically contemplated that two or more heterologous non-native subgenomic promoters may be used. The exogenous RNA segment may be transcribed or expressed in the host plant under the control of the subgenomic promoter to produce the products of the exogenous RNA segment.

A virus, whose coat protein is not essential for replication, an exogenous RNA segment may be inserted within or substituted for the region, which normally codes for coat protein. As desired, regions which contribute to undesirable host cell responses may be deleted or inactivated, provided such changes do not adversely effect the ability of the RNA to be replicated in the host cell. For many single component viruses, a reduction in the rate of normal RNA replication is tolerable and will in some instances be preferred, since the amount of RNA produced in a nonnal infection is more than enough to saturate the ribosomes of the transformed cell.

The transformation process itself can be carried out by any means whereby RNA can be introduced into cells, whole plants, plant tissues or protoplasts. The RNA alone or encapsidated in a virus particle can infect host cells, except that the modified viral RNA containing a non-viral RNA segment is substituted for its counterpart in a normal infection. Any other suitable means for introducing RNA into target cells such as microinjection may be used. Other variables of the infection process, such as pretreatment of the recipients, use of encapsidated or unencapsidated RNA, are matters of choice which those of ordinary skill in the art will be able to manipulate to achieve desired transformation efficiency in a given situation. For instance, the choice of single component plant RNA virus to be modified to achieve gene expression in a given plant variety will depend upon known host range properties of single component plant RNA viruses. For example, TMV infects a variety of Nicotiana species and their related domesticated relatives.

Plant cells, which are infected in culture, will normally remain transformed as the cells grow and divide since the RNA components are able to replicate and thus become distributed to daughter cells upon cell division. Plants regenerated from phenotypically modified cells, tissues or protoplasts remain phenotypically modified. Similarly, plants transformed as seedlings remain transformed during growth. Timing of application of the transforming components will be governed by the result that is intended and by variations in susceptibility to the transforming virus or viral RNA during various stages of plant growth.

Using the various embodiments of the invention, an exogenous segment RNA sequence can be expressed in a host by adapting the invention to any of a variety of embodiments set forth below for expressing an exogenous RNA segment. In one embodiment, an exogenous RNA segment is introduced into a plant host by way of a viral nucleic acid which comprises a native plant viral subgenomic promoter, a plant viral coat protein coding sequence, and at least one exogenous RNA segment under the control of a non-native subgenomic promoter.

In a second embodiment, plant viral nucleic acid sequences used in the method of the present invention are characterized by the deletion of the native coat protein coding sequence in favor of a non-native plant viral coat protein coding sequence for the purpose of increasing host range. A non-native promoter, which could be the subgenomic promoter of the non-native coat protein coding sequence, controls expression of the non-native coat protein coding sequence. The non-native coat protein coding sequence is capable of expression in the plant host, of packaging the recombinant plant viral nucleic acid, and ensuring a systemic infection of a permissive host by the recombinant plant viral nucleic acid. The recombinant plant viral nucleic acid may contain one or more additional native or non-native subgenomic promoters.

In a third embodiment, plant viral nucleic acids are used in the present invention wherein the native coat protein coding sequence is placed adjacent to a non-native subgenomic promoter.

In a fourth embodiment, plant viral nucleic acids are used in the present invention wherein the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the product of the non-native nucleic acid. Alternatively, a non-native coat protein coding sequence may replace the native coat protein coding sequence.

In another embodiment, a viral expression vector contains an exogenous RNA segment encoding a polyprotein. At least one protein of the polyprotein is non-native to the vector. The non-native protein is released from the polyprotein by proteolytic processing catalyzed by at least one protease in the polyprotein. The vector comprises: a) at least one promoter; b) cDNA having a sequence which codes for at least one polyprotein from a polyprotein-producing virus; c) at least one unique restriction site flanking a 3' terminus of the cDNA; and a cloning vehicle.

Additional embodiments use a viral expression vector encoding at least one protein non-native to the vector that is released from at least one polyprotein expressed by the vector by proteolytic processing. The vector comprises at least one promoter, cDNA having a sequence which codes for at least one polyprotein from a polyprotein-producing virus, may contain at least one restriction site flanking a 3' terminus of said cDNA and a cloning vehicle. Preferred embodiments include using a potyvirus as the polyprotein-producing virus, and especially preferred embodiments may use TEV (tobacco etch virus). A more detailed description of such vectors useful according to the method of the present invention may be found in U.S. Pat. Nos. 5,491,076 and 5,766,885 to James C. Carrington et al. which are incorporated herein by reference.

In yet other embodiments, recombinant plant viruses are used which encode for the expression of a fusion between a plant viral coat protein and the amino acid product of the exogenous RNA of interest. Such a recombinant plant virus provides for high level expression of a nucleic acid of interest. The location or locations where the viral coat protein is joined to the amino acid product of the nucleic acid of interest may be referred to as the fusion joint. A given product of such a construct may have one or more fusion joints. The fusion joint may be located at the carboxyl terminus of the viral coat protein or the fusion joint may be located at the amino terminus of the coat protein portion of the construct. In instances where the nucleic acid of interest is located internal with respect to the 5' and 3' residues of the nucleic acid sequence encoding for the viral coat protein, there are two fusion joints. That is, the nucleic acid of interest may be located 5', 3', upstream, downstream or within the coat protein. In some embodiments of such recombinant plant viruses, a "leaky" start or stop codon may occur at a fusion joint which sometimes does not result in translational termination. A more detailed description of some recombinant plant viruses according to this embodiment of the invention may be found in U.S. Pat. No. 5,977,438, the disclosure of which is incorporated herein by reference.

In another embodiment an exogenous gene can be introduced into the site of the coat protein gene of Potato virus X. Alternatively, an exogenous gene can be added to the PVX genome by partial duplication of the viral genome, so that expression of the exogenous gene is under the control of the same promoter sequence that controls production of the coat protein gene. Chapman, S. et al., *The Plant Journal* (1992) 2(4): 549–557.

Those skilled in the art will understand that these embodiments are representative only of many constructs which may be useful to produce localized or systemic expression of nucleic acids in host organisms such as plants. All such constructs are contemplated and intended to be within the scope of the present invention.

The following examples illustrate the principles of the invention as applied to modification of TMV and the use of modified TMV containing a gene coding for green fluorescent protein (GFP) in the phenotypic transformation of Nicotiana plants and protoplasts. The following examples utilize many techniques well known and accessible to those skilled in the arts of molecular biology, cloning, plant cell biology, plant virology and plant tissue culture. Such methods are fully described in one or more of the cited references if not described in detail herein. Unless specified otherwise, enzymes were obtained from commercial sources and were used according to the vendor's recommendations or other variations known to the art. Those in the art also know reagents, buffers and culture conditions and reaction conditions for various enzyme-catalyzed reactions. Reference works containing such standard techniques include the following: R. Wu, ed. (1979) *Meth. Enzymol.* 68; R. Wu et al., eds. (1983) *Meth. Enzymol.* 100, 101; L. Grossman and K. Moldave, eds. (1980) *Meth. Enzymol.* 65; J. H. Miller (1972) Experiment's in Molecular Genetics; R. Davis et al. (1980) Advanced Bacterial Genetics; R. F. Schleif and P. C. Wensink (1982) Practical Methods in Molecular Biology; and T. Maniatis et al. (1982) Molecular Cloning.

Textual use of the name of a restriction endonuclease in isolation, e.g., "EcoRV" or "SphI" refers to use of that enzyme in an enzymatic digestion, except in a diagram where it can refer to the site of a sequence susceptible to action of that enzyme, e.g., a restriction site. In the text, restriction sites are indicated by the additional use of the word "site", e.g., "EcoRV site". The additional use of the word "fragment", indicates a linear double-stranded DNA molecule having ends generated by action of the named enzyme (e.g., a restriction fragment). A phrase such as, "EcoRV/SphI" fragment" indicates that the restriction fragment was generated by the action of two different enzymes, here EcoRV and SphI, the two ends resulting from the action of different enzymes. Note that the ends will have the characteristics of being either sticky (i.e., having a single strand of protrusion capable of base pairing with a complementary single-stranded oligonucleotide) or blunt (i.e., having no single-stranded protrusion). The specificity of a sticky end will be determined by the sequence of nucleotides comprising the single-stranded protrusion, which in turn is determined by the specificity of the enzyme, which produces it.

All plasmids are designated by a sequence of letters and numbers prefaced by a lower case "p", for example, pBTI1037, pBTI1056, pBTI1057, pBTI SBS60, pBTI SBS60-29, or pBTI1056-GTN 28. Certain steps of cloning, selection and vector increase employed strains of *E. Coli.* While the strains used herein have been designated, there are many equivalent strains, available to the public that may be employed. The use of a particular microorganism as a substitute for a strain designated herein is a matter of routine choice available to those of ordinary skill in the art, according to well-known principles.

EXAMPLES

Example 1
Infectivity of Uncapped and Capped Transcripts

This example demonstrates the production of highly infectious viral vector transcripts containing 5' nucleotides with reference to the virus vector.

1. Insertion of base or base sequence at the 5' end of the TMV cDNA.

Nucleotides were added between the transcriptional start site for in vitro transcription, in this case the T7 promoter, and the start of the cDNA of TMV in order to maximize transcription product yield and possibly obviate the need to cap virus transcripts to insure infectivity. The relevant sequence is the T7 promoter indicated in shorthand as TATA, followed by the transcription start site "G", followed by TATTTT . . . , which is the continuation of the cDNA of TMV. These are put together as . . . TATAG^TATTTT . . . (SEQ ID NO: 1). The base preceding the "^" is the start site for transcription of the cDNA. The bolded letter is the first base followed by TATTTT . . . of the TMV cDNA. Three approaches were taken:

1) addition of G, GG or GGG between the start site of transcription and the first base of the cDNA (as in . . . TATAG^GTATTTT . . . and associated sequences);

| | | |
|---|---|---|
| I. | starting point | ...TATAG^TATTTT... (SEQ ID NO: 1) |
| II. | addition of G | ...TATAG^GTATTTT... (SEQ ID NO: 2) |
| III. | addition of GG | ...TATAG^GGTATTTT... (SEQ ID NO: 3) |
| IV. | addition of GGG | ...TATAG^GGGTATTTT... (SEQ ID NO: 4) |

2) addition of G and a random base (GN). As used herein, [N=A, T, C, or G]. VI represents addition of two random bases (N2). VII represents a G and two random bases (GNN). VIII represents three random bases (N3) between the start site of transcription and the TMV cDNA.

| | | |
|---|---|---|
| V. | addition of GN | ...TATAG^NGTATTTT... (SEQ ID NO: 5) |
| VI. | addition of N2 | ...TATAGN^NNTATTTT... (SEQ ID NO: 6) |
| VII. | addition of GNN | ...TATAG^NNGTATTTT... (SEQ ID NO: 7) |
| VIII. | addition of NNN | ...TATAGN^NNTATTTT... (SEQ ID NO: 8) |
| IX. | addition of GNG | ...TATAGG^NGTATTT... (SEQ ID NO: 9) |

3) addition of a GT and a single random base (GTN) between the start site of transcription and the TMV cDNA ( . . . TATAG^TNGTATTTT, SEQ ID NO: 10 . . . and associated sequences).

| | | | |
|---|---|---|---|
| X. | addition of GTN | ...TATAG^TNGTATTTT... | (SEQ ID NO:11) |
| XI. | addition of GTC, | ...TATAG^TCGTATTTT... | (SEQ ID NO:12) |
| XII. | addition of $(GTN)_2$ | ...TATAG^TNGTNGTATTTT... | (SEQ ID NO:13) |
| XIII. | addition of $(GTN)_4$ | ...TATAG^TNGTNGTNGTNGTATTTT... | (SEQ ID NO:14) |
| XIV. | addition of GTATTT | ...TATAG^TATTTGTATTTT,... | (SEQ ID NO:15) |

The use of random bases was based on the hypothesis that a particular base may be best suited for an additional nucleotide attached to the cDNA, since it will be complementary to the normal nontemplated base incorporated at the 3'-end of the TMV (−) strand RNA. This allows for more ready mis-initiation and restoration of wild type sequence. The GTN would allow the mimicking of two potential sites for initiation, the added and the native sequence, and facilitate more ready mis-initiation of transcription in vivo to restore the native TMV cDNA sequence. Approaches included cloning GFP expressing TMV vector sequences into vectors containing:

1) an extra G,
2) an extra GG or
3) an extra GGG bases using standard molecular biology techniques.

Likewise, full length PCR of TMV expression clone 1056 was done to add

4) N2,

5) N3 and

6) GTN bases between the T7 promoter and the TMV cDNA.

Construction of Plasmid

DNA oligonucleotide primers were synthesized to contain a 5' EcoRV site, an entire T7 RNA polymerase promoter, any extra nucleotides, and the 5'-terminal 20 bases of the TMV cDNA. These primers contain in the position for extra nucleotides, either none for constructs with sequence . . . TATAG^TATTT . . . , a "G" for constructs with sequence . . . TATAG^GTATTT . . . , a "GN" for constructs with sequence . . . TATAG^NGTATTT . . . or a "GTN" for constructs with sequence . . . TATAG^TNGTATTT . . . , where ^ indicates the base preceding is the start site for transcription.

Examples of 5' primers used to construct variant TMV constructs:

5' GGCGATATC<u>TAATACGACTCACTATA</u>GTNGTATTTTACA
ACAATTACC    (SEQ ID NO:16)

5' GGCGATATC<u>TAATACGACTCACTATA</u>GNGTATTTTACAA
CAATTACC    (SEQ ID NO:17)

5' GGCGATATC<u>TAATACGACTCACTATA</u>GNNGTATTTTACA
ACAATTACC    (SEQ ID NO:18)

5' GGCGATATC<u>TAATACGACTCACTATA</u>GNNNGTATTTTTAC
AACAATTACC    (SEQ ID NO:19)

5'GGCGATATC<u>TAATACGACTCACTATA</u>GTNGTNGTATTTTT
ACAACAATTAC    (SEQ ID NO:20)

GATATC is the EcoRV restriction enzyme recognition site. Underlined is the T7 RNA polymerase promoter. The added bases between the T7 promoter and the TMV cDNA are in bold. The 5' 20 bases of TMV cDNA are shown following the added bases.

We used the following 3'-primer, which anneals to TMV nucleotides 1034 to 1056:

<u>5' CACTATCTACACTTTTATGGGCC</u>    (SEQ ID NO:21).

These 5' primers and a 3' primer containing sequences in the TMV cDNA surrounding the SphI site at position 445 were used to amplify a portion of the TMV cDNA (~500 bp in length) by the polymerase chain reaction (PCR). The PCR products were purified by agarose gel electrophoresis and standard gel extraction procedures and digested with EcoRV and SphI. The DNA fragments were then ligated into a plasmid digested with EcoRV and SphI. The digestion removed the identical portion of the genome and replaced it with the PCR fragment. The recombinants were analyzed by agarose gel electrophoresis and by DNA sequencing of the 5' end of the TMV cDNA and T7 promoter junction. These plasmids were then used for in vitro transcription using T7 RNA polymerase.

In vitro Transcription

Several TMV-based virus expression vectors were initially used in these studies. Vector pBTI 1056 contains the T7 promoter (underlined) followed directly by the virus cDNA sequence ( . . . <u>TATA</u>GTATT . . . ), and vector pBTI SBS60-29 contains the T7 promoter followed by an extra guanine residue, then by the virus cDNA sequence ( . . . <u>TATA</u>GGTATT . . . ). Both expression vectors express an exogenous cycle 3 shuffled green fluorescent protein (GFPc3) in localized infection sites and systemically infected tissue of infected plants.

Transcriptions of each plasmid were carried out in the absence of cap analogue (uncapped) or in the presence of 8-fold greater concentration of RNA cap analogue than rGTP (capped). "r" means ribosomal.

Cap Transcriptions 1.2 μl 20 mM rATP, rCTP, rUTP, 2 mM rGTP solution

2 μl 10 mM RNA cap analogue (New England Biolabs catalog #1404, methylated cap analogue)

1 μl Rnase Inhibitor 20 U (Promega N2511)

1 μl T7 RNA polymerase 30 U (Ambion 2085)

2 μl T7 RNA polymerase buffer (Ambion n supplied with enzyme)

0.5 mg of transcriptional plasmid DNA

Raise volume to 20 μl

Incubate at 37° C. for 1.5 hours

Analyze by agarose gel electrophoresis of 0.5 μl solution.

Non-Cap Transcriptions 1.2 μl 20 mM rATP, rCTP, rUTP 4.3 μl 20 mM rGTP

1 μl Rnase Inhibitor 20 U (Promega N2511)

1 μl T7 RNA polymerase 30 U (Ambion 2085)

2 μl T7 RNA polymerase buffer (Ambion, supplied with enzyme)

0.5 mg of transcriptional plasmid DNA

Raise volume to 20 μl

Incubate at 37° C. for 1.5 hours.

Analyze by agarose gel electrophoresis of 0.5 μl solution.

There are other methods for transcription. This method is not intended to be limiting. The volume of rGTP is also not limiting. Other volumes can be used. While methylated cap is used in these experiments, for purposes of this invention, unmethylated cap, New England Biolabs catalog #1407, may also be used if cap is desired.

Description of Vectors pBTI SBS5, pBTI 1056, pBTI SBS60, pBTI SBS60-29, and pBTI 1056 GTN-28

Vector p30BGFPc3 is the base vector or starting point. Each clone comparison is outlined below. pBTI SBS5, pSBS60 and p1056 are compared with p30BGFPc3. P1056GTN-28 is compared with p1056 and pSBS60-29 s compared with pSBS60. "nt" means nucleotide. "aa" means amino acid.

| 1. pBTI SBS5 (pBTI 1057) SEQ DATA vs pBTI 30BGFPc3 (pBTI 1037) | | | |
|---|---|---|---|
| 8 nt changes | | | 4 aa changes |
| nt 1138 | pBTI SB | S5 A to G mutation | (E to G change of aa 357 of 126K protein) |
| nt 1268 | | T to C | (silent) |
| nt 2382 | pBTI SBS5 | A to G mutation | (K to E change of aa 772 of 126K protein) |
| nt 3120 | | T to C mutation | (silent) |
| nt 3632 | pBTI SBS5 | G to A mutation | (silent) |
| nt 5213 | | C to T mutation | (T to I change of aa 104 of 30K protein) |
| nt 5303 | pBTI SBS5 | A to G mutation | (K to R change of aa 134 of 30K protein) |
| nt 5896 | | C to A mutation | (silent) |

| 2. pBTI SBS60 SEQ DATA vs. pBTI 30BGFPc3 (pBTI 1037) | | | |
|---|---|---|---|
| 6 nt changes | | | 1 aa change |
| nt 1268 | | T to C | (silent) |
| nt 3120 | | T to C mutation | (silent) |
| nt 4100 | pBTI SBS60 | T to C mutation | (silent) |
| nt 5213 | | C to T mutation | |

-continued

| | | (T to I change of aa 104 of 30K protein, shared with pBTI SBS5) | |
|---|---|---|---|
| nt 5634 | pBTI SBS60 | A to G mutation | (silent) |
| nt 5896 | | C to A mutation | (silent) |

There is no nucleotide "nt" sequence inserted between the T7 promoter sequence and the 5' most base of the TMV U1 cDNA to form ( . . . TATAGTATTTT . . . ). In the short hand used herein . . . TATA represents the T7 promoter, there is no base or sequence of bases inserted between the T7 promoter and the GTATTTT . . . represents the 5' most bases of the TMV U1 cDNA.

| 3. pBTI 1056 SEQ DATA vs. pBTI 30BGFPc3 (pBTI 1037) | |
|---|---|
| 2 nt changes | 2 aa change |
| nt 5213 C to T mutation | (T to I change of aa 104 of 30 k) |
| nt 5402 G to A mutation | (R to K change of aa 167 of 30 k) |

There is no nt sequence inserted between the T7 promoter sequence and the 5' most base of the TMV U1 cDNA to form ( . . . TATAGTATTTT . . . ). In the short hand used herein . . . TATA represents the T7 promoter, there is no base or sequence of bases inserted between the T7 promoter and the GTATTTT . . . represents the 5' most bases of the TMV U1 cDNA. pBTI1056.

4. pBTI 1056 GTN-28 SEQ DATA vs. pBTI 1056 nt sequence is GTC inserted between the T7 promoter sequence and the 5' most base of the TMV U1 cDNA to form ( . . . TATAGTCGTATTTT . . . ). In the short hand used herein . . . TATA represents the T7 promoter, GTC is the inserted sequence of nucleotides, and GTATTTT . . . represents the 5' most bases of the TMV U1 cDNA 5. pBTI SBS 60-29 SEQ DATA vs. pBTI SBS60 nt G is inserted between the T7 promoter sequence and the 5' most base of the TMV U1 cDNA to form ( . . . TATAGGTATTTT . . . ). In the short hand used herein . . . TATA represents the T7 promoter, G is the inserted nucleotide, and GTATTTT . . . represents the 5' most bases of the TMV U1 cDNA.

Table 1 summarizes the vectors and host plants used in the following experiments; the nucleotide sequence of each vector which contains the T7 promoter and the start of the cDNA of TMV is listed in the Table.

TABLE 1

| Viral Vector | 5' nucleotide sequence | Cap +, − | Host Plant | Foreign Gene | Plant tissue |
|---|---|---|---|---|---|
| pBTI1056 | TATAGTATTTT | + and − | NB and NB30K | GFPc3 | leaf |
| pBTISBS60-29 | TATAGGTATTTT | + and − | NB and NB30K | GFPc3 | leaf |
| pBTISBS60 | TATAGTATTTT | + and − | NB | GFPc3 | proto-plasts |
| pBTI1056-GTN28 | TATAGTCGTATTTT | + and − | NB and NB30K | GFPc3 | leaf |

Data of Cap and Non-cap Transcriptions of pBTI1056 and PBTI SBS60-29

*Nicotiana tabacum* plants were infected with either capped or uncapped transcriptions (as described above) of pBTI 1056 and pBTI SBS60-29. Transcriptions were mixed with abrasive and inoculated on expanded older leaves of a wild type *Nicotiana benthamiana* (Nb) plant and a Nb plant expressing a TMV U1 30 k movement protein transgene (Nb 30K). Four days post inoculation (dpi), long wave UV light was used to judge the number of infection sites on the inoculated leaves of the plants. Systemic, noninoculated tissues were monitored from 4 dpi on for appearance of systemic infection indicating vascular movement of the inoculated virus. Table 2 shows the results of one representative experiment. An extra G, . . . TATAG^GTATTTT . . . is found to be well tolerated as an additional 5' nucleotide on the 5' end of TMV vector RNA transcripts. Both capped and uncapped transcripts are infectious. Extra guanine residues located between the T7 promoter and the first base of a virus cDNA as demonstrated by pBTISBS60-29 lead to an increased amount of RNA transcript.

TABLE 2

| | Local infection sites | | Systemic Infection | |
|---|---|---|---|---|
| Construct | Nb | Nb 30K | Nb | Nb 30K |
| pBTI1056 | | | | |
| Capped | 5 | 6 | yes | yes |
| Uncapped | 0 | 5 | no | yes |
| pBTI SBS60-29 | | | | |
| Capped | 6 | 6 | yes | yes |
| Uncapped | 1 | 5 | yes | yes |

Results of Cap and Non-cap Transcriptions of pBTI SBS60

*Nicotiana tabacum* protoplasts were infected with either capped or uncapped transcriptions (as described above) of pBTI SBS60 which contains the T7 promoter followed directly by the virus cDNA sequence (TATAGTATT . . . ). This expression vector also expresses the GFPc3 gene in infected cells and tissues. *Nicotiana tabacum* protoplasts were transfected with 1 l of each transcription. Approximately 36 hours post infection transfected protoplasts were viewed under UV illumination and cells showing GFPc3 expression. Approximately 80% of cells transfected with the capped pBTI SBS60 transcripts showed GFP expression while 5% of cells transfected with uncapped transcripts showed GFP expression. These experiments were repeated with higher amounts of uncapped inoculum. In this case a higher proportion of cells, >30% were found to be infected at this time with uncapped transcripts, where >90% of cells infected with greater amounts of capped transcripts were scored infected.

Data of Cap and Non-cap Transcriptions of pBTI1056 GTN-28

TMV-based virus expression vector pBTI 1056 GTN-28 contains the T7 promoter (underlined) followed GTC bases (bold) then the virus cDNA sequence ( . . . TATAGTCGTATT, SEQ ID NO: 10, . . . ). This expression vector expresses the exogenous cycle 3 shuffled green fluorescent protein (GFPc3) in localized infection sites and systemically infected tissue of infected plants. This vector was transcribed in vitro in the presence (capped) and absence (uncapped) of cap analogue as described above. Transcriptions were mixed with abrasive and inoculated on expanded older leaves of a wild type *Nicotiana benthamiana* (Nb) plant and a Nb plant expressing a TMV U1 30k movement protein transgene (Nb 30K). Four days post inoculation (dpi) long wave UV light was used to judge the number of infection sites on the inoculated leaves of the plants. Systemic, non-inoculated tissues were monitored from 4 dpi on for appearance of systemic infection indicating vascular movement of the inoculated virus. Table 3 shows data from two representative experiments at 11 dpi.

TABLE 3

| Construct | Local infection sites | | Systemic Infection | |
|---|---|---|---|---|
| | Nb | Nb 30K | Nb | Nb |
| 30K Experiment 1 pBTI1056 GTN-28 | | | | |
| Capped | 18 | 25 | yes | yes |
| Uncapped | 2 | 4 | yes | yes |
| Experiment 2 pBTI1056 GTN-28 | | | | |
| Capped | 8 | 12 | yes | yes |
| Uncapped | 3 | 7 | yes | yes |

Extra GTN such as GTC residues located between the T7 promoter and the first base of a virus cDNA (pBTI 1056 GTN-28) lead to increased amount of RNA transcript as predicted by previous work with phage polymerases. These polymerases tend to initiate more efficiently at . . . <u>TATAG</u>TNG or . . . <u>TATAG</u>TCG than . . . <u>TATAG</u>. This has an indirect effect on the relative infectivity of uncapped transcripts in that greater amounts are synthesized per reaction resulting in enhanced infectivity.

Discussion and Conclusions

The foregoing examples demonstrate that, contrary to the practiced art in scientific literature and in issued patents (Ahlquist et al., U.S. Pat. No. 5,500,360), uncapped transcripts for virus expression vectors are infective in both whole plants and in plant cells, however with much lower specific infectivity. Therefore, capping is not a prerequisite for establishing an infection of a virus expression vector in plants; capping just increases the efficiency of infection. This reduced efficiency can be overcome, to some extent, by providing excess in vitro transcription product in an infection reaction for plants or plant cells. These data further support the claims concerning the utility of uncapped transcripts to initiate infections by plant virus expression vectors and further demonstrates that the introduction of extra, non-viral nucleotides at the 5'-end of in vitro transcripts does not preclude infectivity of uncapped transcripts. We conclude that while many similarities between plant viruses can be cited, there are specific differences between the Brome mosaic virus and the Tobamovirus group which provide specific advantages to using a single-component Tobamovirus-derived vector. The results also show that reduced efficiency can be overcome, to some extent, by using a transgenic host plant or transgenic host plant cell, which expresses one or more RNA binding viral proteins. The expression of the 30K movement protein of TMV in transgenic plants also has the unexpected effect of equalizing the relative specific infectivity of uncapped verses capped transcripts. The mechanism behind this effect is not fully understood.

Further modifications and improvements following and embodying the teachings and disclosures herein are deemed to be within the scope of the invention, as set forth in the appended claims.

Although the invention has been described with reference to the presently preferred embodiments, it should be understood that various modifications could be made without departing from the spirit of the invention. Further modifications and improvements following and embodying the teachings and disclosures herein are deemed to be within the scope of the invention, as set forth in the appended claims.

What is claimed is:

1. A capped RNA molecule capable of infecting a host plant cell comprising:
   a) a viral sequence comprising a cis-acting viral replication element derived from a single component (+) strand RNA plant virus;
   b) a sequence of one to three intervening bases located between a cap and the 5' terminus of the viral sequence;
   c) an exogenous RNA segment capable of expressing its function in a plant host cell; wherein said exogenous RNA segment is located in a region of said capped RNA molecule able to tolerate said exogenous RNA segment without disrupting RNA replication of said capped RNA molecule; and wherein said capped RNA molecule is capable of replication in the absence of a trans-acting viral replication element.

2. The RNA of claim 1, wherein the exogenous RNA segment codes for a peptide or protein.

3. The RNA of claim 1, wherein the exogenous RNA segment comprises an antisense RNA.

4. The RNA of claim 1, wherein the exogenous RNA segment comprises a structural RNA.

5. The RNA of claim 1, wherein the exogenous RNA segment comprises a regulatory RNA.

6. The RNA of claim 1, wherein the exogenous RNA segment comprises a RNA having catalytic properties.

7. The RNA molecule of claim 1, wherein the cis-acting viral replication element is derived from a tobacco mosaic virus.

8. The RNA molecule of claim 1, encapsidated with viral coat protein.

9. The capped RNA molecule of claim 1, comprising a single intervening base located between the cap and the 5' terminus of the viral sequence.

10. The capped RNA molecule of claim 1, comprising a sequence of two intervening bases located between the cap and the 5' terminus of the viral sequence.

11. The capped RNA molecule of claim 1, comprising a sequence of three intervening bases located between the cap and the 5' terminus of the viral sequence.

12. The capped RNA molecule of claim 1, wherein said (+) strand RNA plant virus is a tobamovirus.

13. The capped RNA molecule of claim 1, wherein said plant host is Nicotiana.

14. A DNA transcription vector comprising cDNA having one strand complementary to a capped RNA molecule capable of infecting a host plant cell, said capped RNA molecule comprising:
   a) a viral sequence comprising a cis-acting viral replication element derived from a single component (+) strand RNA plant virus;
   b) a sequence of one to three intervening bases located between the cap and the 5' terminus of the viral sequence; and
   c) an exogenous RNA segment capable of expressing its function in a plant host cell in a region of said capped RNA molecule able to tolerate said exogenous RNA segment without disrupting RNA replication of said capped RNA molecule; and wherein said capped RNA molecule is capable of replication in the absence of a trans-acting viral replication element.

15. A DNA transcription vector selected from the group consisting of pBTI1037, pBTI SBS60, pBTI SBS60-29, pBTI1056, pBTI1057, and pBTI1056-GTN28.

16. A method of modifying a host plant cell phenotypically, said method comprising introducing into the cell a capped RNA molecule capable of infecting said host cell, wherein said capped RNA molecule comprises:
   a) a cis-acting viral replication element derived from a single component single component (+) strand RNA plant virus;
   b) the same capped 5' end as said virus;
   c) a sequence of one to three intervening bases located between the cap and the 5' terminus of the viral sequence, and an exogenous RNA segment in a region of said capped RNA molecule able to tolerate said exogenous RNA segment without disrupting RNA replication of said capped RNA molecule, and wherein said capped RNA molecule is capable of replication in the absence of a trans-acting viral replication element; whereby the exogenous RNA segment confers a detectable trait in the host cell, thereby modifying said host cell.

17. The method of claim 16, wherein the exogenous RNA segment codes for a peptide or protein.

18. The method of claim 16, wherein the exogenous RNA segment comprises an antisense RNA.

19. The method of claim 16, wherein the exogenous RNA segment comprises a structural RNA.

20. The method of claim 16, wherein the exogenous RNA segment comprises a regulatory RNA.

21. The method of claim 16, wherein the exogenous RNA segment comprises a RNA having catalytic properties.

22. The method of claim 16, wherein the cis-acting viral replication element is derived from tobacco mosaic virus.

23. The method of claim 16, wherein the host plant cell is a dicotyledonous plant cell.

24. A capped RNA molecule capable of infecting a host plant cell, said capped RNA molecule having a sequence of one to three intervening bases located between the cap and the 5' terminus of the viral sequence, said capped RNA molecule comprising:
   (a) the entire genome of a single component (+) strand RNA virus, said (+) strand RNA virus chosen from the group consisting of Carlavirus, Closteroviridae, Luteoviridae, Potexvirus, Potyviridae, Tombusviridae, Tymovirus and Tobamovirus, and
   (b) an exogenous RNA segment, capable of expressing its function in a host plant cell, said exogenous RNA segment inserted into said genome of the (+) strand RNA virus under the control of a subgenomic promoter.

25. A method of modifying a host plant cell phenotypically, said method comprises introducing to the cell a capped RNA molecule capable of infecting a host plant cell, said capped RNA molecule having a sequence of one to three intervening bases located between the cap and the 5' terminus of the viral sequence, said capped RNA molecule comprising:
   (a) the entire genome of a single component (+) strand RNA virus, said (+) strand RiA virus chosen from the group consisting of Carlavirus, Closteroviridae, Luteoviridae, Potexvirus, Potyviridae, Tombusviridae, Tymovirus and Tobamovirus; and
   (b) an exogenous RNA segment, capable of expressing its function in a host plant cell, said exogenous RNA segment inserted into said genome of the (+) strand RNA virus under the control of a subgenomic promoter;
   whereby the exogenous RNA segment confers a detectable trait in the host plant cell, thereby modifying said host plant cell.

26. A DNA transcription vector comprising DNA having one strand complementary to a capped RNA molecule capable of infecting a host plant cell, said capped RNA molecule having a sequence of one to three intervening bases located between the cap and the 5' terninus of the viral sequence, said capped RNA molecule comprising:
   (a) the entire genome of a single component (+) strand RNA virus, said (+) strand RNA virus chosen from the group consisting of Carlavirus, Closteroviridae, Luteoviridac, Potexvirus, Potyviridae, Tombusviridae, Tymovirus and Tobamovirus, and
   (b) an exogenous RNA segment, capable of expressing its function in a host plant cell, said exogenous RNA segment inserted into said genome of the (+) strand RNA virus under the control of a subgenomic promoter.

* * * * *

SEQUENCE LISTING

<160> NUMBER OF SEQ ID NOS: 27

<210> SEQ ID NO 1
<211> LENGTH: 11
<212> TYPE: DNA
<213> ORGANISM: Tobacco mosaic virus

<400> SEQUENCE: 1
tatagtattt t                                                          11

<210> SEQ ID NO 2
<211> LENGTH: 12
<212> TYPE: DNA
<213> ORGANISM: Tobacco mosaic virus

<400> SEQUENCE: 2
tataggtatt tt                                                         12

<210> SEQ ID NO 3
<211> LENGTH: 13
<212> TYPE: DNA
<213> ORGANISM: Tobacco mosaic virus

<400> SEQUENCE: 3
tatagggtat ttt                                                        13

-continued

```
<210> SEQ ID NO 4
<211> LENGTH: 13
<212> TYPE: DNA
<213> ORGANISM: Tobacco mosaic virus

<400> SEQUENCE: 4
tatagggtat ttt                                                              13

<210> SEQ ID NO 5
<211> LENGTH: 13
<212> TYPE: DNA
<213> ORGANISM: Tobacco mosaic virus
<220> FEATURE:
<221> NAME/KEY: misc_feature
<222> LOCATION: (1)...(13)
<223> OTHER INFORMATION: N= A, T, C or G

<400> SEQUENCE: 5
tatagngtat ttt                                                              13

<210> SEQ ID NO 6
<211> LENGTH: 13
<212> TYPE: DNA
<213> ORGANISM: Tobacco mosaic virus
<220> FEATURE:
<221> NAME/KEY: misc_feature
<222> LOCATION: (1)...(13)
<223> OTHER INFORMATION: N= A, T, C or G

<400> SEQUENCE: 6
tatagnntat ttt                                                              13

<210> SEQ ID NO 7
<211> LENGTH: 14
<212> TYPE: DNA
<213> ORGANISM: Tobacco mosaic virus
<220> FEATURE:
<221> NAME/KEY: misc_feature
<222> LOCATION: (1)...(14)
<223> OTHER INFORMATION: N= A, T, C or G

<400> SEQUENCE: 7
tatagnngta tttt                                                             14

<210> SEQ ID NO 8
<211> LENGTH: 14
<212> TYPE: DNA
<213> ORGANISM: Tobacco mosaic virus
<220> FEATURE:
<221> NAME/KEY: misc_feature
<222> LOCATION: (1)...(14)
<223> OTHER INFORMATION: N= A, T, C or G

<400> SEQUENCE: 8
tatagnnnta tttt                                                             14

<210> SEQ ID NO 9
<211> LENGTH: 13
<212> TYPE: DNA
<213> ORGANISM: Tobacco mosaic virus
<220> FEATURE:
<221> NAME/KEY: misc_feature
<222> LOCATION: (1)...(13)
<223> OTHER INFORMATION: N= A, T, C or G

<400> SEQUENCE: 9
tataggngta ttt                                                              13
```

<210> SEQ ID NO 10
<211> LENGTH: 17
<212> TYPE: DNA
<213> ORGANISM: Tobacco mosaic virus
<220> FEATURE:
<221> NAME/KEY: misc_feature
<222> LOCATION: (1)...(17)
<223> OTHER INFORMATION: N= A, T, C or G

<400> SEQUENCE: 10
tatagtngtn gtatttt                                              17

<210> SEQ ID NO 11
<211> LENGTH: 14
<212> TYPE: DNA
<213> ORGANISM: Tobacco mosaic virus
<220> FEATURE:
<221> NAME/KEY: misc_feature
<222> LOCATION: (1)...(14)
<223> OTHER INFORMATION: N= A, T, C or G

<400> SEQUENCE: 11
tatagtngta tttt                                                 14

<210> SEQ ID NO 12
<211> LENGTH: 14
<212> TYPE: DNA
<213> ORGANISM: Tobacco mosaic virus
<220> FEATURE:
<221> NAME/KEY: misc_feature
<222> LOCATION: (1)...(14)
<223> OTHER INFORMATION: N= A, T, C or G

<400> SEQUENCE: 12
tatagtcgta tttt                                                 14

<210> SEQ ID NO 13
<211> LENGTH: 17
<212> TYPE: DNA
<213> ORGANISM: Tobacco mosaic virus
<220> FEATURE:
<221> NAME/KEY: misc_feature
<222> LOCATION: (1)...(17)
<223> OTHER INFORMATION: N= A, T, C or G

<400> SEQUENCE: 13
tatagtngtn gtatttt                                              17

<210> SEQ ID NO 14
<211> LENGTH: 23
<212> TYPE: DNA
<213> ORGANISM: Tobacco mosaic virus
<220> FEATURE:
<221> NAME/KEY: misc_feature
<222> LOCATION: (1)...(23)
<223> OTHER INFORMATION: N= A, T, C or G

<400> SEQUENCE: 14
tatagtngtn gtngtngtat ttt                                       23

<210> SEQ ID NO 15
<211> LENGTH: 17
<212> TYPE: DNA
<213> ORGANISM: Tobacco mosaic virus

<400> SEQUENCE: 15

-continued

```
tatagtattt gtatttt                                              17

<210> SEQ ID NO 16
<211> LENGTH: 45
<212> TYPE: DNA
<213> ORGANISM: Tobacco mosaic virus
<220> FEATURE:
<221> NAME/KEY: misc_feature
<222> LOCATION: (1)...(45)
<223> OTHER INFORMATION: N= A, T, C OR G

<400> SEQUENCE: 16
ggcgatatct aatacgacta tagtngtatt tttacaacaa ttacc               45

<210> SEQ ID NO 17
<211> LENGTH: 48
<212> TYPE: DNA
<213> ORGANISM: Tobacco mosaic virus
<220> FEATURE:
<221> NAME/KEY: misc_feature
<222> LOCATION: (1)...(48)
<223> OTHER INFORMATION: N= A, T, C OR G

<400> SEQUENCE: 17
ggcgatatct aatacgactc actatagngt atttttacaa caattacc            48

<210> SEQ ID NO 18
<211> LENGTH: 50
<212> TYPE: DNA
<213> ORGANISM: Tobacco mosaic virus
<220> FEATURE:
<221> NAME/KEY: misc_feature
<222> LOCATION: (1)...(50)
<223> OTHER INFORMATION: N= A, T, C OR G

<400> SEQUENCE: 18
ggcgatatct aatacgactc actatagnng tatttttaca acaatttacc          50

<210> SEQ ID NO 19
<211> LENGTH: 50
<212> TYPE: DNA
<213> ORGANISM: Tobacco mosaic virus
<220> FEATURE:
<221> NAME/KEY: misc_feature
<222> LOCATION: (1)...(50)
<223> OTHER INFORMATION: N= A, T, C OR G

<400> SEQUENCE: 19
ggcgatatct aatacgactc actatagnnn gtattttac aacaattacc           50

<210> SEQ ID NO 20
<211> LENGTH: 51
<212> TYPE: DNA
<213> ORGANISM: Tobacco mosaic virus
<220> FEATURE:
<221> NAME/KEY: misc_feature
<222> LOCATION: (1)...(51)
<223> OTHER INFORMATION: N= A, T, C OR G

<400> SEQUENCE: 20
ggcgatatct aatacgactc actatagtng tngtattttt acaacaatta c        51

<210> SEQ ID NO 21
<211> LENGTH: 23
<212> TYPE: DNA
<213> ORGANISM: Tobacco mosaic virus

<400> SEQUENCE: 21
```

```
cactatctac acttttatgg gcc                                         23

<210> SEQ ID NO 22
<211> LENGTH: 7685
<212> TYPE: DNA
<213> ORGANISM: Tobacco mosaic virus

<400> SEQUENCE: 22 gtattttac  aacaattacc  aacaacaaca  acaacagac   aacattacaa  ttactattta    60
caattacaat ggcatacaca cagacagcta ccacatcagc tttgctggac actgtccgag      120
gaaacaactc cttggtcaat gatctagcaa agcgtcgtct ttacgacaca gcggttgaag      180
agtttaacgc tcgtgaccgc aggcccaagg tgaacttttc aaaagtaata agcgaggagc      240
agacgcttat tgctacccgg gcgtatccag aattccaaat tacatttat aacacgcaaa       300 atgccgtgca ttcgcttgca ggtggattgc gatctttaga actggaatat ctgatgatgc      360
aaattcccta cggatcattg acttatgaca taggcgggaa ttttgcatcg catctgttca      420
agggacgagc atatgtacac tgctgcatgc ccaacctgga cgttcgagac atcatgcggc      480
acgaaggcca gaaagacagt attgaactat acctttctag gctagagaga ggggggaaaa      540
cagtccccaa cttccaaaag gaagcatttg acagatacgc agaaattcct gaagacgctg      600
tctgtcacaa tactttccag acatgcgaac atcagccgat gcagcaatca ggcagagtgt      660
atgccattgc gctacacagc atatatgaca taccagccga tgagttcggg gcggcactct      720
tgaggaaaaa tgtccatacg tgctatgccg cttttccactt ctccgagaac ctgcttcttg      780
aagattcatg cgtcaatttg gacgaaatca acgcgtgttt ttcgcgcgat ggagacaagt      840 tgacctttttc ttttgcatca gagagtactc ttaattactg tcatagttat tctaatattc      900
ttaagtatgt gtgcaaaact tacttcccgg cctctaatag agaggtttac atgaaggagt      960
ttttagtcac cagagttaat acctggtttt gtaagttttc tagaatagat acttttctttt    1020 tgtacaaagg tgtggcccat aaaagtgtag atagtgagca gttttatact gcaatggaag    1080
acgcatggca ttacaaaaag actcttgcaa tgtgcaacag cgagagaatc ctccttgagg    1140
attcatcatc agtcaattac tggtttccca aaatgaggga tatggtcatc gtaccattat    1200
tcgacatttc tttggagact agtaagagga cgcgcaagga agtcttagtg tccaaggatt    1260
tcgtgtttac agtgcttaac cacattcgaa cataccaggc gaaagctctt acatacgcaa    1320
atgttttgtc cttcgtcgaa tcgattcgat cgagggtaat cattaacggt gtgacagcga    1380
ggtccgaatg ggatgtggac aaatcttttgt tacaatcctt gtccatgacg ttttacctgc    1440
atactaagct tgccgttcta aaggatgact tactgattag caagtttagt ctcggttcga    1500
aaacggtgtg ccagcatgtg tgggatgaga tttcgctggc gtttgggaac gcatttccct    1560
ccgtgaaaga gaggctcttg aacaggaaac ttatcagagt ggcaggcgac gcattagaga    1620
tcagggtgcc tgatctatat gtgaccttcc acgacagatt agtgactgag tacaaggcct    1680
ctgtggacat gcctgcgctt gacattagga gaagatgga gaaacggaa gtgatgtaca     1740 atgcactttc agaattatcg gtgttaaggg agtctgacaa attcgatgtt gatgttttttt    1800 cccagatgtg ccaatctttg gaagttgacc caatgacggc agcgaaggtt atagtcgcgg    1860
tcatgagcaa tgagagcggt ctgactctca catttgaacg acctactgag gcgaatgttg    1920
cgctagcttt acaggatcaa gagaaggctt cagaaggtgc attggtagtt acctcaagag    1980
aagttgaaga accgtccatg aagggttcga tggccagagg agagttacaa ttagctggtc    2040
```

-continued

```
ttgctggaga tcatccggaa tcgtcctatt ctaagaacga ggagatagag tctttagagc    2100
agtttcatat ggcgacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatggggt gttgttgaaa cccacgcgag gaagtatcat gtggcgcttt    2400
tggaatatga tgagcagggt gtggtgacat gcgatgattg gagaagagta gctgttagct    2460
ctgagtctgt tgtttattcc gacatggcga aactcagaac tctgcgcaga ctgcttcgaa    2520
acggagaacc gcatgtcagt agcgcaaagg ttgttcttgt ggacggagtt ccgggctgtg    2580
gaaaaaccaa agaaattctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcgg cggagccgcc gtgatcaatc cgatctcaaa acccttgcat ggcaagatct    3120
tgacttttac ccaatcggat aaagaagctc tgctttcaag agggtattca gatgttcaca    3180
ctgtgcatga agtgcaaggc gagacatact ctgatgtttc actagttagg ttaacccta    3240 caccggtctc catcattgca ggagacagcc cacatgtttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgatatgcag ttttactatg ataagtgtct cccaggcaac agcaccatga    3540
tgaataattt tgatgctgtt accatgaggt tgactgacat tcattgaat gtcaaagatt    3600 gcatattgga tatgtctaag tctgttgctg cgcctaagga tcaaatcaaa ccactaatac    3660
ctatggtacg aacggcggca gaaatgccac gccagactgg actattgaa atttagtgg    3720 cgatgattaa agaaacttt aacgcacccg agttgtctgg catcattgat attgaaaata    3780
ctgcatcttt ggttgtagat aagttttttg atagttattt gcttaaagaa aaagaaaac    3840 caaataaaaa tgtttctttg ttcagtagag agtctctcaa tagatggtta gaaaagcagg    3900
aacaggtaac aataggccag ctcgcagatt ttgattttgt ggatttgcca gcagttgatc    3960
agtacagaca catgattaaa gcacaaccca acaaaagtt ggacacttca atccaaacgg    4020
agtacccggc tttgcagacg attgtgtacc attcaaaaaa gatcaatgca atattcggcc    4080
cgttgtttag tgagcttact aggcaattac tggacagtgt tgattcgagc agatttttgt    4140
ttttcacaag aaagacacca gcgcagattg aggatttctt cggagatctc gacagtcatg    4200
tgccgatgga tgtcttggag ctggatatat caaaatacga caaatctcag aatgaattcc    4260
actgtgcagt agaatacgag atctggcgaa gattgggttt cgaagacttc ttgggagaag    4320
tttgaaaaca agggcataga aagaccaccc tcaaggatta taccgcaggt ataaaaactt    4380
gcatctggta tcaaagaaag agcggggacg tcacgacgtt cattggaaac actgtgatca    4440
```

```
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga tacttttgcg    4620
gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt ctttttagaa gtttgtttat agatggctct agttgttaaa    4920
ggaaaagtga atatcaatga gtttatcgac ctgacaaaaa tggagaagat cttaccgtcg    4980
atgtttaccc ctgtaaagag tgttatgtgt tccaaagttg ataaataat  ggttcatgag    5040 aatgagtcat tgtcagggt  gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cactctcgga    5220
tcttactaca cagcagctgc aaagaaaaga tttcagttca aggtcgttcc caattatgct    5280
ataaccaccc aggacgcgat gaaaaacgtc tggcaagttt tagttaatat tagaaatgtg    5340
aagatgtcag cgggtttctg tccgcttcct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa aagagtgatg tccgcaaagg gaaaaatagt    5580
agtagtgatc ggtcagtgcc gaacaagaac tatagaaatg ttaaggattt tggaggaatg    5640
agttttaaaa agaataattt aatcgatgat gattcggagg ctactgtcgc cgaatcggat    5700 tcgtttaaa  tagatcttac agtatcacta ctccatctca gttcgtgttc ttgtcattaa    5760
ttaaatggct agcaaaggag aagaactttt cactggagtt gtcccaattc ttgttgaatt    5820
agatggtgat gttaatgggc acaaattttc tgtcagtgga gagggtgaag gtgatgctac    5880
atacggaaag cttacccctta aatttatttg cactactgga aaactacctg ttccatggcc    5940
aacacttgtc actactttct cttatggtgt tcaatgcttt tcccgttatc cggatcatat    6000
gaaacggcat gactttttca agagtgccat gcccgaaggt tatgtacagg aacgcactat    6060
atctttcaaa gatgacggga actacaagac gcgtgctgaa gtcaagtttg aaggtgatac    6120
ccttgttaat cgtatcgagt taaaggtat  tgatttttaaa gaagatggaa acattctcgg    6180
acacaaactc gagtacaact ataactcaca caatgtatac atcacggcag acaaacaaaa    6240
gaatggaatc aaagctaact tcaaaattcg ccacaacatt gaagatggat ccgttcaact    6300
agcagaccat tatcaacaaa atactccaat tggcgatggc cctgtccttt taccagacaa    6360
ccattacctg tcgacacaat ctgccctttc gaaagatccc aacgaaaagc gtgaccacat    6420
gggccttctt gagtttgtaa ctgctgctgg gattacacat ggcatggatg agctctacaa    6480
ataatgacac tcgagtggta gtcaagatgc ataataaata acggattgtg tccgtaatca    6540
cacgtggtgc gtacgataac gcatagtgtt tttccctcca cttaaatcga agggttgtgt    6600
cttggatcgc gcgggtcaaa tgtatatggt tcatatacat ccgcaggcac gtaataaagc    6660
gaggggttcg ggtcgaggtc ggctgtgaaa ctcgaaaagg ttccggaaaa caaaaaagag    6720
agtggtaggt aatagtgtta ataataagaa aataaataat agtggtaagaa aaggtttgaa    6780
```

-continued

```
agttgaggaa attgaggata atgtaagtga tgacgagtct atcgcgtcat cgagtacgtt   6840
ttaatcaata tgccttatac aatcaactct ccgagccaat ttgtttactt aagttccgct   6900
tatgcagatc ctgtgcagct gatcaatctg tgtacaaatg cattgggtaa ccagtttcaa   6960
acgcaacaag ctaggacaac agtccaacag caatttgcgg atgcctggaa acctgtgcct   7020
agtatgacag tgagatttcc tgcatcggat ttctatgtgt atagatataa ttcgacgctt   7080
gatccgttga tcacggcgtt attaaatagc ttcgatacta gaaatagaat aatagaggtt   7140
gataatcaac ccgcaccgaa tactactgaa atcgttaacg cgactcagag ggtagacgat   7200
gcgactgtag ctataagggc ttcaatcaat aatttggcta atgaactggt tcgtggaact   7260
ggcatgttca atcaagcaag ctttgagact gctagtggac ttgtctggac cacaactccg   7320
gctacttagc tattgttgtg agatttccta aaataaagtc actgaagact taaaattcag   7380
ggtggctgat accaaaatca gcagtggttg ttcgtccact taaatataac gattgtcata   7440
tctggatcca acagttaaac catgtgatgg tgtatactgt ggtatggcgt aaaacaacgg   7500
aaaagtcgct gaagacttaa aattcagggt ggctgatacc aaaatcagca gtggttgttc   7560
gtccacttaa aaataacgat tgtcatatct ggatccaaca gttaaaccat gtgatggtgt   7620
atactgtggt atggcgtaaa caacggagag gttcgaatcc tcccctaacc gcgggtagcg   7680
gccca                                                                7685
```

<210> SEQ ID NO 23
<211> LENGTH: 7686
<212> TYPE: DNA
<213> ORGANISM: Tobacco mosaic virus

<400> SEQUENCE: 23

```
gtatttttac aacaattacc aacaacaaca aacaacagac aacattacaa ttactattta     60
caattacaat ggcatacaca cagacagcta ccacatcagc tttgctggac actgtccgag    120
gaaacaactc cttggtcaat gatctagcaa agcgtcgtct ttacgacaca gcggttgaag    180
agtttaacgc tcgtgaccgc aggcccaagg tgaacttttc aaaagtaata agcgaggagc    240
agacgcttat tgctacccgg gcgtatccag aattccaaat tacattttat aacacgcaaa    300
atgccgtgca ttcgcttgca ggtggattgc gatctttaga actggaatat ctgatgatgc    360
aaattcccta cggatcattg acttatgaca taggcgggaa ttttgcatcg catctgttca    420
agggacgagc atatgtacac tgctgcatgc ccaacctgga cgttcgagac atcatgcggc    480
acgaaggcca gaaagacagt attgaactat accttttctag gctagagaga ggggggaaaa    540
cagtccccaa cttccaaaag gaagcatttg acagatacgc agaaattcct gaagacgctg    600
tctgtcacaa tacttttccag acatgcgaac atcagccgat gcagcaatca ggcagagtgt    660
atgccattgc gctacacagc atatatgaca taccagccga tgagttcggg gcggcactct    720
tgaggaaaaa tgtccatacg tgctatgccg cttttccactt ctccgagaac ctgcttcttg    780
aagattcatg cgtcaatttg gacgaaatca acgcgtgttt ttcgcgcgat ggagacaagt    840
tgaccttttc ttttgcatca gagagtactc ttaattactg tcatagttat tctaatattc    900
ttaagtatgt gtgcaaaact tacttcccgg cctctaatag agagggtttac atgaaggagt    960 ttttagtcac cagagttaat acctggttttt gtaagttttc tagaatagat acttttctttt   1020 tgtacaaagg tgtggcccat aaaagtgtag atagtgagca gttttatact gcaatggaag   1080
acgcatggca ttacaaaaag actcttgcaa tgtgcaacag cgagagaatc ctccttgagg   1140
attcatcatc agtcaattac tggtttccca aaatgaggga tatggtcatc gtaccattat   1200
```

```
tcgacatttc tttggagact agtaagagga cgcgcaagga agtcttagtg tccaaggatt    1260
tcgtgttcac agtgcttaac cacattcgaa cataccaggc gaaagctctt acatacgcaa    1320
atgttttgtc cttcgtcgaa tcgattcgat cgagggtaat cattaacggt gtgacagcga    1380
ggtccgaatg ggatgtggac aaatctttgt tacaatcctt gtccatgacg ttttacctgc    1440
atactaagct tgccgttcta aaggatgact tactgattag caagtttagt ctcggttcga    1500
aaacggtgtg ccagcatgtg tgggatgaga tttcgctggc gtttgggaac gcatttccct    1560
ccgtgaaaga gaggctcttg aacaggaaac ttatcagagt ggcaggcgac gcattagaga    1620
tcagggtgcc tgatctatat gtgaccttcc acgacagatt agtgactgag tacaaggcct    1680
ctgtggacat gcctgcgctt gacattagga agaagatgga agaaacggaa gtgatgtaca    1740
atgcactttc agaattatcg gtgttaaggg agtctgacaa attcgatgtt gatgtttttt    1800
cccagatgtg ccaatctttg gaagttgacc caatgacggc agcgaaggtt atagtcgcgg    1860
tcatgagcaa tgagagcggt ctgactctca catttgaacg acctactgag gcgaatgttg    1920
cgctagcttt acaggatcaa gagaaggctt cagaaggtgc attggtagtt acctcaagag    1980
aagttgaaga accgtccatg aagggttcga tggccagagg agagttacaa ttagctggtc    2040
ttgctggaga tcatccggaa tcgtcctatt ctaagaacga ggagatagag tctttagagc    2100
agtttcatat ggcgacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatggggt gttgttgaaa cccacgcgag gaagtatcat gtggcgcttt    2400
tggaatatga tgagcagggt gtggtgacat gcgatgattg gagaagagta gctgttagct    2460
ctgagtctgt tgtttattcc gacatggcga aactcagaac tctgcgcaga ctgcttcgaa    2520
acggagaacc gcatgtcagt agcgcaaagg ttgttcttgt ggacggagtt ccgggctgtg    2580
gaaaaaccaa agaaattctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcgc cggagccgcc gtgatcaatc cgatctcaaa acccttgcat ggcaagatcc    3120
tgacttttac ccaatcggat aaagaagctc tgctttcaag agggtattca gatgttcaca    3180
ctgtgcatga agtgcaaggc gagacatact ctgatgtttc actagttagg ttaaccccta    3240
caccggtctc catcattgca ggagacagcc cacatgtttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt gttgcagcg ccaaagactg    3480
gtgatatttc tgatatgcag ttttactatg ataagtgtct cccaggcaac agcaccatga    3540
```

```
tgaataattt tgatgctgtt accatgaggt tgactgacat ttcattgaat gtcaaagatt      3600
gcatattgga tatgtctaag tctgttgctg cgcctaagga tcaaatcaaa ccactaatac      3660
ctatggtacg aacggcggca gaaatgccac gccagactgg actattggaa atttagtgg       3720 cgatgattaa aagaaacttt aacgcacccg agttgtctgg catcattgat attgaaaata      3780
ctgcatcttt ggttgtagat aagttttttg atagttattt gcttaaagaa aaagaaaaac      3840
caaataaaaa tgtttctttg ttcagtagag agtctctcaa tagatggtta gaaaagcagg      3900
aacaggtaac aataggccag ctcgcagatt ttgattttgt ggatttgcca gcagttgatc      3960
agtacagaca catgattaaa gcacaaccca acaaaagtt ggacacttca atccaaacgg       4020
agtacccggc tttgcagacg attgtgtacc attcaaaaaa gatcaatgca atattcggcc      4080
cgttgtttag tgagcttacc aggcaattac tggacagtgt tgattcgagc agattttgt       4140 ttttcacaag aaagacacca gcgcagattg aggatttctt cggagatctc gacagtcatg      4200
tgccgatgga tgtcttggag ctggatatat caaaatacga caaatctcag aatgaattcc      4260
actgtgcagt agaatacgag atctggcgaa gattgggttt cgaagacttc ttgggagaag      4320
tttgaaaaca agggcataga aagaccaccc tcaaggatta taccgcaggt ataaaaactt      4380
gcatctggta tcaaagaaag agcggggacg tcacgacgtt cattggaaac actgtgatca      4440
ttgctgcatg tttggcctcg atgcttccga tggagaaaat aatcaaagga gccttttgcg      4500
gtgacgatag tctgctgtac tttccaaagg gttgtgagtt tccggatgtg caacactccg      4560
cgaatcttat gtggaatttt gaagcaaaac tgtttaaaaa acagtatgga tacttttgcg      4620
gaagatatgt aatacatcac gacagaggat gcattgtgta ttacgatccc ctaaagttga      4680
tctcgaaact tggtgctaaa cacatcaagg attgggaaca cttggaggag ttcagaaggt      4740
ctctttgtga tgttgctgtt tcgttgaaca attgtgcgta ttacacacag ttggacgacg      4800
ctgtatggga ggttcataag accgcccctc caggttcgtt tgtttataaa agtctggtga      4860
agtatttgtc tgataaagtt cttttttagaa gtttgtttat agatggctct agttgttaaa      4920
ggaaaagtga atatcaatga gtttatcgac ctgacaaaaa tggagaagat cttaccgtcg      4980
atgtttaccc ctgtaaagag tgttatgtgt tccaaagttg ataaaataat ggttcatgag      5040
aatgagtcat tgtcagggg gaaccttctt aaaggagtta agcttattga tagtggatac       5100
gtctgtttag ccggtttggt cgtcacgggc gagtggaact tgcctgacaa ttgcagagga      5160
ggtgtgagcg tgtgtctggt ggacaaaagg atggaaagag ccgacgaggc cattctcgga      5220
tcttactaca cagcagctgc aaagaaaaga tttcagttca aggtcgttcc caattatgct      5280
ataaccaccc aggacgcgat gaaaaacgtc tggcaagttt tagttaatat tagaaatgtg      5340
aagatgtcag cgggtttctg tccgcttct ctggagtttg tgtcggtgtg tattgtttat        5400
agaaataata taaattagg tttgagagag aagattacaa acgtgagaga cggagggccc        5460
atggaactta cagaagaagt cgttgatgag ttcatggaag atgtccctat gtcgatcagg      5520
cttgcaaagt ttcgatctcg aaccggaaaa aagagtgatg tccgcaaagg gaaaaatagt      5580
agtagtgatc ggtcagtgcc gaacaagaac tatagaaatg ttaaggattt tgggggaatg     5640
agttttaaaa agaataattt aatcgatgat gattcggagg ctactgtcgc cgaatcggat     5700
tcgttttaaa tagatcttac agtatcacta ctccatctca gttcgtgttc ttgtcattaa      5760
ttaaatggct agcaaggag aagaacttt cactggagtt gtcccaattc ttgttgaatt        5820
agatggtgat gttaatgggc acaaatttc tgtcagtgga gagggtgaag gtgatgctac       5880
atacggaaag cttacactta aatttatttg cactactgga aaactacctg ttccatggcc     5940
```

-continued

```
aacacttgtc actactttct cttatggtgt tcaatgctttt tcccgttatc cggatcatat      6000
gaaacggcat gacttttttca agagtgccat gcccgaaggt tatgtacagg aacgcactat     6060
atctttcaaa gatgacggga actacaagac gcgtgctgaa gtcaagtttg aaggtgatac      6120
ccttgttaat cgtatcgagt taaaaggtat tgattttaaa gaagatggaa acattctcgg      6180
acacaaactc gagtacaact ataactcaca caatgtatac atcacggcag acaaacaaaa     6240
gaatggaatc aaagctaact tcaaaattcg ccacaacatt gaagatggat ccgttcaact     6300
agcagaccat tatcaacaaa atactccaat tggcgatggc cctgtccttt taccagacaa     6360
ccattacctg tcgacacaat ctgccctttc gaaagatccc aacgaaaagc gtgaccacat     6420
ggtccttctt gagtttgtaa ctgctgctgg gattacacat ggcatggatg agctctacaa    6480
ataatgacac tcgagggta gtcaagatgc ataataaata acggattgtg tccgtaatca     6540
cacgtggtgc gtacgataac gcatagtgtt tttccctcca cttaaatcga agggttgtgt    6600
cttggatcgc gcgggtcaaa tgtatatggt tcatatacat ccgcaggcac gtaataaagc    6660
gaggggttcg ggtcgaggtc ggctgtgaaa ctcgaaaagg ttccggaaaa caaaaaagag    6720
agtggtaggt aatagtgtta ataataagaa aataaataat agtggtaaga aaggtttgaa    6780
agttgaggaa attgaggata atgtaagtga tgacgagtct atcgcgtcat cgagtacgtt    6840
ttaatcaata tgccttatac aatcaactct ccgagccaat ttgtttactt aagttccgct    6900
tatgcagatc ctgtgcagct gatcaatctg tgtacaaatg cattgggtaa ccagtttcaa    6960
acgcaacaag ctaggacaac agtccaacag caatttgcgg atgcctggaa acctgtgcct    7020
agtatgacag tgagatttcc tgcatcggat ttctatgtgt atagatataa ttcgacgctt    7080
gatccgttga tcacggcgtt attaaatagc ttcgatacta gaaatagaat aatagaggtt    7140
gataatcaac ccgcaccgaa tactactgaa atcgttaacg cgactcagag ggtagacgat    7200
gcgactgtag ctataagggc ttcaatcaat aatttggcta atgaactggt tcgtggaact    7260
ggcatgttca atcaagcaag ctttgagact gctagtggac ttgtctggac cacaactccg    7320
gctacttagc tattgttgtg agatttccta aaataaagtc actgaagact taaaattcag    7380
ggtggctgat accaaaatca gcagtggttg ttcgtccact taaatataac gattgtcata    7440
tctggatcca acagttaaac catgtgatgg tgtatactgt ggtatggcgt aaaacaacgg    7500
aaaagtcgct gaagacttaa aattcagggt ggctgatacc aaaatcagca gtggttgttc    7560
gtccacttaa aaataacgat tgtcatatct ggatccaaca gttaaaccat gtgatggtgt    7620
atactgtggt atggcgtaaa acaacggaga ggttcgaatc ctcccctaac cgcgggtagc    7680
ggccca                                                                7686
```

<210> SEQ ID NO 24
<211> LENGTH: 7687
<212> TYPE: DNA
<213> ORGANISM: Tobacco mosaic virus

<400> SEQUENCE: 24

```
ggtatttta caacaattac caacaacaac aaacaacaga caacattaca attactattt        60
acaattacaa tggcatacac acagacagct accacatcag ctttgctgga cactgtccga      120
ggaaacaact ccttggtcaa tgatctagca aagcgtcgtc tttacgacac agcggttgaa      180
gagtttaacg ctcgtgaccg caggcccaag gtgaactttt caaaagtaat aagcgaggag      240
cagacgctta ttgctacccg ggcgtatcca gaattccaaa ttacatttta taacacgcaa       300
```

-continued

| | |
|---|---|
| aatgccgtgc attcgcttgc aggtggattg cgatctttag aactggaata tctgatgatg | 360 |
| caaattccct acggatcatt gacttatgac ataggcggga attttgcatc gcatctgttc | 420 |
| aagggacgag catatgtaca ctgctgcatg cccaacctgg acgttcgaga catcatgcgg | 480 |
| cacgaaggcc agaaagacag tattgaacta tacctttcta ggctagagag agggggaaa | 540 |
| acagtcccca acttccaaaa ggaagcattt gacagatacg cagaaattcc tgaagacgct | 600 |
| gtctgtcaca atactttcca gacatgcgaa catcagccga tgcagcaatc aggcagagtg | 660 |
| tatgccattg cgctacacag catatatgac ataccagccg atgagttcgg ggcggcactc | 720 |
| ttgaggaaaa atgtccatac gtgctatgcc gctttccact tctccgagaa cctgcttctt | 780 |
| gaagattcat gcgtcaattt ggacgaaatc aacgcgtgtt tttcgcgcga tggagacaag | 840 |
| ttgaccttt cttttgcatc agagagtact cttaattact gtcatagtta ttctaatatt | 900 |
| cttaagtatg tgtgcaaaac ttacttcccg gcctctaata gagaggttta catgaaggag | 960 |
| tttttagtca ccagagttaa tacctggttt tgtaagtttt ctagaataga tacttttctt | 1020 |
| ttgtacaaag gtgtggccca taaagtgta gatagtgagc agttttatac tgcaatggaa | 1080 |
| gacgcatggc attacaaaaa gactcttgca atgtgcaaca gcgagagaat cctccttgag | 1140 |
| gattcatcat cagtcaatta ctggtttccc aaaatgaggg atatggtcat cgtaccatta | 1200 |
| ttcgacattt cttggagac tagtaagagg acgcgcaagg aagtcttagt gtccaaggat | 1260 |
| ttcgtgttca cagtgcttaa ccacattcga acataccagg cgaaagctct tacatacgca | 1320 |
| aatgttttgt ccttcgtcga atcgattcga tcgagggtaa tcattaacgg tgtgacagcg | 1380 |
| aggtccgaat gggatgtgga caaatctttg ttacaatcct tgtccatgac gttttacctg | 1440 |
| catactaagc ttgccgttct aaaggatgac ttactgatta gcaagtttag tctcggttcg | 1500 |
| aaaacggtgt gccagcatgt gtgggatgag atttcgctgg cgtttgggaa cgcatttccc | 1560 |
| tccgtgaaag agaggctctt gaacaggaaa cttatcagag tggcaggcga cgcattagag | 1620 |
| atcagggtgc ctgatctata tgtgaccttc cacgacagat tagtgactga gtacaaggcc | 1680 |
| tctgtggaca tgcctgcgct tgacattagg aagaagatga agaaacgga agtgatgtac | 1740 |
| aatgcacttt cagaattatc ggtgttaagg gagtctgaca aattcgatgt tgatgttttt | 1800 |
| tcccagatgt gccaatcttt ggaagttgac ccaatgacgg cagcgaaggt tatagtcgcg | 1860 |
| gtcatgagca atgagagcgg tctgactctc acatttgaac gacctactga ggcgaatgtt | 1920 |
| gcgctagctt tacaggatca agagaaggct tcagaaggtg cattggtagt tacctcaaga | 1980 |
| gaagttgaag aaccgtccat gaagggttcg atggccagag gagagttaca attagctggt | 2040 |
| cttgctggag atcatccgga atcgtcctat tctaagaacg aggagataga gtctttagag | 2100 |
| cagtttcata tggcgacggc agattcgtta attcgtaagc agatgagctc gattgtgtac | 2160 |
| acgggtccga ttaaagttca gcaaatgaaa aactttatcg atagcctggt agcatcacta | 2220 |
| tctgctgcgg tgtcgaatct cgtcaagatc ctcaaagata cagctgctat tgaccttgaa | 2280 |
| acccgtcaaa agtttggagt cttggatgtt gcatctagga agtggttaat caaaccaacg | 2340 |
| gccaagagtc atgcatgggg tgttgttgaa acccacgcga ggaagtatca tgtggcgctt | 2400 |
| ttggaatatg atgagcaggg tgtggtgaca tgcgatgatt ggagaagagt agctgttagc | 2460 |
| tctgagtctg ttgtttattc cgacatggcg aaactcagaa ctctgcgcag actgcttcga | 2520 |
| aacggagaac cgcatgtcag tagcgcaaag gttgttcttg tggacggagt tccgggctgt | 2580 |
| ggaaaaacca agaaattct ttccagggtt aatttttgatg aagatctaat tttagtacct | 2640 |
| gggaagcaag ccgcggaaat gatcagaaga cgtgcgaatt cctcagggat tattgtggcc | 2700 |

-continued

```
acgaaggaca acgttaaaac cgttgattct tcatgatga attttgggaa aagcacacgc   2760
tgtcagttca agaggttatt cattgatgaa gggttgatgt tgcatactgg ttgtgttaat   2820
tttcttgtgg cgatgtcatt gtgcgaaatt gcatatgttt acggagacac acagcagatt   2880
ccatacatca atagagtttc aggattcccg taccccgccc attttgccaa attggaagtt   2940
gacgaggtgg agacacgcag aactactctc cgttgtccag ccgatgtcac acattatctg   3000
aacaggagat atgagggctt tgtcatgagc acttcttcgg ttaaaaagtc tgtttcgcag   3060
gagatggtcg gcggagccgc cgtgatcaat ccgatctcaa aacccttgca tggcaagatc   3120
ctgactttta cccaatcgga taaagaagct ctgctttcaa gagggtattc agatgttcac   3180
actgtgcatg aagtgcaagg cgagacatac tctgatgttt cactagttag gttaacccct   3240
acaccggtct ccatcattgc aggagacagc ccacatgttt tggtcgcatt gtcaaggcac   3300
acctgttcgc tcaagtacta cactgttgtt atggatcctt tagttagtat cattagagat   3360
ctagagaaac ttagctcgta cttgttagat atgtataagg tcgatgcagg aacacaatag   3420
caattacaga ttgactcggt gttcaaaggt tccaatcttt tgttgcagc gccaaagact   3480 ggtgatattt ctgatatgca gttttactat gataagtgtc tcccaggcaa cagcaccatg   3540
atgaataatt tgatgctgt taccatgagg ttgactgaca tttcattgaa tgtcaaagat   3600
tgcatattgg atatgtctaa gtctgttgct gcgcctaagg atcaaatcaa accactaata   3660
cctatggtac gaacggcggc agaaatgcca cgccagactg gactattgga aaatttagtg   3720
gcgatgatta aaagaaactt taacgcaccc gagttgtctg gcatcattga tattgaaaat   3780
actgcatctt tggttgtaga taagtttttt gatagttatt tgcttaaaga aaaagaaaa    3840 ccaaataaaa atgtttcttt gttcagtaga gagtctctca atagatggtt agaaaagcag   3900
gaacaggtaa caataggcca gctcgcagat tttgattttg tggatttgcc agcagttgat   3960
cagtacagac acatgattaa agcacaaccc aaacaaaagt tggacacttc aatccaaacg   4020
gagtacccgg ctttgcagac gattgtgtac cattcaaaaa agatcaatgc aatattcggc   4080
ccgttgttta gtgagcttac caggcaatta ctggacagtg ttgattcgag cagatttttg   4140
tttttcacaa gaaagacacc agcgcagatt gaggatttct tcggagatct cgacagtcat   4200
gtgccgatgg atgtcttgga gctggatata tcaaaatacg acaaatctca gaatgaattc   4260
cactgtgcag tagaatacga gatctggcga agattgggtt tcgaagactt cttgggagaa   4320
gtttggaaac aagggcatag aaagaccacc ctcaaggatt ataccgcagg tataaaaact   4380
tgcatctggt atcaaagaaa gagcggggac gtcacgacgt tcattggaaa cactgtgatc   4440
attgctgcat gtttggcctc gatgcttccg atggagaaaa taatcaaagg agccttttgc   4500
ggtgacgata gtctgctgta ctttccaaag ggttgtgagt ttccggatgt gcaacactcc   4560
gcgaatctta tgtggaattt tgaagcaaaa ctgtttaaaa acagtatgg atacttttgc   4620 ggaagatatg taatacatca cgacagagga tgcattgtgt attacgatcc cctaaagttg   4680
atctcgaaac ttggtgctaa acacatcaag gattgggaac acttggagga gttcagaagg   4740
tctctttgtg atgttgctgt ttcgttgaac aattgtgcgt attacacaca gttggacgac   4800
gctgtatggg aggttcataa gaccgcccct ccaggttcgt tgtttataa aagtctggtg     4860 aagtatttgt ctgataaagt tctttttaga gtttgttta tagatggctc tagttgttaa     4920
aggaaaagtg aatatcaatg agtttatcga cctgacaaaa atggagaaga tcttaccgtc     4980
gatgtttacc cctgtaaaga gtgttatgtg ttccaaagtt gataaaataa tggttcatga     5040
```

-continued

```
gaatgagtca ttgtcagggg tgaaccttct taaaggagtt aagcttattg atagtggata      5100
cgtctgttta gccggtttgg tcgtcacggg cgagtggaac ttgcctgaca attgcagagg      5160
aggtgtgagc gtgtgtctgg tggacaaaag gatggaaaga gccgacgagg ccattctcgg      5220
atcttactac acagcagctg caaagaaaag atttcagttc aaggtcgttc ccaattatgc      5280
tataaccacc caggacgcga tgaaaaacgt ctggcaagtt ttagttaata ttagaaatgt      5340
gaagatgtca gcgggtttct gtccgctttc tctggagttt gtgtcggtgt gtattgttta      5400
tagaaataat ataaaattag gtttgagaga gaagattaca aacgtgagag acggagggcc      5460
catggaactt acagaagaag tcgttgatga gttcatggaa gatgtcccta tgtcgatcag      5520
gcttgcaaag tttcgatctc gaaccggaaa aagagtgat gtccgcaaag ggaaaaatag       5580
tagtagtgat cggtcagtgc cgaacaagaa ctatagaaat gttaaggatt ttgggggaat      5640
gagttttaaa aagaataatt taatcgatga tgattcggag gctactgtcg ccgaatcgga      5700
ttcgttttaa atagatctta cagtatcact actccatctc agttcgtgtt cttgtcatta      5760
attaaatggc tagcaaagga gaagaacttt tcactggagt tgtcccaatt cttgttgaat      5820
tagatggtga tgttaatggg cacaaatttt ctgtcagtgg agagggtgaa ggtgatgcta      5880
catacggaaa gcttcacttt aaatttattt gcactactgg aaaactacct gttccatggc      5940
caacacttgt cactactttc tcttatggtg ttcaatgctt ttcccgttat ccggatcata      6000
tgaaacggca tgacttttc aagagtgcca tgcccgaagg ttatgtacag gaacgcacta      6060
tatctttcaa agatgacggg aactacaaga cgcgtgctga agtcaagttt gaaggtgata      6120
cccttgttaa tcgtatcgag ttaaaaggta ttgattttaa agaagatgga acattctcg       6180 gacacaaact cgagtacaac tataactcac acaatgtata catcacggca gacaaacaaa      6240
agaatggaat caaagctaac ttcaaaattc gccacaacat tgaagatgga tccgttcaac      6300
tagcagacca ttatcaacaa atactccaa ttggcgatgg ccctgtcctt ttaccagaca       6360
accattacct gtcgacacaa tctgcccttt cgaaagatcc caacgaaaag cgtgaccaca      6420
tggtccttct tgagtttgta actgctgctg ggattacaca tggcatggat gagctctaca      6480
aataatgaca ctcgaggggt agtcaagatg cataataaat aacggattgt gtccgtaatc      6540
acacgtggtg cgtacgataa cgcatagtgt ttttccctcc acttaaatcg aagggttgtg     6600
tcttggatcg cgcgggtcaa atgtatatgg ttcatataca tccgcaggca cgtaataaag     6660
cgaggggttc gggtcgaggt cggctgtgaa actcgaaaag gttccggaaa acaaaaaaga     6720
gagtggtagg taatagtgtt aataataaga aaataaataa tagtggtaag aaaggtttga     6780
aagttgagga aattgaggat aatgtaagtg atgacgagtc tatcgcgtca tcgagtacgt      6840
tttaatcaat atgccttata caatcaactc tccgagccaa tttgtttact taagttccgc      6900
ttatgcagat cctgtgcagc tgatcaatct gtgtacaaat gcattgggta accagtttca      6960
aacgcaacaa gctaggacaa cagtccaaca gcaatttgcg gatgcctgga aacctgtgcc      7020
tagtatgaca gtgagatttc ctgcatcgga tttctatgtg tatagatata attcgacgct      7080
tgatccgttg atcacggcgt tattaaatag cttcgatact agaaatagaa taatagaggt      7140
tgataatcaa cccgcaccga atactactga aatcgttaac gcgactcaga gggtagacga      7200
tgcgactgta gctataaggg cttcaatcaa taatttggct aatgaactgg ttcgtggaac      7260
tggcatgttc aatcaagcaa gctttgagac tgctagtgga cttgtctgga ccacaactcc      7320
ggctacttag ctattgttgt gagatttcct aaaataaagt cactgaagac ttaaaattca      7380
gggtggctga taccaaaatc agcagtggtt gttcgtccac ttaaatataa cgattgtcat      7440
```

```
atctggatcc aacagttaaa ccatgtgatg gtgtatactg tggtatggcg taaaacaacg    7500
gaaaagtcgc tgaagactta aaattcaggg tggctgatac caaaatcagc agtggttgtt    7560
cgtccactta aaaataacga ttgtcatatc tggatccaac agttaaacca tgtgatggtg    7620
tatactgtgg tatggcgtaa acaacggag aggttcgaat cctcccctaa ccgcgggtag    7680
cggccca                                                              7687
```

<210> SEQ ID NO 25
<211> LENGTH: 7685
<212> TYPE: DNA
<213> ORGANISM: Tobacco mosaic virus

<400> SEQUENCE: 25

```
gtattttttac aacaattacc aacaacaaca acaacagac aacattacaa ttactattta    60
caattacaat ggcatacaca cagacagcta ccacatcagc tttgctggac actgtccgag   120
gaaacaactc cttggtcaat gatctagcaa agcgtcgtct ttacgacaca gcggttgaag   180
agtttaacgc tcgtgaccgc aggcccaagg tgaacttttc aaaagtaata agcgaggagc   240
agacgcttat tgctacccgg gcgtatccag aattccaaat tacatttat aacacgcaaa   300 atgccgtgca ttcgcttgca ggtggattgc gatctttaga actggaatat ctgatgatgc   360
aaattcccta cggatcattg acttatgaca taggcgggaa ttttgcatcg catctgttca   420
agggacgagc atatgtacac tgctgcatgc ccaacctgga cgttcgagac atcatgcggc   480
acgaaggcca gaaagacagt attgaactat acctttctag gctagagaga gggggggaaaa   540 cagtccccaa cttccaaaag gaagcatttg acagatacgc agaaattcct gaagacgctg   600
tctgtcacaa tacttttcag acatgcgaac atcagccgat gcagcaatca ggcagagtgt   660
atgccattgc gctacacagc atatatgaca taccagccga tgagttcggg gcggcactct   720
tgaggaaaaa tgtccatacg tgctatgccg cttttcactt ctccgagaac ctgcttcttg   780
aagattcatg cgtcaatttg gacgaaatca acgcgtgttt ttcgcgcgat ggagacaagt   840 tgacctttttc ttttgcatca gagagtactc ttaattactg tcatagttat tctaatattc   900
ttaagtatgt gtgcaaaact tacttcccgg cctctaatag agaggtttac atgaaggagt   960
ttttagtcac cagagttaat acctggtttt gtaagtttttc tagaatagat acttttcttt  1020
tgtacaaagg tgtggcccat aaaagtgtag atagtgagca gttttatact gcaatggaag  1080
acgcatggca ttacaaaaag actcttgcaa tgtgcaacag cgagagaatc ctccttgagg  1140
attcatcatc agtcaattac tggtttccca aaatgaggga tatggtcatc gtaccattat  1200
tcgacatttc tttggagact agtaagagga cgcgcaagga agtcttagtg tccaaggatt  1260
tcgtgtttac agtgcttaac cacattcgaa cataccaggc gaaagctctt acatacgcaa  1320
atgttttgtc cttcgtcgaa tcgattcgat cgagggtaat cattaacggt gtgacagcga  1380
ggtccgaatg ggatgtggac aaatctttgt tacaatcctt gtccatgacg ttttacctgc  1440
atactaagct tgccgttcta aaggatgact tactgattag caagtttagt ctcggttcga  1500
aaacggtgtg ccagcatgtg tgggatgaga tttcgctggc gtttgggaac gcatttccct  1560
ccgtgaaaga gaggctcttg aacaggaaac ttatcagagt ggcaggcgac gcattagaga  1620
tcagggtgcc tgatctatat gtgaccttcc acgacagatt agtgactgag tacaaggcct  1680
ctgtggacat gcctgcgctt gacattagga gaagatggaa agaaacggaa gtgatgtaca  1740
atgcactttc agaattatcg gtgttaaggg agtctgacaa attcgatgtt gatgtttttt  1800
```

-continued

```
cccagatgtg ccaatctttg gaagttgacc caatgacggc agcgaaggtt atagtcgcgg    1860
tcatgagcaa tgagagcggt ctgactctca catttgaacg acctactgag gcgaatgttg    1920
cgctagcttt acaggatcaa gagaaggctt cagaaggtgc attggtagtt acctcaagag    1980
aagttgaaga accgtccatg aagggttcga tggccagagg agagttacaa ttagctggtc    2040
ttgctggaga tcatccggaa tcgtcctatt ctaagaacga ggagatagag tctttagagc    2100
agtttcatat ggcgacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatggggt gttgttgaaa cccacgcgag gaagtatcat gtggcgcttt    2400
tggaatatga tgagcagggt gtggtgacat gcgatgattg gagaagagta gctgttagct    2460
ctgagtctgt tgtttattcc gacatggcga aactcagaac tctgcgcaga ctgcttcgaa    2520
acggagaacc gcatgtcagt agcgcaaagg ttgttcttgt ggacggagtt ccgggctgtg    2580
gaaaaaccaa agaaattctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcgc cggagccgcc gtgatcaatc cgatctcaaa accccttgcat ggcaagatct    3120
tgacttttac ccaatcggat aaagaagctc tgctttcaag agggtattca gatgttcaca    3180
ctgtgcatga agtgcaaggc gagacatact ctgatgtttc actagttagg ttaacccota    3240
caccggtctc catcattgca ggagacagcc cacatgtttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgatatgcag ttttactatg ataagtgtct cccaggcaac agcaccatga    3540
tgaataattt tgatgctgtt accatgaggt tgactgacat tcattgaat gtcaaagatt    3600
gcatattgga tatgtctaag tctgttgctg cgcctaagga tcaaatcaaa ccactaatac    3660
ctatggtacg aacggcggca gaaatgccac gccagactgg actattggaa aattagtgg    3720
cgatgattaa aagaaacttt aacgcacccg agttgtctgg catcattgat attgaaaata    3780
ctgcatcttt ggttgtagat aagttttttg atagttattt gcttaaagaa aaagaaaaac    3840
caaataaaaa tgtttctttg ttcagtagag agtctctcaa tagatggtta gaaaagcagg    3900
aacaggtaac aataggccag ctcgcagatt ttgattttgt ggatttgcca gcagttgatc    3960
agtacagaca catgattaaa gcacaaccca aacaaaagtt ggacacttca atccaaacgg    4020
agtacccggc tttgcagacg attgtgtacc attcaaaaaa gatcaatgca atattcggcc    4080
cgttgtttag tgagcttact aggcaattac tggacagtgt tgattcgagc agatttttgt    4140
ttttcacaag aaagacacca gcgcagattg aggatttctt cggagatctc gacagtcatg    4200
```

-continued

```
tgccgatgga tgtcttggag ctggatatat caaaatacga caaatctcag aatgaattcc    4260
actgtgcagt agaatacgag atctggcgaa gattgggttt cgaagacttc ttgggagaag    4320
tttggaaaca agggcataga aagaccaccc tcaaggatta taccgcaggt ataaaaactt    4380
gcatctggta tcaaagaaag agcggggacg tcacgacgtt cattggaaac actgtgatca    4440
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga tacttttgcg    4620
gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt cttttagaa gtttgtttat agatggctct agttgttaaa    4920 ggaaagtga atatcaatga gtttatcgac ctgacaaaaa tggagaagat cttaccgtcg    4980
atgtttaccc ctgtaaagag tgttatgtgt tccaaagttg ataaaataat ggttcatgag    5040
aatgagtcat tgtcagggt gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cattctcgga    5220
tcttactaca cagcagctgc aaagaaaaga tttcagttca aggtcgttcc caattatgct    5280
ataaccaccc aggacgcgat gaaaaacgtc tggcaagttt tagttaatat tagaaatgtg    5340
aagatgtcag cgggtttctg tccgctttct ctggagtttg tgtcggtgtg tattgtttat    5400
aaaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa aagagtgatg tccgcaaagg gaaaaatagt    5580
agtagtgatc ggtcagtgcc gaacaagaac tatagaaatg ttaaggattt tggaggaatg    5640
agttttaaaa agaataattt aatcgatgat gattcggagg ctactgtcgc cgaatcggat    5700
tcgttttaaa tagatcttac agtatcacta ctccatctca gttcgtgttc ttgtcattaa    5760
ttaaatggct agcaaaggag aagaacttt cactggagtt gtcccaattc ttgttgaatt    5820
agatggtgat gttaatgggc acaaattttc tgtcagtgga gagggtgaag gtgatgctac    5880
atacggaaag cttacccctta aatttatttg cactactgga aaactacctg ttccatggcc    5940
aacacttgtc actactttct cttatggtgt tcaatgcttt cccgttatc cggatcatat    6000 gaaacggcat gactttttca agagtgccat gcccgaaggt tatgtacagg aacgcactat    6060
atctttcaaa gatgacggga actacaagac gcgtgctgaa gtcaagtttg aaggtgatac    6120
ccttgttaat cgtatcgagt taaaaggtat tgattttaaa gaagatggaa acattctcgg    6180
acacaaactc gagtacaact ataactcaca caatgtatac atcacggcag acaaacaaaa    6240
gaatggaatc aaagctaact tcaaaattcg ccacaacatt gaagatggat ccgttcaact    6300
agcagaccat tatcaacaaa atactccaat tggcgatggc cctgtccttt taccagacaa    6360
ccattacctg tcgacacaat ctgccctttc gaaagatccc aacgaaaagc gtgaccacat    6420
gggccttctt gagtttgtaa ctgctgctgg gattacacat ggcatggatg agctctacaa    6480
ataatgacac tcgagggta gtcaagatgc ataataaata acggattgtg tccgtaatca    6540
```

-continued

```
cacgtggtgc gtacgataac gcatagtgtt tttccctcca cttaaatcga agggttgtgt    6600
cttggatcgc gcgggtcaaa tgtatatggt tcatatacat ccgcaggcac gtaataaagc    6660 gagggggttcg ggtcgaggtc ggctgtgaaa ctcgaaaagg ttccggaaaa caaaaaagag   6720
agtggtaggt aatagtgtta ataataagaa ataaataat agtggtaaga aaggtttgaa    6780
agttgaggaa attgaggata atgtaagtga tgacgagtct atcgcgtcat cgagtacgtt    6840
ttaatcaata tgccttatac aatcaactct ccgagccaat ttgtttactt aagttccgct    6900
tatgcagatc ctgtgcagct gatcaatctg tgtacaaatg cattgggtaa ccagtttcaa    6960
acgcaacaag ctaggacaac agtccaacag caatttgcgg atgcctggaa acctgtgcct    7020
agtatgacag tgagatttcc tgcatcggat ttctatgtgt atagatataa ttcgacgctt    7080
gatccgttga tcacggcgtt attaaatagc ttcgatacta gaaatagaat aatagaggtt    7140
gataatcaac ccgcaccgaa tactactgaa atcgttaacg cgactcagag ggtagacgat    7200
gcgactgtag ctataagggc ttcaatcaat aatttggcta atgaactggt tcgtggaact    7260
ggcatgttca atcaagcaag ctttgagact gctagtggac ttgtctggac cacaactccg    7320
gctacttagc tattgttgtg agatttccta aaataaagtc actgaagact taaaattcag    7380
ggtggctgat accaaaatca gcagtggttg ttcgtccact taaatataac gattgtcata    7440
tctggatcca acagttaaac catgtgatgg tgtatactgt ggtatggcgt aaaacaacgg    7500
aaaagtcgct gaagacttaa aattcagggt ggctgatacc aaaatcagca gtggttgttc    7560
gtccacttaa aaataacgat tgtcatatct ggatccaaca gttaaaccat gtgatggtgt    7620
atactgtggt atggcgtaaa caacggagag gttcgaatcc tcccctaacc gcgggtagcg    7680
gccca                                                               7685

<210> SEQ ID NO 26
<211> LENGTH: 7686
<212> TYPE: DNA
<213> ORGANISM: Tobacco mosaic virus

<400> SEQUENCE: 26
gtatttttac aacaattacc aacaacaaca aacaacagac aacattacaa ttactatta      60 caattacaat ggcatacaca cagacagcta ccacatcagc tttgctggac actgtccgag    120
gaaacaactc cttggtcaat gatctagcaa agcgtcgtct ttacgacaca gcggttgaag    180
agtttaacgc tcgtgaccgc aggcccaagg tgaacttttc aaaagtaata agcgaggagc    240
agacgcttat tgctacccgg gcgtatccag aattccaaat tacattttat aacacgcaaa    300
atgccgtgca ttcgcttgca ggtggattgc gatctttaga actggaatat ctgatgatgc    360
aaattcccta cggatcattg acttatgaca taggcgggaa ttttgcatcg catctgttca    420
agggacgagc atatgtacac tgctgcatgc ccaacctgga cgttcgagac atcatgcggc    480
acgaaggcca gaaagacagt attgaactat acctttctag gctagagaga ggggggaaaa    540
cagtccccaa cttccaaaag gaagcatttg acagatacgc agaaattcct gaagacgctg    600
tctgtcacaa tactttccag acatgcgaac atcagccgat gcagcaatca ggcagagtgt    660
atgccattgc gctacacagc atatatgaca taccagccga tgagttcggg gcggcactct    720
tgaggaaaaa tgtccatacg tgctatgccg ctttccactt ctccgagaac ctgcttcttg    780
aagattcatg cgtcaatttg gacgaaatca acgcgtgttt ttcgcgcgat ggagacaagt    840 tgacctttc ttttgcatca gagagtactc ttaattactg tcatagttat tctaatattc    900
ttaagtatgt gtgcaaaact tacttcccgg cctctaatag agaggtttac atgaaggagt    960
```

-continued

```
ttttagtcac cagagttaat acctggtttt gtaagttttc tagaatagat acttttcttt    1020
tgtacaaagg tgtggcccat aaaagtgtag atagtgagca gttttatact gcaatggaag    1080
acgcatggca ttacaaaaag actcttgcaa tgtgcaacag cgagagaatc ctccttgggg    1140
attcatcatc agtcaattac tggtttccca aaatgaggga tatggtcatc gtaccattat    1200
tcgacatttc tttggagact agtaagagga cgcgcaagga agtcttagtg tccaaggatt    1260
tcgtgttcac agtgcttaac cacattcgaa cataccaggc gaaagctctt acatacgcaa    1320
atgttttgtc cttcgtcgaa tcgattcgat cgagggtaat cattaacggt gtgacagcga    1380
ggtccgaatg ggatgtggac aaatctttgt tacaatcctt gtccatgacg ttttacctgc    1440
atactaagct tgccgttcta aaggatgact tactgattag caagtttagt ctcggttcga    1500
aaacggtgtg ccagcatgtg tgggatgaga tttcgctggc gtttgggaac gcatttccct    1560
ccgtgaaaga gaggctcttg aacaggaaac ttatcagagt ggcaggcgac gcattagaga    1620
tcagggtgcc tgatctatat gtgaccttcc acgacagatt agtgactgag tacaaggcct    1680
ctgtggacat gcctgcgctt gacattagga agaagatgga agaaacggaa gtgatgtaca    1740
atgcactttc agaattatcg gtgttaaggg agtctgacaa attcgatgtt gatgtttttt    1800
cccagatgtg ccaatctttg gaagttgacc caatgacggc agcgaaggtt atagtcgcgg    1860
tcatgagcaa tgagagcggt ctgactctca catttgaacg acctactgag gcgaatgttg    1920
cgctagcttt acaggatcaa gagaaggctt cagaaggtgc attggtagtt acctcaagag    1980
aagttgaaga accgtccatg aagggttcga tggccagagg agagttacaa ttagctggtc    2040
ttgctggaga tcatccggaa tcgtcctatt ctaagaacga ggagatagag tctttagagc    2100
agtttcatat ggcgacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatggggt gttgttgaaa cccacgcgag ggagtatcat gtggcgcttt    2400
tggaatatga tgagcagggt gtggtgacat gcgatgattg gagaagagta gctgttagct    2460
ctgagtctgt tgtttattcc gacatggcga aactcagaac tctgcgcaga ctgcttcgaa    2520
acggagaacc gcatgtcagt agcgcaaagg ttgttcttgt ggacggagtt ccgggctgtg    2580
gaaaaaccaa agaaattctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt accccgccca ttttgccaaa ttggaagttg    2940
acgaggtgga gacacgcaga actactctcc gttgtccagc cgatgtcaca cattatctga    3000
acaggagata tgagggcttt gtcatgagca cttcttcggt taaaaagtct gtttcgcagg    3060
agatggtcga cggagccgcc gtgatcaatc cgatctcaaa accttgcat ggcaagatcc    3120 tgacttttac ccaatcggat aaagaagctc tgctttcaag agggtattca gatgttcaca    3180
ctgtgcatga agtgcaaggc gagacatact ctgatgtttc actagttagg ttaaccccta    3240
caccggtctc catcattgca ggagacagcc cacatgtttt ggtcgcattg tcaaggcaca    3300
```

-continued

```
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgatatgcag ttttactatg ataagtgtct cccaggcaac agcaccatga    3540
tgaataattt tgatgctgtt accatgaggt tgactgacat tcattgaat gtcaaagatt     3600 gcatattgga tatgtctaag tctgttgctg cacctaagga tcaaatcaaa ccactaatac    3660
ctatggtacg aacggcggca gaaatgccac gccagactgg actattggaa atttagtgg     3720 cgatgattaa agaaactttt aacgcacccg agttgtctgg catcattgat attgaaaata    3780
ctgcatcttt ggttgtagat aagttttttg atagttattt gcttaaagaa aaagaaaac     3840 caaataaaaa tgtttctttg ttcagtagag agtctctcaa tagatggtta gaaaagcagg    3900
aacaggtaac aataggccag ctcgcagatt ttgattttgt ggatttgcca gcagttgatc    3960
agtacagaca catgattaaa gcacaaccca acaaaagtt ggacacttca atccaaacgg     4020
agtacccggc tttgcagacg attgtgtacc attcaaaaaa gatcaatgca atattcggcc    4080
cgttgtttag tgagcttact aggcaattac tggacagtgt tgattcgagc agatttttgt    4140
ttttcacaag aaagacacca gcgcagattg aggatttctt cggagatctc gacagtcatg    4200
tgccgatgga tgtcttggag ctggatatat caaaatacga caaatctcag aatgaattcc    4260
actgtgcagt agaatacgag atctggcgaa gattgggttt cgaagacttc ttgggagaag    4320
tttgaaaaca agggcataga aagaccaccc tcaaggatta taccgcaggt ataaaaactt    4380
gcatctggta tcaaagaaag agcggggacg tcacgacgtt cattggaaac actgtgatca    4440
ttgctgcatg ttttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga tacttttgcg    4620
gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt ctttttagaa gtttgtttat agatggctct agttgttaaa    4920
ggaaaagtga atatcaatga gtttatcgac ctgacaaaaa tggagaagat cttaccgtcg    4980
atgtttaccc ctgtaaagag tgttatgtgt tccaaagttg ataaaataat ggttcatgag    5040
aatgagtcat tgtcagggt gaaccttctt aaaggagtta agcttattga tagtggatac     5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cattctcgga    5220
tcttactaca cagcagctgc aaagaaaaga tttcagttca aggtcgttcc caattatgct    5280
ataaccaccc aggacgcgat gagaaacgtc tggcaagttt tagttaatat tagaaatgtg    5340
aagatgtcag cgggtttctg tccgcttttct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa aagagtgatg tccgcaaagg gaaaaatagt    5580
agtagtgatc ggtcagtgcc gaacaagaac tatagaaatg ttaaggattt tggaggaatg    5640
agttttaaaa agaataattt aatcgatgat gattcggagg ctactgtcgc cgaatcggat    5700
```

-continued

```
tcgttttaaa tagatcttac agtatcacta ctccatctca gttcgtgttc ttgtcattaa      5760
ttaaatggct agcaaaggag aagaactttt cactggagtt gtcccaattc ttgttgaatt      5820
agatggtgat gttaatgggc acaaattttc tgtcagtgga gagggtgaag gtgatgctac      5880
atacggaaag cttacactta aatttatttg cactactgga aaactacctg ttccatggcc      5940
aacacttgtc actactttct cttatggtgt tcaatgcttt tcccgttatc cggatcatat      6000
gaaacggcat gacttttca agagtgccat gcccgaaggt tatgtacagg aacgcactat      6060
atctttcaaa gatgacggga actacaagac gcgtgctgaa gtcaagtttg aaggtgatac      6120
ccttgttaat cgtatcgagt taaaggtat tgattttaaa gaagatggaa acattctcgg      6180
acacaaactc gagtacaact ataactcaca caatgtatac atcacggcag acaaacaaaa      6240
gaatggaatc aaagctaact tcaaaattcg ccacaacatt gaagatggat ccgttcaact      6300
agcagaccat tatcaacaaa atactccaat tggcgatggc cctgtccttt taccagacaa      6360
ccattacctg tcgacacaat ctgccctttc gaaagatccc aacgaaaagc gtgaccacat      6420
ggtccttctt gagtttgtaa ctgctgctgg gattacacat ggcatggatg agctctacaa      6480
ataatgacac tcgaggggta gtcaagatgc ataataaata acggattgtg tccgtaatca      6540
cacgtggtgc gtacgataac gcatagtgtt tttccctcca cttaaatcga agggttgtgt      6600
cttggatcgc gcgggtcaaa tgtatatggt tcatatacat ccgcaggcac gtaataaagc      6660 gagggggttcg ggtcgaggtc ggctgtgaaa ctcgaaaagg ttccggaaaa caaaaaagag      6720
agtggtaggt aatagtgtta ataataagaa ataaataat agtggtaaga aaggtttgaa      6780
agttgaggaa attgaggata atgtaagtga tgacgagtct atcgcgtcat cgagtacgtt      6840
ttaatcaata tgccttatac aatcaactct ccgagccaat ttgtttactt aagttccgct      6900
tatgcagatc ctgtgcagct gatcaatctg tgtacaaatg cattgggtaa ccagtttcaa      6960
acgcaacaag ctaggacaac agtccaacag caatttgcgg atgcctggaa acctgtgcct      7020
agtatgacag tgagatttcc tgcatcggat ttctatgtgt atagatataa ttcgacgctt      7080
gatccgttga tcacggcgtt attaaatagc ttcgatacta gaaatagaat aatagaggtt      7140
gataatcaac ccgcaccgaa tactactgaa atcgttaacg cgactcagag ggtagacgat      7200
gcgactgtag ctataagggc ttcaatcaat aatttggcta atgaactggt tcgtggaact      7260
ggcatgttca atcaagcaag ctttgagact gctagtggac ttgtctggac cacaactccg      7320
gctacttagc tattgttgtg agatttccta aaataaagtc actgaagact taaaattcag      7380
ggtggctgat accaaaatca gcagtggttg ttcgtccact taaatataac gattgtcata      7440
tctggatcca acagttaaac catgtgatgg tgtatactgt ggtatggcgt aaaacaacgg      7500
aaaagtcgct gaagacttaa aattcagggt ggctgatacc aaaatcagca gtggttgttc      7560
gtccacttaa aaataacgat tgtcatatct ggatccaaca gttaaaccat gtgatggtgt      7620
atactgtggt atggcgtaaa acaacggaga ggttcgaatc ctcccctaac cgcgggtagc      7680
ggccca                                                                  7686
```

<210> SEQ ID NO 27
<211> LENGTH: 7688
<212> TYPE: DNA
<213> ORGANISM: Tobacco mosaic virus

<400> SEQUENCE: 27

```
gtcgtatttt tacaacaatt accaacaaca acaaacaaca gacaacatta caattactat        60
```

-continued

| | |
|---|---|
| ttacaattac aatggcatac acacagacag ctaccacatc agctttgctg gacactgtcc | 120 |
| gaggaaacaa ctccttggtc aatgatctag caaagcgtcg tctttacgac acagcggttg | 180 |
| aagagtttaa cgctcgtgac cgcaggccca aggtgaactt ttcaaaagta ataagcgagg | 240 |
| agcagacgct tattgctacc cgggcgtatc cagaattcca aattacattt tataacacgc | 300 |
| aaaatgccgt gcattcgctt gcaggtggat tgcgatcttt agaactggaa tatctgatga | 360 |
| tgcaaattcc ctacggatca ttgacttatg acataggcgg gaattttgca tcgcatctgt | 420 |
| tcaagggacg agcatatgta cactgctgca tgcccaacct ggacgttcga gacatcatgc | 480 |
| ggcacgaagg ccagaaagac agtattgaac tataccttc taggctagag agaggggga | 540 |
| aaacagtccc caacttccaa aaggaagcat ttgacagata cgcagaaatt cctgaagacg | 600 |
| ctgtctgtca caatactttc cagacatgcg aacatcagcc gatgcagcaa tcaggcagag | 660 |
| tgtatgccat tgcgctacac agcatatatg acataccagc cgatgagttc ggggcggcac | 720 |
| tcttgaggaa aaatgtccat acgtgctatg ccgcttttcca cttctccgag aacctgcttc | 780 |
| ttgaagattc atgcgtcaat ttggacgaaa tcaacgcgtg ttttttcgcgc gatggagaca | 840 |
| agttgacctt ttcttttgca tcagagagta ctcttaatta ctgtcatagt tattctaata | 900 |
| ttcttaagta tgtgtgcaaa acttacttcc cggcctctaa tagagaggtt tacatgaagg | 960 |
| agtttttagt caccagagtt aatacctggt tttgtaagtt ttctagaata gatacttttc | 1020 |
| ttttgtacaa aggtgtggcc cataaaagtg tagatagtga gcagttttat actgcaatgg | 1080 |
| aagacgcatg gcattacaaa aagactcttg caatgtgcaa cagcgagaga atcctccttg | 1140 |
| aggattcatc atcagtcaat tactggtttc ccaaaatgag ggatatggtc atcgtaccat | 1200 |
| tattcgacat ttctttggag actagtaaga ggacgcgcaa ggaagtctta gtgtccaagg | 1260 |
| atttcgtgtt tacagtgctt aaccacattc gaacatacca ggcgaaagct cttacatacg | 1320 |
| caaatgtttt gtccttcgtc gaatcgattc gatcgagggt aatcattaac ggtgtgacag | 1380 |
| cgaggtccga atgggatgtg gacaaatctt tgttacaatc cttgtccatg acgttttacc | 1440 |
| tgcatactaa gcttgccgtt ctaaaggatg acttactgat tagcaagttt agtctcggtt | 1500 |
| cgaaaacggt gtgccagcat gtgtgggatg agatttcgct ggcgtttggg aacgcatttc | 1560 |
| cctccgtgaa agagaggctc ttgaacagga aacttatcag agtggcaggc gacgcattag | 1620 |
| agatcagggt gcctgatcta tatgtgacct tccacgacag attagtgact gagtacaagg | 1680 |
| cctctgtgga catgcctgcg cttgacatta ggaagaagat ggaagaaacg gaagtgatgt | 1740 |
| acaatgcact ttcagaatta tcggtgttaa gggagtctga caaattcgat gttgatgttt | 1800 |
| tttcccagat gtgccaatct ttggaagttg acccaatgac ggcagcgaag gttatagtcg | 1860 |
| cggtcatgag caatgagagc ggtctgactc tcacatttga acgacctact gaggcgaatg | 1920 |
| ttgcgctagc tttacaggat caagagaagg cttcagaagg tgcattggta gttacctcaa | 1980 |
| gagaagttga agaaccgtcc atgaagggtt cgatggccag aggagagtta caattagctg | 2040 |
| gtcttgctgg agatcatccg gaatcgtcct attctaagaa cgaggagata gagtctttag | 2100 |
| agcagtttca tatggcgacg gcagattcgt taattcgtaa gcagatgagc tcgattgtgt | 2160 |
| acacgggtcc gattaaagtt cagcaaatga aaaactttat cgatagcctg gtagcatcac | 2220 |
| tatctgctgc ggtgtcgaat ctcgtcaaga tcctcaaaga tacagctgct attgaccttg | 2280 |
| aaacccgtca aaagtttgga gtcttggatg ttgcatctag gaagtggtta atcaaaccaa | 2340 |
| cggccaagag tcatgcatgg ggtgttgttg aaacccacgc gaggaagtat catgtggcgc | 2400 |
| ttttggaata tgatgagcag ggtgtggtga catgcgatga ttggagaaga gtagctgtta | 2460 |

-continued

```
gctctgagtc tgttgtttat tccgacatgg cgaaactcag aactctgcgc agactgcttc    2520
gaaacggaga accgcatgtc agtagcgcaa aggttgttct tgtggacgga gttccgggct    2580
gtggaaaaac caaagaaatt ctttccaggg ttaattttga tgaagatcta attttagtac    2640
ctggaagcca agccgcggaa atgatcagaa gacgtgcgaa ttcctcaggg attattgtgg    2700
ccacgaagga caacgttaaa accgttgatt ctttcatgat gaattttggg aaaagcacac    2760
gctgtcagtt caagaggtta ttcattgatg aagggttgat gttgcatact ggttgtgtta    2820
attttcttgt ggcgatgtca ttgtgcgaaa ttgcatatgt ttacgagac acacagcaga    2880 ttccatacat caatagagtt tcaggattcc cgtaccccgc ccattttgcc aaattggaag    2940
ttgacgaggt ggagacacgc agaactactc tccgttgtcc agccgatgtc acacattatc    3000
tgaacaggag atatgagggc tttgtcatga gcacttcttc ggttaaaaag tctgtttcgc    3060
aggagatggt cggcggagcc gccgtgatca atccgatctc aaaaccttg catggcaaga    3120 tcttgacttt tacccaatcg ataaagaag ctctgctttc aagagggtat tcagatgttc    3180
acactgtgca tgaagtgcaa ggcgagcat actctgatt tcactagtt aggttaaccc    3240 ctacaccggt ctccatcatt gcaggagaca gcccacatgt tttggtcgca ttgtcaaggc    3300
acacctgttc gctcaagtac tacactgttg ttatggatcc tttagttagt atcattagag    3360
atctagagaa acttagctcg tacttgttag atatgtataa ggtcgatgca ggaacacaat    3420
agcaattaca gattgactcg gtgttcaaag gttccaatct ttttgttgca cgccaaaga    3480 ctggtgatat ttctgatatg cagttttact atgataagtg tctcccaggc aacagcacca    3540
tgatgaataa ttttgatgct gttaccatga ggttgactga catttcattg aatgtcaaag    3600
attgcatatt ggatatgtct aagtctgttg ctgcgcctaa ggatcaaatc aaaccactaa    3660
tacctatggt acgaacggcg gcagaaatgc cacgccagac tggactattg gaaaatttag    3720
tggcgatgat taaaagaaac tttaacgcac ccgagttgtc tggcatcatt gatattgaaa    3780
atactgcatc tttggttgta gataagtttt ttgatagtta tttgcttaaa gaaaaaagaa    3840
aaccaaataa aaatgtttct ttgttcagta gagagtctct caatagatgg ttagaaaagc    3900
aggaacaggt aacaataggc cagctcgcag attttgattt tgtggatttg ccagcagttg    3960
atcagtacag acacatgatt aaagcacaac ccaaacaaaa gttggacact tcaatccaaa    4020
cggagtaccc ggctttgcag acgattgtgt accattcaaa aaagatcaat gcaatattcg    4080
gcccgttgtt tagtgagctt actaggcaat tactggacag tgttgattcg agcagatttt    4140 tgttttcac aagaaagaca ccagcgcaga ttgaggattt cttcggagat ctcgacagtc    4200
atgtgccgat ggatgtcttg gagctggata tatcaaaata cgacaaatct cagaatgaat    4260
tccactgtgc agtagaatac gagatctggc gaagattggg tttcgaagac ttcttgggag    4320
aagtttggaa acaagggcat agaaagacca ccctcaagga ttataccgca ggtataaaaa    4380
cttgcatctg gtatcaaaga aagagcgggg acgtcacgac gttcattgga aacactgtga    4440
tcattgctgc atgtttggcc tcgatgcttc cgatggagaa aataatcaaa ggagccttt    4500 gcggtgacga tagtctgctg tactttccaa agggttgtga gtttccggat gtgcaacact    4560
ccgcgaatct tatgtggaat tttgaagcaa aactgtttaa aaaacagtat ggatacttt    4620 gcggaagata tgtaatacat cacgacagag gatgcattgt gtattacgat cccctaaagt    4680
tgatctcgaa acttggtgct aaacacatca aggattggga acacttggag gagttcagaa    4740
ggtctctttg tgatgttgct gtttcgttga acaattgtgc gtattacaca cagttggacg    4800
```

```
acgctgtatg ggaggttcat aagaccgccc ctccaggttc gtttgtttat aaaagtctgg    4860
tgaagtattt gtctgataaa gttcttttta gaagtttgtt tatagatggc tctagttgtt    4920
aaaggaaaag tgaatatcaa tgagtttatc gacctgacaa aaatggagaa gatcttaccg    4980
tcgatgttta ccctgtaaa gagtgttatg tgttccaaag ttgataaaat aatggttcat    5040
gagaatgagt cattgtcagg ggtgaacctt cttaaaggag ttaagcttat tgatagtgga    5100
tacgtctgtt tagccggttt ggtcgtcacg ggcgagtgga acttgcctga caattgcaga    5160
ggaggtgtga gcgtgtgtct ggtggacaaa aggatgaaa gagccgacga ggccattctc    5220
ggatcttact acacagcagc tgcaaagaaa agatttcagt tcaaggtcgt tcccaattat    5280
gctataacca cccaggacgc gatgaaaaac gtctggcaag ttttagttaa tattagaaat    5340
gtgaagatgt cagcgggttt ctgtccgctt tctctggagt ttgtgtcggt gtgtattgtt    5400
tataaaaata atataaaatt aggtttgaga gagaagatta caaacgtgag agacggaggg    5460
cccatggaac ttacagaaga agtcgttgat gagttcatgg aagatgtccc tatgtcgatc    5520
aggcttgcaa agtttcgatc tcgaaccgga aaaagagtg atgtccgcaa agggaaaaat    5580
agtagtagtg atcggtcagt gccgaacaag aactatagaa atgttaagga ttttggagga    5640
atgagtttta aaagaataa tttaatcgat gatgattcgg aggctactgt cgccgaatcg    5700
gattcgtttt aaatagatct tacagtatca ctactccatc tcagttcgtg ttcttgtcat    5760
taattaaatg gctagcaaag gagaagaact tttcactgga gttgtcccaa ttcttgttga    5820
attagatggt gatgttaatg gcacaaaatt ttctgtcagt ggagagggtg aaggtgatgc    5880
tacatacgga aagcttaccc ttaaatttat ttgcactact ggaaaactac ctgttccatg    5940
gccaacactt gtcactactt tctcttatgg tgttcaatgc ttttcccgtt atccggatca    6000
tatgaaacgg catgactttt tcaagagtgc catgcccgaa ggttatgtac aggaacgcac    6060
tatatctttc aaagatgacg ggaactacaa gacgcgtgct gaagtcaagt ttgaaggtga    6120 taccccttgtt aatcgtatcg agttaaaagg tattgatttt aaagaagatg gaaacattct    6180
cggacacaaa ctcgagtaca actataactc acacaatgta tacatcacgg cagacaaaca    6240
aaagaatgga atcaaagcta acttcaaaat tcgccacaac attgaagatg gatccgttca    6300
actagcagac cattatcaac aaaatactcc aattggcgat ggccctgtcc ttttaccaga    6360
caaccattac ctgtcgacac aatctgccct ttcgaaagat cccaacgaaa agcgtgacca    6420
catggccctt cttgagtttg taactgctgc tgggattaca catggcatgg atgagctcta    6480
caaataatga cactcgaggg gtagtcaaga tgcataataa ataacggatt gtgtccgtaa    6540
tcacacgtgg tgcgtacgat aacgcatagt gttttttccct ccacttaaat cgaagggttg    6600
tgtcttggat cgcgcgggtc aaatgtatat ggttcatata catccgcagg cacgtaataa    6660
agcgaggggt tcgggtcgag gtcggctgtg aaactcgaaa aggttccgga aaacaaaaaa    6720
gagagtggta ggtaatagtg ttaataataa gaaataaat aatagtggta agaaaggttt    6780
gaaagttgag gaaattgagg ataatgtaag tgatgacgag tctatcgcgt catcgagtac    6840
gttttaatca atatgcctta taatcaac tctccgagcc aatttgttta cttaagttcc    6900
gcttatgcag atcctgtgca gctgatcaat ctgtgtacaa atgcattggg taaccagttt    6960
caaacgcaac aagctaggac aacagtccaa cagcaatttg cggatgcctg aaacctgtg    7020 cctagtatga cagtgagatt tcctgcatcg gatttctatg tgtatagata taattcgacg    7080
cttgatccgt tgatcacggc gttattaaat agcttcgata ctagaaatag aataatagag    7140
gttgataatc aacccgcacc gaatactact gaaatcgtta acgcgactca gagggtagac    7200
```

```
gatgcgactg tagctataag ggcttcaatc aataatttgg ctaatgaact ggttcgtgga    7260
actggcatgt tcaatcaagc aagctttgag actgctagtg gacttgtctg gaccacaact    7320
ccggctactt agctattgtt gtgagatttc ctaaaataaa gtcactgaag acttaaaatt    7380
cagggtggct gataccaaaa tcagcagtgg ttgttcgtcc acttaaatat aacgattgtc    7440
atatctggat ccaacagtta aaccatgtga tggtgtatac tgtggtatgg cgtaaaacaa    7500
cggaaaagtc gctgaagact taaaattcag ggtggctgat accaaaatca gcagtggttg    7560
ttcgtccact taaaaataac gattgtcata tctggatcca acagttaaac catgtgatgg    7620
tgtatactgt ggtatggcgt aaacaacgga gaggttcgaa tcctcccta accgcgggta    7680 gcggccca                                                            7688
```